United States Patent
Chertov et al.

(10) Patent No.: US 9,746,410 B2
(45) Date of Patent: *Aug. 29, 2017

(54) SYSTEM AND METHODOLOGY FOR DETERMINING PROPERTIES OF A SUBSTANCE

(71) Applicant: Schlumberger Technology Corporation, Sugar Land, TX (US)

(72) Inventors: Maxim Andreevich Chertov, Salt Lake City, UT (US); Roberto Suarez-Rivera, Salt Lake City, UT (US); Dean M. Willberg, Salt Lake City, UT (US); Sidney J. Green, Salt Lake City, UT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/762,258

(22) PCT Filed: Feb. 5, 2014

(86) PCT No.: PCT/US2014/014812
§ 371 (c)(1),
(2) Date: Jul. 21, 2015

(87) PCT Pub. No.: WO2014/123966
PCT Pub. Date: Aug. 14, 2014

(65) Prior Publication Data
US 2015/0369719 A1 Dec. 24, 2015

Related U.S. Application Data

(60) Provisional application No. 61/762,617, filed on Feb. 8, 2013.

(51) Int. Cl.
*G01N 15/08* (2006.01)
*G01N 7/00* (2006.01)
*G01N 33/24* (2006.01)

(52) U.S. Cl.
CPC ............ *G01N 15/082* (2013.01); *G01N 7/00* (2013.01); *G01N 15/08* (2013.01);
(Continued)

(58) Field of Classification Search
CPC .. G01N 15/08; G01N 15/082; G01N 15/0826; G01N 15/088; G01N 15/0806;
(Continued)

(56) References Cited

U.S. PATENT DOCUMENTS 2,829,515 A * 4/1958 Johnson ............... G01N 15/088
73/38
3,839,899 A * 10/1974 McMillen ............ G01N 15/088
73/38

(Continued)

FOREIGN PATENT DOCUMENTS

GB       2468043 A       8/2010
KR    101223462 B1      1/2013

OTHER PUBLICATIONS

Civan, et al., "Determining Shale Permeability to Gas by Simultaneous Analysis of Various Pressure Tests", Sep. 1, 2012, SPE Journal 144253-PA, vol. 17, No. 3, pp. 721-726.

(Continued)

*Primary Examiner* — Nguyen Ha
(74) *Attorney, Agent, or Firm* — Tuesday Kaasch

(57) ABSTRACT

A method for characterizing properties of a porous sample that employs a test apparatus including a sample cell and associated pressure sensor having a configuration that measures pressure of the isolated sample cell. The porous sample is divided into a number of pieces, which are loaded into the
(Continued)

sample cell. The test apparatus is configured to perform a sequence of test operations whereby the loaded isolated sample cell is filled with test fluid under pressure and the pressure sensor is used to generate and store pressure data over time. A data processing system processes the pressure data in conjunction with a computational model that includes a set of pressure curves with a number of curve-related variables and associated values in order to identify a matching pressure curve, and processes the variable values for the matching pressure curve in order to derive bulk properties of the porous sample.

18 Claims, 24 Drawing Sheets

(52) U.S. Cl.
CPC ....... *G01N 15/0806* (2013.01); *G01N 15/088* (2013.01); *G01N 15/0826* (2013.01); *G01N 33/24* (2013.01)

(58) Field of Classification Search
CPC .. G01N 7/00; G01N 7/02; G01N 7/14; G01N 33/24
See application file for complete search history.

(56) References Cited

U.S. PATENT DOCUMENTS

| | | | | |
|---|---|---|---|---|
| 4,555,934 | A * | 12/1985 | Freeman | G01N 15/0826 73/38 |
| 5,261,267 | A | 11/1993 | Kamath et al. | |
| 5,513,515 | A * | 5/1996 | Mayer | G01N 15/0826 73/38 |
| 5,708,204 | A | 1/1998 | Kasap | |
| 7,082,812 | B2 | 8/2006 | Lenormand et al. | |
| 7,388,373 | B2 | 6/2008 | Lenormand et al. | |
| 7,555,934 | B2 | 7/2009 | DeRoos et al. | |
| 7,693,677 | B2 * | 4/2010 | Egermann | G01N 15/0826 702/127 |
| 2002/0029615 | A1 * | 3/2002 | Lenormand | G01N 15/08 73/38 |
| 2004/0211252 | A1 | 10/2004 | Lenormand et al. | |
| 2005/0178189 | A1 * | 8/2005 | Lenormand | G01N 15/0826 73/38 |
| 2009/0005996 | A1 * | 1/2009 | Delorme | E21B 49/00 702/12 |
| 2009/0084164 | A1 * | 4/2009 | Lowery | G01F 1/36 73/38 |
| 2010/0223979 | A1 * | 9/2010 | Ploehn | G01N 15/0826 73/38 |

OTHER PUBLICATIONS

Ning, et al., "The measurement of gas relative permeability for low permeability cores using a pressure transient method", Dec. 1, 1989, Masters Thesis, Texas A&M University, pp. 1-97.
Cui, et al., "Measurements of gas permeability and diffusivity of tight reservoir rocks: different approaches and their applications", Aug. 1, 2009, Geofluids, vol. 9, No. 3, pp. 208-223.
Extended European Search Report issued in related EP application 15160437.4 on Jan. 8, 2016, 7 pages.
European Search Report issued in related EP application 14748895.1 on Jan. 8, 2016, 4 pages.
European Search Report issued in related EP application 14749191.4 on Jan. 13, 2016, 3 pages.
European Search Report issued in related EP application 14749295.3 on Jan. 15, 2016, 3 pages.
Office Action issued in related EP application 14748895.1 on Jan. 21, 2016, 4 pages.
European Search Report issued in related EP application 14748832.4 on Feb. 1, 2016, 4 pages.
Office Action issued in related EP application 14749191.4 on Feb. 3, 2016, 4 pages.
Office Action issued in related EP application 14748832.4 on Feb. 23, 2016, 4 pages.
Luffel, Di., Hopkins, C.W., Shettler, P.D. (1993) Matrix permeability measurements of gas productive shales, SPE 26633 presented at the 1993 SPE Annual Technical Conference and Exhibition Oct. 3-6, 1993, Houston, TX, USA. (10 pages).
Cui, X., Bustin, R. M., Brezovski, R., Nassichuk, B., Glover, K., Pathi, V. (2010) A new method to simultaneously measure in-situ permeability and porosity under reservoir conditions: implications for characterization of unconventional gas reservoirs, SPE 138148 presented at the 2010 SPE Canadian Unconventional Resources & International Petroleum Conference Oct. 19-21, 2010, Calgary, Canada. (8 pages).
Lenormand, R., Fonta, O., Advances in Measuring Porosity and Permeability From Drill Cuttings , SPE 111286 presented at the 2007 SPE/EAGE Reservoir Characterization and Simulation Conference Oct. 28-31, 2007, Abu-Dhabi, U.A.E. (9 pages).
Egermann, P., Lenormand, R., Longeron, D., A fast and direct method or permeability measurements on drill cuttings, SPE 77563 presented at the 2002 SPE Annual Technical Conference and Exhibition Sep. 29-Oct. 2, 2002, San Antonio, TX, USA. (8 pages).
Egermann, P., Doerler, N., Fleury, M., Behot, J., Deflandre, F., Lenormand, R., Petrophysical Measurements From Drill Cuttings: An Added Value for the Reservoir Characterization Process , SPE 88684 presented at the 2004 SPE Abu Dhabi international Petroleum Exhibition and Conference Oct. 10-13, 2004, Abu Dhabi, U.A.E (8 pages).
Sondergeld, C.H., Newsham, K.E., Comisky, J.T., Rice, M.C., Rai, C.S. Petrophysical Considerations in Evaluating and Producing Shale Gas Resources, SPE 131768 presented at the 2010 SPE Unconventional gas conference Feb. 23-25, 2010, Pittsburgh, PA, USA. (34 pages).
Civian, F., Sondergeld, C.H, Rai, C.S., Intrinsic Shale Permeability Determined by Pressure-Pulse Measurements Using a Multiple-Mechanism Apparent-Gas-Permeability Non-Darcy Model, SPE 135087 presented at the 2010 SPE Annual Technical Conference and Exhibition Sep. 19-22, 2010, Florence, Italy (11 pages)
Civian, F., Sondergeld, C.H, Rai, C.S., 'Shale Permeability Determined by Simultaneous Analysis of Multiple Pressure-Pulse Measurements Obtained under Different Conditions, SPE 144253 presented at the 2011 SPE north American unconventional Gas Conference and Exhibition Jun. 14-16, 2011, Woodlands, TX, USA. (22 pages).
Beskok A. and Karniadakis G.E., A model for flows in channels, pipes and ducts at micro-scales and nano-scales, J. Microscale Thermophysical Engineering, vol. 3, pp. 43-77, 1999.
Fathi, E., Tinni, A., Akkutlu, I., Shale gas correction to Klinkenberg slip theory, SPE 154977 presented at the 2012 SPE American unconventional resources conference Jun. 5-7, 2012, Pittsburgh, PA, USA.
American Petroleum Institute (API) (1998) Recommended Practices for Core Analysis, Recommended Practice 40, 2nd edn. API, Dallas, TX. (236 pages).
Klinkenberg, L. J., "The Permeability of Porous Media to Liquids and Gases," Drilling and Production Practice, 1941, 200-213.
Billiotte et al., Experimental Study on Gas permeability of Mudstone, Physics and Chemistry of the Earth, Part A/B/C, 2008, vol. 33, pp. S231-S236.
International Search report and Written Opinion issued in the related PCT application PCT/US2014/014825, dated May 20, 2014 (9 pages).
International Preliminary Report on Patentability issued in the related PCT application PCT/US2014/014825, dated Aug. 11, 2015 (5 pages).
International Search report and Written Opinion issued in the related PCT application PCT/US2014/014812, dated Jul. 17, 2014 (11 pages).

(56) References Cited

OTHER PUBLICATIONS

International Preliminary Report on Patentability issued in the related PCT application PCT/US2014/014812, dated Aug. 11, 2015 (7 pages).

International Search report and Written Opinion issued in the related PCT application PCT/US2014/014773, dated Nov. 6, 2014 (11 pages).

International Preliminary Report on Patentability Opinion issued in the related PCT application PCT/US2014/014773, dated Aug. 11, 2015 (7 pages).

Office action issued in the related EP application 14749295.3, dated Jan. 29, 2016 (4 pages).

International Search report and Written Opinion issued in the related PCT application PCT/US2014/014850, dated May 20, 2014 (12 pages).

International Preliminary Report on Patentability issued in the related PCT application PCT/US2014/014850, dated Aug. 11, 2015 (08 pages).

* cited by examiner

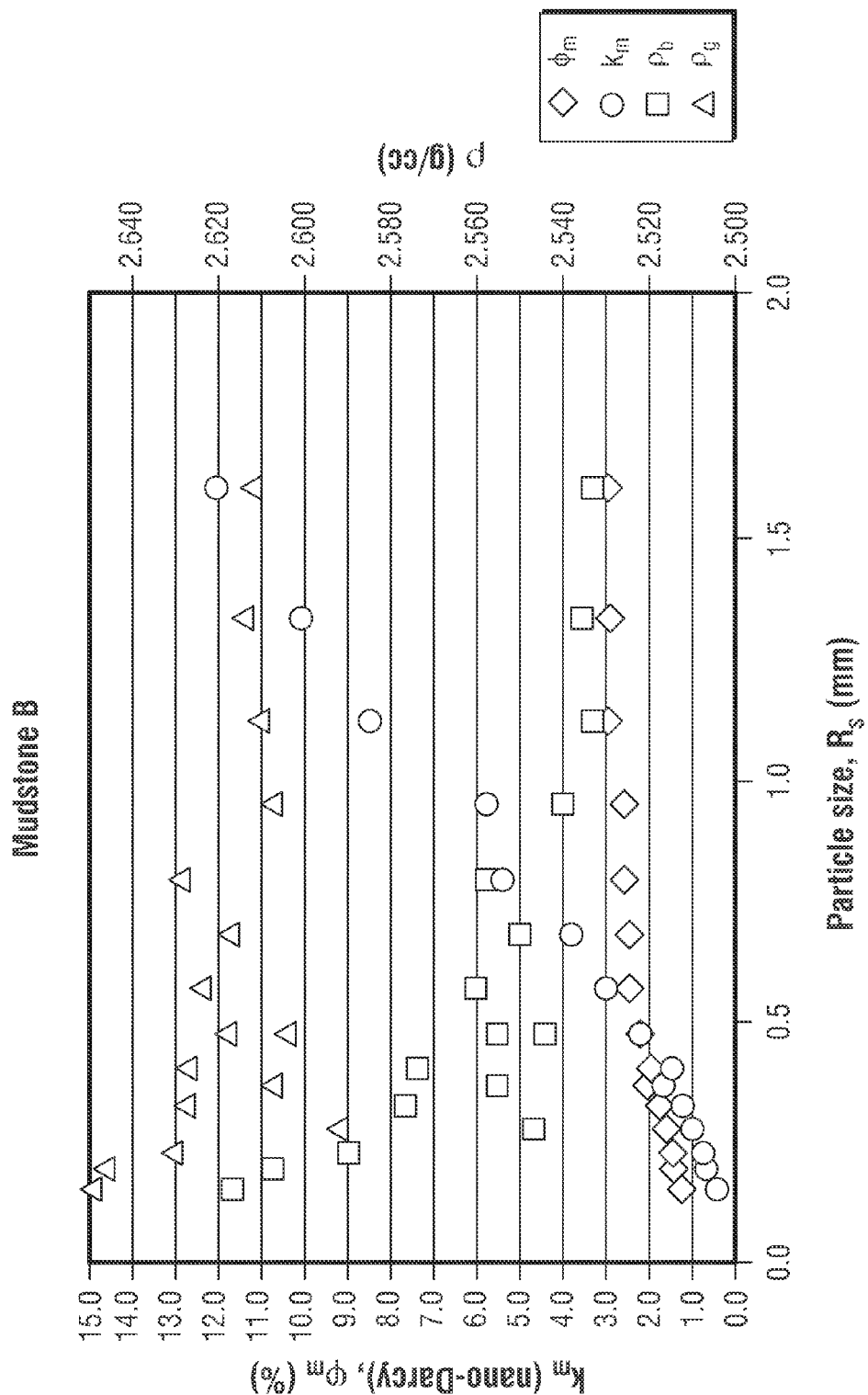

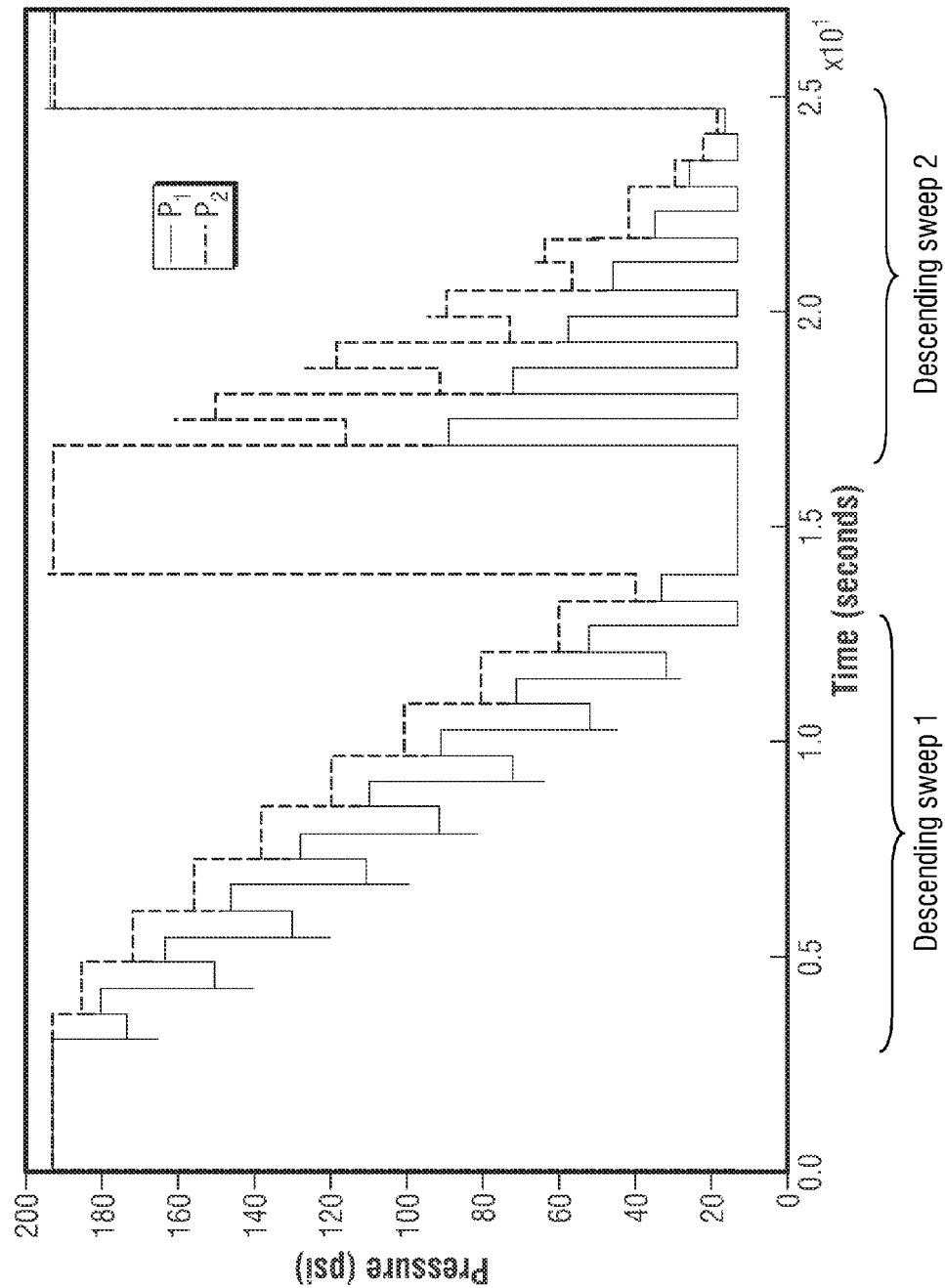

SYSTEM AND METHODOLOGY FOR DETERMINING PROPERTIES OF A SUBSTANCE

BACKGROUND

Field

The present application relates to apparatus and methodology for measuring properties of microporous material such as reservoir rock and core samples extracted from geologic formations.

Related Art

Permeability of a material is a macroscopic property of the material which characterizes the ease with which a fluid can be made to flow through the material by an applied pressure gradient. Thus, permeability is the fluid conductivity of the material. Porosity is the fraction of the bulk volume of the material that is occupied by voids. The total fractional volume of pores in the material can be referred to as total porosity; the fractional volume of only those pores in the material which, under given conditions, are interconnected is known as effective porosity. Only effective porosity contributes to the permeability of the material. In this application, the term "porosity" is used to describe the effective porosity of the material.

Methods for evaluating the permeability of reservoir rock using crushed fragments is described in the paper by Luffel et al. entitled "Matrix permeability measurements of gas productive shales," SPE 26633, 1993, which reported results of a Gas Research Institute (GRI) study. These methods apply a rapid gas pressure pulse to porous sample fragments inside a container with known volume, and use transient measurements of the pressure decline rate inside the container over time to interpret the permeability of the fragments. Permeability is estimated by matching the experimental pressure curves with numerically simulated curves of pressure diffusion into multiple cylindrical fragments with fixed aspect ratio (diameter twice the height) and same size. However, no other details about assumptions in their mathematical model are disclosed. The Luffel et al. paper also presents experimental results with a very good match between permeabilities measured by pressure decay and permeabilities measured on plugs, as well as some discussion of gas slippage effects.

Several methods for measuring permeability of reservoir rock are described in the paper by Cui et al. entitled "Measurements of gas permeability and diffusivity of tight reservoir rocks: different approaches and their applications," Geofluids, 9, 2009, pp. 208-223. These methods (including pulse decay test, pressure decay tests and canister desorption tests) can account for adsorption/desorption effects, which are taken into account as a constant correction to the diffusivity coefficient. The analysis of experimental curves is based on comparison with the exact analytical solution of a pressure diffusion equation that has constant coefficients and also involves multiple rock fragments of the same size and spherical shape. The early-time and late-time approximations to the overall solution of the pressure diffusion problem are compared. The method is based on fitting of experimental curves to the square-root of time asymptote of the analytic solution at $t \rightarrow 0$ and to the single-exponent asymptote of the analytic solution at $t \rightarrow \infty$. Based on the results of this comparison, performed using numerical modeling, the authors suggest that fitting of the late-time behavior results in better accuracy in the inferred permeability.

Methods for simultaneous measurement of stress-dependent in-situ permeability and porosity (or ISPP) are described in the paper by Cui et al., entitled "A new method to simultaneously measure in-situ permeability and porosity under reservoir conditions: implications for characterization of unconventional gas reservoirs," SPE 138148, 2010. These methods are essentially the same method developed for rock fragments as described in SPE 26633, but applied to plug samples. In addition, the samples are subjected to tri-axial loading, to simulate reservoir conditions of stress. In this setup, one of the sample sides is connected to a reference cell with known volume. After the initial pressure differential between the gas in the sample's pore volume and the reference volume, at a particular condition of stress, is created and stabilized the valve connecting the two volumes is opened and the transient process of pressure equilibration is recorded and interpreted to infer the new porosity and permeability of the sample under the newly applied stress. The paper compares the permeability values obtained by ISPP and the conventional pulse decay method on plugs. During pressure decay gas flows through the length of a plug sample, by controlling the pressure difference at both ends of the sample, under controlled conditions of confining stress. Cui et al. report the difference in the ISPP and pulse decay permeabilities to be up to two orders of magnitude, which is explained by the intrinsic heterogeneity of samples. The study also reports considerable variation of permeability and porosity with confining stress, measured with the ISPP system. The authors indicate that the major advantage of the ISPP method compared to the traditional pressure decay method using crushed material is the ability to stress the samples. This is not possible when using fragments. The disadvantage is that increasing the size of the sample tested considerably increases the testing time. For very low permeability samples (assuming 1 inch (25.4 mm) plugs and tens of nano-Darcy or less permeability) it may take hours and be impractical for commercial laboratory services.

Several SPE papers by Lenormand et al. including i) "Advances In Measuring Porosity And Permeability From Drill Cuttings, SPE 111286, 2007; ii) "A fast and direct method of permeability measurements on drill cuttings," SPE 77563, 2002; and iii) "Petrophysical Measurements From Drill Cuttings: An Added Value for the Reservoir Characterization Process", SPE 88684, 2004—consider a concept analogous to pressure decay that uses the injection of viscous liquid (oil) into rock fragments (drill cuttings). SPE 77563 gives a detailed description of this concept. The method relies on the assumption that after initial liquid saturation of rock fragments at atmospheric pressure the fragments still have some of their pore volume (~10%) uniformly filled by a trapped gas; which is trapped in the form of multiple pockets of gas isolated by liquid. During the liquid injection the residual gas volume provides compressibility that enables the flow of liquid into the particles. Both cumulative injected volume and fluid pressure in the cell are recorded at about 500 Hz sampling rate, and the permeability is interpreted based on comparisons with numerical simulations. By controlling the size of the fragments and the liquid viscosity the authors report a wide range of measureable permeabilities from 0.1 to 2000 milli-Darcy. Unfortunately, due to the high viscosity of the liquids used, compared to gas, the measurable permeability range of this system is only suitable for conventional reservoir rocks and not suitable for sub-micro Darcy unconventional reservoir rocks.

It is believed that all existing methods that characterize the permeability of rock samples using the pressure decay method employ a connected cell testing configuration. This means that after the pressure decay test is started, by opening the valve connecting the sample cell and the reference cell, this valve is maintained open throughout the test while the pressure in the sample pore volume is equilibrated to the pressure of the reference cell. In such testing, the reference and the sample cells are connected throughout the whole test, and the one pressure measurement of the reference cell is used to characterize the pressure equilibration process.

Considerable research attention has been given to non-Darcy gas flow regimes in microporous reservoir rocks. Due to the very small pore sizes in low permeability rocks, the ratio of mean free path of the gas molecules to the characteristic length scale of the flow channels becomes non-negligible. This ratio is also known as Knudsen number $K_n$. The higher this is, the larger the departure from Darcy regime and thus from defining the Darcy permeability of the medium. A zero value of this number ($K_n=0$) satisfies the Darcy regime. An overview of this effect to permeability measurements in tight shales is given, for example, in the paper by Sondergeld et al., "Petrophysical Considerations in Evaluating and Producing Shale Gas Resources," SPE 131768, 2010.

In addition, the paper by Civan et al., "Intrinsic Shale Permeability Determined by Pressure-Pulse Measurements Using a Multiple-Mechanism Apparent-Gas-Permeability Non-Darcy Model," SPE 135087, 2010 and the paper by Civan et al., "Shale Permeability Determined by Simultaneous Analysis of Multiple Pressure-Pulse Measurements Obtained under Different Conditions," SPE 144253, 2011 describe pulse-decay and steady-state permeability measurements on plug samples, with elaborated consideration of variable gas compressibility, incorporating the effects of fluid density, adsorption, core porosity variation with stress, and also taking into account the effects of Knudsen flow on the apparent permeability. The latter was done using a model defined by Beskok and Karniadakis, "A model for flows in channels, pipes and ducts at micro- and nano-scales," *Journal of Microscale Thermophysical Engineering*, Vol. 3, pp. 43-77, 1999.

Fathi et al., "Shale gas correction to Klinkenberg slip theory," SPE 154977, 2012 describes the 'double-slip' correction to the Klinkenberg slip theory, with specific application to shale gas. The correction is based on theoretical modeling of gas flow in nano-capillaries using the Lattice Boltzmann Method (LBM). The correction modifies the Klinkenberg factor between the apparent and intrinsic fluid permeability to include a second order pressure correction and an effective capillary size. The correction relationship converges to the traditional Klinkenberg equation at smaller $K_n$ and becomes unity when $K_n$ is negligibly small. Two procedures are presented to estimate the intrinsic liquid permeability of samples. The first procedure is based on the estimation of the characteristic pore size h of the sample, using known porosimetry methods. With this input, the value of liquid permeability is determined from a look-up table, pre-calculated using Lattice Boltzmann Method (LBM) simulations, which provides a one-to-one relationship between h and permeability. The second procedure is based on matching the experimental values of routine pressure decay permeability on rock fragments and measured at different pore pressures, with theoretical LBM curves defining variation of apparent permeability with pore pressure. The theoretical curves are parameterized by pore pressure; the best-match effective pore size is recalculated to liquid permeability using the analytic formula $k=c/\pi h^2$, where c is the geometric factor equal to 8 or 12 for cylindrical and slit pores. The idea of introducing Knudsen flow into the interpretation of pressure decay measurements pursued by Fathi has high practical value. However, the step-by-step procedures presented in his work have three critical drawbacks that make the method impractical for determining absolute permeability values: 1) the one-to-one relationship between the pore size and permeability is too strong an assumption for natural materials with heterogeneous fabric, which will not hold for combinations of pore sizes with different geometries; 2) the paper indicates that the estimation of permeability from pore size using the analytic formula and the look-up table is interchangeable in case of large channels and nearly Darcy flow; yet, the difference is several orders of magnitude; 3) the relationship between the sample's permeability and the characteristic pore size should include the porosity of the sample, otherwise the density of flow channels per unit area is not determined.

All known existing variants of the pressure decay method are directed to measuring the single permeability of the tested sample. Therefore, existing methods do not recognize the fact that many porous materials, particularly naturally formed reservoir rocks having complex fabric, incorporate wide distribution of permeabilities due to their heterogeneous nature. Furthermore, it is believed that the interpretation methods described in the literature assume isothermal conditions without explicit treatment of thermal fluctuations arising during transient gas pressure testing. However, the importance of thermal effects is known, and the American Petroleum Institute (API) document, "*Recommended Practices for Core Analysis,*" Recommended Practice 40, $2^{nd}$ *Edn.*, 1998, gives extensive useful recommendations on how to maintain the isothermal testing conditions during transient measurements.

Furthermore, it is believed that standard methods that characterize permeability of rock samples using the pressure decay method employ a connected cell testing configuration. This means that after the pressure decay test is started, by opening the valve connecting the sample cell and the reference cell, this valve is maintained open throughout the test while the pressure in the sample pore volume is equilibrated to the pressure of the reference cell. In such testing, the reference and the sample cells are connected throughout the whole test, and the one pressure measurement of the reference cell is used to characterize the pressure equilibration process.

The document by the American Petroleum Institute (API), "Recommended Practices for Core Analysis," Recommended Practice 40, $2^{nd}$ Edition, 1998 gives extensive useful recommendations on how to maintain the isothermal testing conditions during transient measurements. At the same time, it is believed the interpretation methods described in the open literature assume isothermal conditions without explicit treatment of thermal fluctuations arising during transient gas pressure testing.

Permeability measurements of ultra low permeability, microporous materials present challenges, particularly, in heterogeneous unconventional reservoir rocks. First, coring and core handling of heterogeneous rock samples can create extensive microcracking. The presence of these microcracks directly affects the permeability measured, and the lower the rock permeability, the larger the effect of the induced microcracks. This effect is most prevalent for laminated, low permeability, organic-rich, mudstones, where the organic to mineral contact and the interfaces associated with the laminated fabric are weak contacts that are prone to part during unloading. (This effect is less important for conventional, higher permeability rocks.)

A second challenge in measuring permeability of unconventional formations, low permeability rocks, is heterogeneity. These rocks possess intrinsic variability in texture and composition that results from geologic processes of deposition and diagenesis. As a result, these rocks exhibit a broad distribution of permeabilities. Unfortunately, conventional permeability measurements developed for homogeneous media, have focused on the evaluation of a single representative value of permeability, without accounting for the distribution of permeabilities. The resulting consequences are that the "single permeability" is ill-defined and not necessarily representative of the rock containing the distribution of permeabilities.

A third challenge to measuring permeability, if more conventional fluid flow through plug samples is used for permeability measurements, is the difficulty of flowing through the samples. It can take impractical times to detect measureable flow through samples of standard size (e.g., 1 to 1.5 inch (25.4 to 38.1 mm) in diameter and 1 to 2 inches (25.4 to 50.8 mm) in length). During these long periods of time, it may simply be impossible to not have small leaks that distort the flow measurements and thereby yield incorrect permeability inferences.

The method using crushed fragments of sample tends to be the standard method most often used for measuring permeability in ultra-low permeability rocks. However, the crushed sample fragments' measured permeabilities do not represent the mean value of the whole permeability distribution of the rock before it was crushed, unless a further calibration or correction is made to these measurements.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method for characterizing properties of a porous sample (such as a sample of reservoir rock) that employs a test apparatus including a sample cell and associated first pressure sensor. The sample cell has a configuration where the sample cell is filled with test fluid under pressure and isolated from other parts of the test apparatus. The first pressure sensor has a configuration that measures pressure of the sample cell when the sample cell is isolated from other parts of the test apparatus. The porous sample is divided into a number of pieces (which can be fragments or can have a controlled shaped). The pieces of the porous sample are loaded into the sample cell of the test apparatus. The test apparatus is configured to perform a sequence of test operations whereby the loaded sample cell is filled with test fluid under pressure and isolated from other parts of the test apparatus and the first pressure sensor is used to measure and store pressure data that represents pressures measured by the pressure sensor over time. A data processing system is configured to process the pressure data in conjunction with a computational model that includes a set of pressure curves with a number of curve-related variables and associated values in order to identify a matching pressure curve. The data processing system processes the values of the curve-related variables for the matching pressure curve in order to derive bulk properties of the porous sample.

In one embodiment, the test apparatus can include an intake valve fluidly coupled to a source of test fluid, a reference cell fluidly coupled to the source of test fluid via the intake valve, an isolation valve fluidly coupled between the reference cell and the sample cell, an exhaust port, an exhaust valve fluid coupled between the sample cell and the exhaust port, and a second pressure sensor associated with the reference cell for measuring pressure within the reference cell. The intake valve, the isolation valve, and the exhaust valve can be electronically-controlled, and the data processing system can interface to the intake valve, the isolation valve, and the exhaust valve via electronic signals communicated therebetween in order to control operation of the intake valve, the isolation valve, and the exhaust valve. The data processing system can also interface to the first and second pressure sensors via electronic signals communicated therebetween in order to generate and store first and second pressure data representing the pressures measured by the first and second pressure sensors, respectively, over time.

The bulk properties of the porous sample derived by the method can be selected from the group consisting of bulk volume, bulk density, porosity, permeability, grain volume, grain density, and effective density-based porosity.

The computational model of the method can be based on an analytical decay function that includes three parameters $\alpha$, $\beta$ and $\tau$, where the parameter $\alpha$ is a storage coefficient that defines the ratio of pore volume to dead volume in the sample under test, the parameter $\beta$ relates to the final pressure in the sample cell when pressure inside and outside of the pore volume of the sample under test has stabilized, and parameter $\tau$ is a relaxation time. In this case, the bulk properties of the porous sample can be selected from the group consisting of bulk volume based on value of the parameter $\beta$ for the matching pressure curve, porosity based on value of the parameter $\alpha$ for the matching pressure curve, permeability based on the parameter $\tau$ for the matching pressure curve, grain volume based on the bulk volume and the porosity, bulk density based on bulk volume, grain density based on grain volume, and effective density-based porosity based on bulk and grain density.

In one embodiment, the data processing system is configured to derive corrected pressure values based on the pressure data and match the corrected pressure values to the set of pressure curves derived from the computational model in order to identify a matching pressure curve.

In one embodiment, the pieces loaded into the sample cell for the test have different sizes. For example, the pieces can be fragments of uncontrolled shape with sizes corresponding to the radius of such fragments. In another example, the pieces can have a controlled shape (such as core sample slices) with sizes corresponding to thickness of the controlled shape.

As part of the method, the data processing system can be configured to process the pressure data in conjunction with the computational model in order to identify value of the parameter $\tau$ for the matching pressure curve and to determine if the sample pieces require reduction in size based on the value of the parameter $\tau$ for the matching pressure curve. For example, the data processing system can compare the time period of the pressure data as measured by the pressure sensor with the parameter $\tau$ for the matching pressure curve to determine if the sample pieces require reduction in size.

The method can further include additional operations as follows:

partitioning the sample pieces into size-groups of different sizes, performing a sequence of operations for each given size-group of sample pieces, wherein the sequence of operations includes s1) loading one or more pieces of the given size-group into the sample cell of the test apparatus, s2) subsequent to s1), configuring the test apparatus to perform a sequence of test operations whereby the loaded sample cell is filled with test fluid under pressure and isolated from other parts of the test apparatus and the first pressure sensor is used to measure and store pressure data that represents pressures measured by the first pressure sensor over time, s3) using the data processing system to process the pressure data generated and stored in s2) in conjunction with the computational model order to identify a matching pressure curve, and s4) using the data processing system to process the values of the curve-related variables for the matching pressure curve identified in s3) in order to derive properties of given size-group of pieces.

The processing of s3) can derive corrected pressure values based on the pressure data generated and stored in s2) and matches the corrected pressure values to the set of pressure curves derived from the computational model in order to identify the matching pressure curve.

BRIEF DESCRIPTION OF THE DRAWINGS

FIGS. 7A and 7B show an exemplary visualization for two different heterogeneous rocks (Mudstone A and Mudstone B), respectively, where porosity, permeability, and bulk and grain density are plotted as functions of particle size.

FIGS. 12A and 12B are exemplary pressure curves recorded by descending and ascending 'sweep 1' and 'sweep 2' calibration scripts, respectively, which can be used for precise estimation of system volumes, calibration for pressure non-linearity, volume compressibility, and for measurements of pressure-dependent permeability.

DETAILED DESCRIPTION

Figure 1:
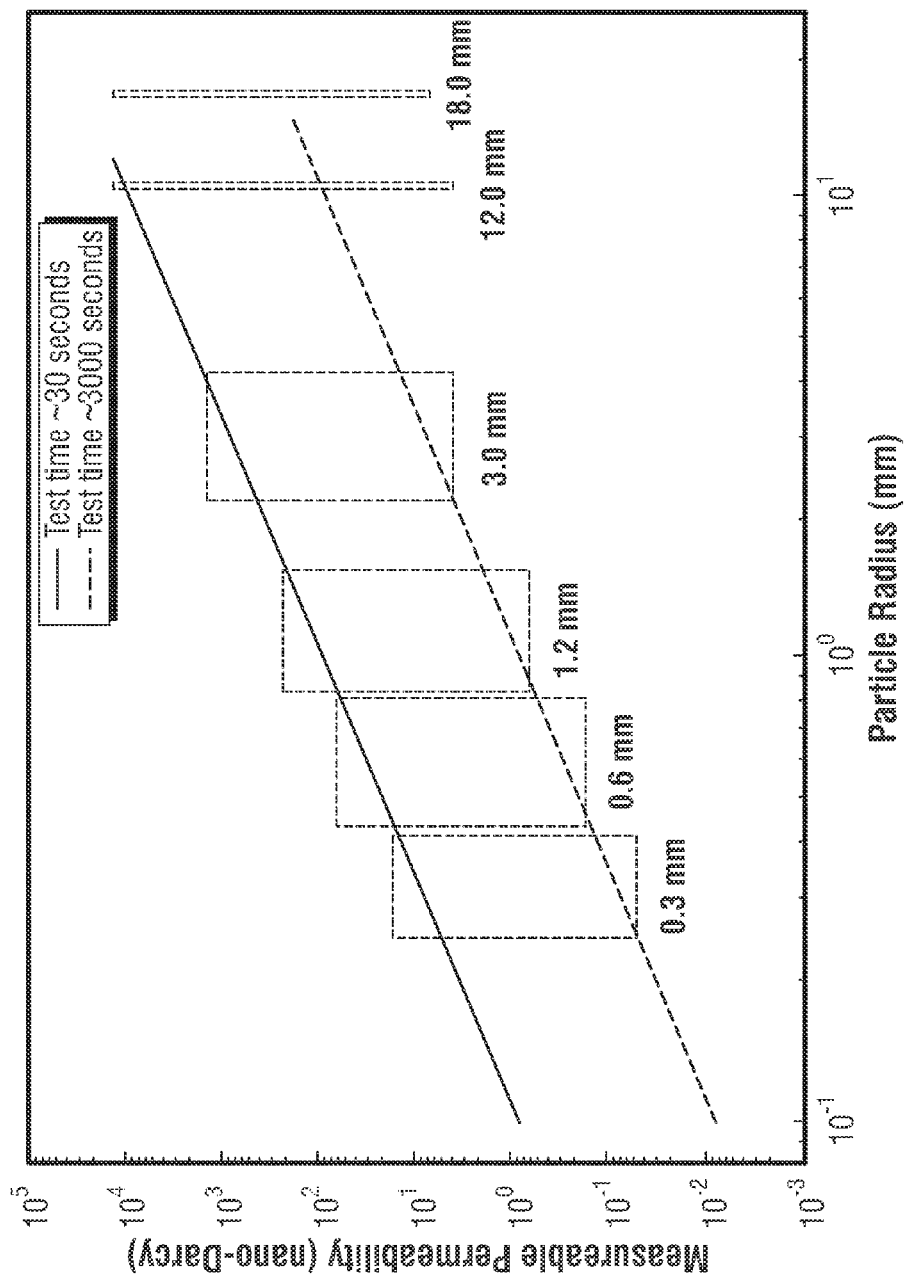
FIG. 1 is an illustrative plot of measureable permeability versus particle radius for narrow particle size distributions.

Permeability measurements of tight, microporous materials, and particularly in heterogeneous, low porosity, low permeability, unconventional reservoir rocks, can present challenges. For example, coring and core handling of heterogeneous rock samples can create extensive microcracking. The presence of microcracking directly affects the real permeability of the rock, and the lower the rock permeability, the larger the effect of the induced microcracking. This effect is most important for laminated, low permeability, organic-rich, mudstones, where the organic to mineral contact and the interfaces associated with the laminated fabric are weak contacts that are prone to part during unloading. This effect is less important for conventional, higher permeability rocks. Second, it can take considerable time to detect measureable flow through samples of standard size (e.g., 1 to 1.5 inch (25.4 to 38.1 mm) in diameter and 1 to 2 inch (25.4 to 50.8 mm) in length).

Two common approaches to minimize the effect of induced microcracking on permeability are: 1) apply high confinement stress to the sample plug to close the microcracks and reduce their influence on fluid flow; and 2) crush the rock into fragments that are smaller than the typical microcrack spacing. In this case, the microcracks become free surfaces in the fragments, and are effectively eliminated from the rock matrix. Crushing of the rock into fragments has the additional advantage of reducing the time to detect measurable flow during testing. For example, it can take considerable time to detect measureable flow through samples of standard size (e.g., 1 to 1.5 inch (25.4 to 38.1 mm) in diameter and 1 to 2 inch (25.4 to 50.8 mm) in length). Crushing of the rock into fragments also has the advantage that tests can be conducted on a broader distribution of samples, including fragments from cores, parted sections of core sections, parted rotary sidewall plugs, and potentially drill cuttings, given that the measurements do not depend on the mechanical integrity and quality of cylindrical samples.

Another challenge in measuring permeability in unconventional low permeability rocks is their heterogeneity. This means that they possess intrinsic variability in texture and composition that results from geologic processes of deposition and diagenesis, and this variability needs to be understood at various scales. As a result, these materials exhibit a broad distribution of properties and in particular a broad distribution of permeability. Following conventional measurements developed for homogeneous media, permeability measurements of unconventional low permeability rocks have been focused on the evaluation of a single representative value of this property. The meaning of the resulting permeability is ill defined. Because of the strong influence of high permeability on the measurements, the measured values do not represent the mean value of the permeability distribution, and are commonly more representative of the high end values. When measured in sample plugs, these high end values can be strongly biased by the presence of microcracks, high permeability laminations, and other types of features not representative of the rock matrix.

The heterogeneous nature of unconventional organic rich reservoirs, in particular, and reservoir rocks, in general, requires the acknowledgement and characterization of property distributions and not a homogenized single value representative of this distribution. This is the case for any property and in particular of permeability. However, full characterization of the permeability distribution over the entire range may be very time consuming and expensive. For practical reasons it is thus useful to introduce a workflow that allows characterization of both the averaged permeability of the bulk of the sample as well as the broad permeability distribution of the sample. Such workflow is described below in detail.

The measurement of average permeability is considered to be a characteristic conductivity index of the rock to be used for direct comparison between different rocks. The permeability distribution characterization is conducted on samples selected based on differences in their composition, texture, and average permeability which allows one to focus only on the rocks that are critical for the overall productivity of the reservoir.

For some materials and, in particular, unconventional reservoir rocks, it is important to consider two different types of sampling. The first one (which is referred to herein as a "manufactured sample") has a well-defined and controlled shape and requires material of sufficiently good quality to allow the manufacturing of samples with controlled shape (for example by drilling small cylindrical plugs or cutting small cubic samples with a diamond saw, out of a larger sample of whole core). The second one (which is referred to herein as a "fragmented sample") is made up of a fragmented medium without a well-defined and controlled shape, and thus relaxes the condition of material competence. Protocols for testing permeability distribution in fragmented samples and manufactured samples are described separately herein.

The permeability measurements described herein rely on pressure diffusion in porous samples and are limited by two clear experimental boundaries that define the permeability range that can be resolved by the measurements. The first experimental boundary is associated with the fastest pressure response related to diffusion of gas into fragments that can be measured, without being affected by initial gas flows at initiation of the test, gas expansion and compression, and related thermal effects. This high permeability limit defines the maximum measurable permeability and is difficult to extend because of the finite time of initial gas flow and because adiabatic heating and cooling of gas during the initial flow takes finite time to dissipate. Permeabilities higher than this limit cannot be detected by the equipment. The second experimental boundary is a low permeability limit defined by the maximum practical duration of the test and potential impact of unavoidable equipment leaks. Permeabilities equal to or lower than this limit cannot be detected by the equipment.

FIG. 1 shows the effect of particle size on the resolution of permeability by pressure decay systems. Specifically, FIG. 1 shows a plot of measureable permeability versus particle radius, for narrow particle size distributions. The characteristic diffusion time, which cannot be shorter or longer than certain limits, is controlled by the gas viscosity and compressibility, rock porosity, permeability, and the square of the rock fragment size. This means that the fragment size has the biggest impact on the measurable range of permeability. The upper and lower measurable permeability limits are shown in solid (upper limit) and dotted (lower limit) lines. The dependence of permeability resolution with particle size is given by the slopes of these lines.

During a single pressure decay test, an average permeability value resulting from a distribution of permeabilities that are inherently present in the rock sample is measured. If the range of particle sizes selected is larger than the representative volume of the rock, the permeability distribution will not change significantly with particle size. However, when the resolution of the measurements depends on the particle size, one can resolve different portions of the rock permeability distribution by varying the fragment sizes chosen. This disclosure employs this concept specifying the necessary procedures, including fragment size sampling and control strategies, required for characterization of permeability distribution in heterogeneous microporous samples.

Figure 2:
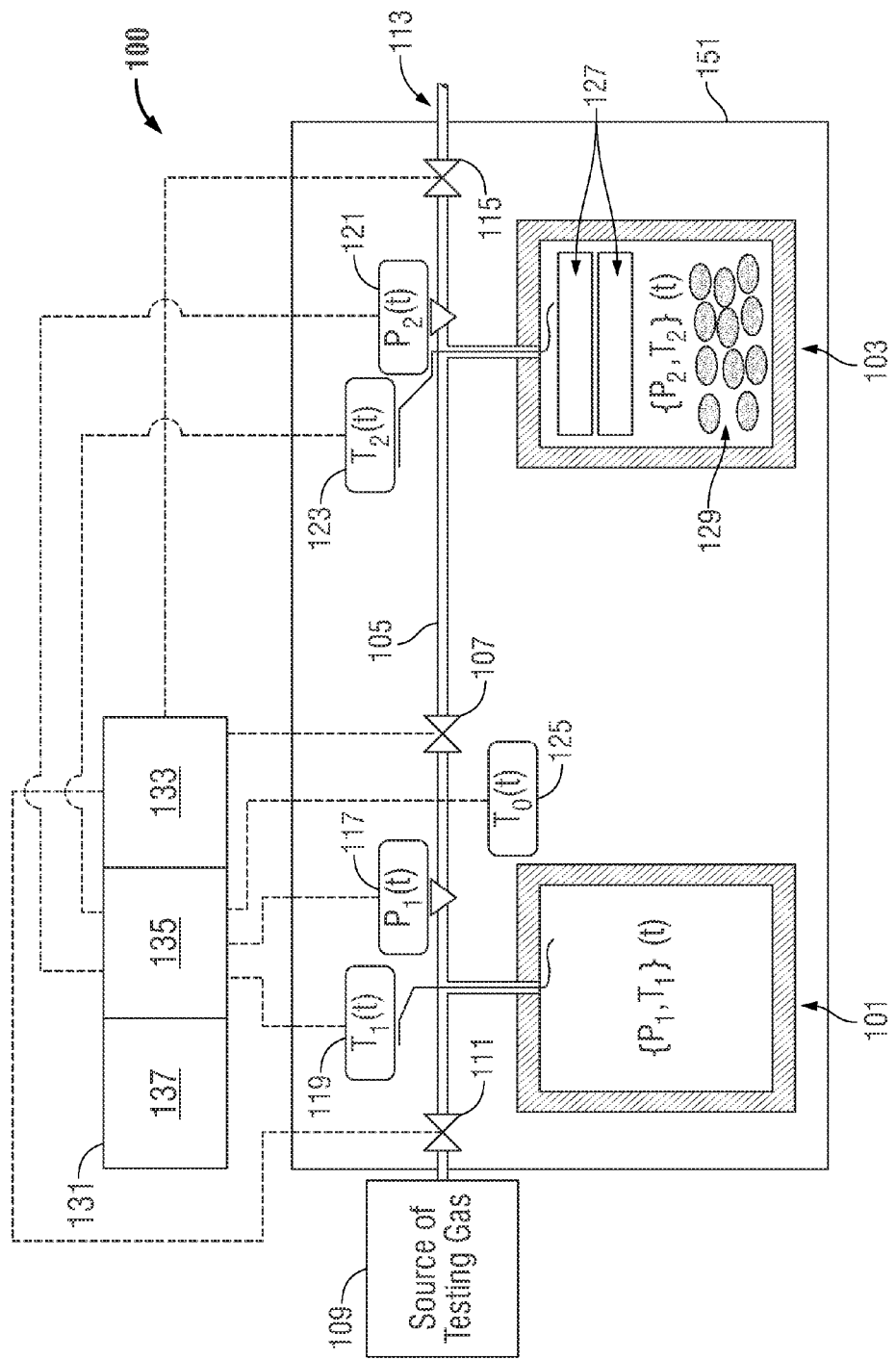
FIG. 2 is a schematic diagram of an isolated cell pressure decay testing apparatus in accordance with the present application.

FIG. 2 is a schematic diagram of an isolated cell pressure decay testing apparatus 100 in accordance with the present application. The apparatus 100 includes a housing 151 that houses a sealed cylindrical vessel referred to as the reference cell 101 and another sealed cylindrical vessel referred to as the sample cell 103. The volumes of both the reference cell 101 and the sample cell 103 are known. Tubing network 105 provides a closed fluid path between the internal volumes of the reference cell 101 and the sample cell 103. An electronically-controlled intermediate valve 107 is integral to the tubing network 105 and disposed between the reference cell 101 and the sample cell 103 as shown. The tubing network 105 also provides a closed fluid path between the reference cell 101 and a source of testing gas 109. An electronically-controlled intake valve 111 is integral to the tubing network 105 and disposed between the source of testing gas 109 and the reference cell 101 as shown. The source of testing gas 109 can employ a pressure regulator that releases the testing gas into the tubing network 105 at constant pressure. The tubing network 105 also provides a closed fluid path between the sample cell 103 and an exhaust port 113 that vents to atmosphere. An electronically-controlled exhaust valve 115 is integral to the tubing network 105 and disposed between the sample cell 103 and the exhaust port 113 as shown. The electronically-controlled valves 107, 111, 115 preferably have a fast response time that is on the order of tens of milliseconds (such as 10 milliseconds) or faster. The tubing network 105 can be implemented by solid piping made of low compressibility, non-corrosive, leak-proof material (such as stainless steel, various metal alloys, or any other existing or future materials satisfying the aforementioned requirements). The solid piping implementation can provide for flexibility in terms of replacing the components, such as switching the sizes and shapes of the reservoir and sample cells as necessary. Alternatively, the tubing network 105 can be implemented as a single piece manifold of low compressibility, non-corrosive, leak-proof material (such stainless steel, various metal alloys, or any other existing or future material satisfying the aforementioned requirements) which has output ports for all sensors, valves, and cells. The manifold implementation can provide a reduced risk of leaks.

A pressure sensor 117 is fluidly coupled to the reference cell 101 and is configured to measure pressure of the reference cell 101 over time. A temperature sensor 119 (such as a thermocouple) is fluidly coupled to the reference cell 101 and is configured to measure temperature of the reference cell 101 over time. The pressure sensor 117 and the temperature sensor 119 preferably provide a fast response time on the order of tens of milliseconds (such as 10 milliseconds) or less.

A pressure sensor 121 is fluidly coupled to the sample cell 103 and is configured to measure pressure of the sample cell 103 over time. A temperature sensor 123 (such as a thermocouple) is fluidly coupled to the sample cell 103 and is configured to measure temperature of the sample cell 103 over time. The pressure sensor 121 and the temperature sensor 123 preferably provide a fast response time on the order of tens of milliseconds (such as 10 milliseconds) or less.

An additional temperature sensor 125 (such as a thermocouple) is positioned at or near the center of the housing 151 and is configured to measure the average temperature of the system. The housing 151 encloses all the piping, valves, sensors, and the two cells, and can provide thermal insulation to the system and reduce temperature variations caused by external sources.

The electronically-controlled valves 107, 111, 115, the pressure sensors 117, 121 and the temperature sensors 119, 123, 125 are electrically coupled to a data processing system 131. The data processing system 131 includes a valve control and interface module 133 that is configured to communicate electronic signals to the valves 107, 111, 115 for control over the operation of the valves 107, 111, 115 during operation of the system as described herein. The data processing system 131 also includes a data acquisition module 135 that samples the electrical signals output by the pressure sensors 117, 121 and the temperature sensors 119, 123, 125 over time and stores electronic data that represents such output signals. The data acquisition module 135 can perform analog-to-digital conversion of the signals output by the pressure sensors 117, 121 and the temperature sensors 119, 123, 125 as needed. Alternatively, such analog-to-digital conversion can be performed by the pressure sensors 117, 121 and/or the temperature sensors 119, 123, 125 themselves. The data processing system 131 also includes a data analysis module 137 that processes data representing the output of the pressure sensors 117, 121 and the temperature sensors 119, 123, 125 to characterize certain properties of the porous material under test as described herein.

During operation, the sample cell 103 can be loaded with a set of steel billets 127 of known volume along with a porous material under test (i.e., a porous sample) 129. The sample cell 103 can be equipped with a sliding lid, which can be moved by high-pressure air or other suitable means under control of a manual switch in order to open or close the sliding lid to facilitate the loading and unloading of the billets 127 and the sample 129 into the interior space of the sample cell 103. Alternatively to the sliding lid, the sample cell 103 can be put on a moving stand, which is moved up or down by a manual switch and pushed against a fixed lid or flat manifold surface at the top position to close the cell. The sealing mechanism between the sample cell and the sliding lid or between the sample cell and the manifold has to satisfy the following conditions: insignificant changes in the volume of the sample cell during multiple open/close cycles and due to pressure changes in the sample cell; sufficient flexibility to isolate the sample cell from the atmosphere; no leakage of the testing gas through the seal. Such seal can be implemented, for example, using commercially available O-rings with small cross-section diameter (3 mm or less cross-section diameter; ring diameter can be varied, typically in the order of 30 mm) made of non-porous leak-tight rubber or using a custom-designed polytetrafluoroethylene sealing post attached to the sample cell. Other existing or future materials satisfying the aforementioned requirement can be used in manufacturing of the sealing post.

In one embodiment, the design of the tubing network 105 and the cells 101, 103 incorporates optimization of their thermal properties, which satisfies the following requirements:

large total thermal capacity of the tubing network 105 and the cells 101, 103 compared to thermal capacity of test gas and the sample together and at all stages of the test;

high thermal conductivity between the testing gas and the walls of the cells 101, 103, which provides fast temperature equilibration in the system.

Moreover, the reference cell 101, the sample cell 103, and the tubing network 105 must be sufficiently rigid in order to ensure negligible variations of system volumes due to gas compression/expansion.

The testing apparatus of FIG. 2 can be configured to measure porosity and permeability of a sample at a predetermined elevated pressure as follows. Initially, the valve control and interface module 133 controls the intermediate valve 107 to assume a closed position in order to isolate the reference cell 101 from the sample cell 103, and the sample cell 103 is loaded with the rock sample and closed at atmospheric pressure. The intake valve 111 is controlled to assume an open position to fluidly couple the source of testing gas 109 to the reference cell 101 in order to fill the reference cell 101 with testing gas at the predetermined elevated pressure of the test. After filling the reference cell 101 with testing gas, the valve control and interface module 133 controls the intake valve 111 to assume a closed position to isolate the reference cell 101. Next, the valve control and interface module 133 controls the intermediate valve 107 to assume an open position for a very short period of time (typically on the order of tens or hundreds of milliseconds), which is sufficient to flow substantial amounts of the testing gas from the reference cell 101 into the sample cell 103. During this flow period, the pressure in the reference cell 101 falls rapidly, due to gas expansion from the reference cell 101 into the free volume of the sample cell 103. The time interval that the intermediate valve 107 remains open to allow flow of testing gas from the reference cell 101 into the sample cell 103 must satisfy several conditions. First, it has to be long enough to create a substantial pressure increase in the sample cell 103. Second, it has to be short enough to minimize mixing of gas inflow into the sample cell 103 (from the tubular network 105) with respect to gas diffusion into the rock sample. Third, it has to be highly consistent to ensure repeatable measurements from test to test. To satisfy these conditions, manual valve control is inadequate. Instead, programmable control of the operation of the electronically-controlled valves as a function of time (or other conditions) is required.

Then, the valve control and interface module 133 controls the intermediate valve 107 to assume a closed position that isolates both the reference cell 101 and the sample cell 103. After the intermediate valve 107 is closed, the gas pressure in the sample cell 103 begins to decrease at a slower rate due to diffusion of gas into the porous sample. These operations are referred to as the pressure decay stage and continue for a time period $T_{decay}$.

Next, the valve control and interface module 133 controls the exhaust valve 115 to assume an open position that fluidly couples the sample cell 103 to the exhaust port 113 for a short period of time in order to reduce the pressure in the sample cell 103 to atmospheric. The time interval that exhaust valve 115 remains open has to be sufficiently long to drop pressure completely and at the same time sufficiently short to prevent diffusion and mixing of air with the testing gas in the sample cell. The optimal duration of the exhaust cycle has to be determined for particular equipment design and testing gas. As a guideline, the exhaust cycle has to provide final pressure in the empty sample cell within 1 psi (0.07 kg/square cm) of atmospheric. In case of helium used as the testing gas and ⅛ inch (3.2 mm) piping, the typical exhaust time can be around 1-4 seconds.

Next, the valve control and interface module 133 controls the exhaust valve 115 to assume a closed position that isolates the sample cell 103. After the exhaust valve 115 is closed, the gas pressure in the sample cell 103 increases as gas diffuses out of the porous sample 129 into the interior space of sample cell 103. These operations are referred to as the degassing stage and continue for a time period $T_{degas}$.

During the testing process (particularly during the time period $T_{decay}$ of the pressure decay stage and during the time period $T_{degas}$ of the degassing stage), the data acquisition module 135 cooperates with the pressure sensor 117 and the temperature sensor 119 to measure and record the temperature and pressure of the reference cell 101 over time. The data acquisition module 135 also cooperates with the pressure sensor 121 and the temperature sensor 123 to measure and record the temperature and pressure of the sample cell 103 over time. Furthermore, the data acquisition module 135 cooperates with the temperature sensor 125 to measure and record the average temperature of the system over time.

The data analysis module 137 processes data representing the output of the pressure sensors 117, 121 and the temperature sensors 119, 123, 125 to characterize permeability and porosity of the porous material under test. Such analysis involves matching data that represents the transient pressure of the sample cell 103 over time (particularly during the time period $T_{decay}$ of the pressure decay stage and during the time period $T_{degas}$ of the degassing stage) to pressure curves (i.e., pressure data) generated by a computational model where the pressure curves are related to materials of known porosity and permeability characteristics. The permeability and porosity of the porous material under test can be derived from the porosity and permeability characteristics of the material related to the best-matching pressure curve.

The isolated configuration of the sample cell 103 during both the pressure decay stage and the degassing stage has multiple advantages. First, the dead volume (cell volume minus volume of particles) is decreased by a factor of approximately three or more. This increases the observed pressure variation due to gas diffusion into the pore space, and also increases the accuracy and low limit of porosity and permeability measurements. Second, the thermal mass of gas in the cell, compared to the thermal mass of the cell, is reduced. As a consequence, the temperature variations in the cell are also reduced. Third, the observed pressure variations due to thermal adiabatic effects in the gas are reduced compared to pressure variations due to gas diffusion. This is so because the reference cell, which has a larger relative thermal mass of gas than the sample cell and larger temperature fluctuations, is isolated from the sample cell. Finally, the single cell system is simple to model numerically and analytically.

In one embodiment, the operation of the valve control and interface module 133 is implemented by a testing script specified as an ASCII text file. The testing script is loaded and executed by the valve control and interface module 133 to perform automatic control operations as specified by the testing script. An exemplary testing script that measures porosity and permeability of a porous sample at a predetermined elevated pressure includes the following steps. It is assumed that the sample cell 103 is loaded with the rock sample.

First, the test script controls the intermediate valve 107 to assume a closed position in order to isolate the reference cell 101 from the sample cell 103, and the intake valve 111 is controlled to assume an open configuration to fluidly couple the source of testing gas 109 to the reference cell 101 in order to fill the reference cell 101 with testing gas at an initial elevated pressure (for example, at approximately 2 atmospheres absolute pressure or higher).

Next, there are a number (for example, 3-4) of quick flushing cycles to replace air in the dead volume by the testing gas. Each flushing cycle consists of flowing the testing gas from the reference cell 101 to the sample cell 103, by opening and then closing the intermediate valve 107, and releasing the gas mixture through the exhaust port 113 to atmosphere by opening and then closing the exhaust valve 115. After several flushing cycles, the relative concentration of air and the testing gas in the dead volume becomes negligible (apart from the gas in the pore space with limited permeability), and the pressure in the isolated sample cell 103 is near atmospheric pressure.

Next, the test script controls the intermediate valve 107 to assume a closed position in order to isolate the reference cell 101 from the sample cell 103, and the intake valve 111 is controlled to assume an open position to fluidly couple the source of testing gas 109 to the reference cell 101 in order to fill the reference cell 101 with testing gas at the predetermined elevated pressure of the test. After filling the reference cell 101 with testing gas, the intake valve 111 is controlled to assume a closed position to isolate the reference cell 101.

Next, the test script performs a wait operation for a waiting time of approximately 200-400 seconds in order to allow the temperature in the reference cell 101 to equilibrate with the ambient temperature and the sample cell temperature 103. Equilibration is necessary to make accurate measurements of the initial pressures in the cells.

After expiration of the waiting time, the test script controls the intermediate valve 107 to assume an open position for a very short period of time (i.e., 0.1 seconds, which is sufficient to flow substantial amounts of the testing gas from the reference cell 101 into the sample cell 103. During this flow period, the pressure in the reference cell 101 falls rapidly, due to gas expansion from the reference cell 101 into the free volume of the sample cell 103.

Next, the test script controls the intermediate valve 107 to assume a closed position that isolates both the reference cell 101 and the sample cell 103. After the intermediate valve 107 is closed, the gas pressure in the sample cell 103 begins to decrease at a slower rate due to diffusion of gas into the porous sample. These operations are referred to as the pressure decay stage and continue for the time period $T_{decay}$.

Next, the test script controls the exhaust valve 115 to assume an open configuration that fluidly couples the sample cell 103 to the exhaust port 113 at atmosphere for a short period of time (e.g., 1-4 seconds) in order to drop the pressure of the sample cell 103 to atmospheric.

Next, the test script controls the exhaust valve 115 to assume a closed position that isolates the sample cell 103. After the exhaust valve 115 is closed, the gas pressure in the sample cell 103 increases as gas diffuses out of the porous sample into the interior space of sample cell 103. These operations are referred to as the degassing stage and continue for the time period $T_{degas}$.

At the beginning of the testing process (when the test script is started), the test script triggers the data acquisition module 135 to cooperate with the pressure sensor 117 and the temperature sensor 119 to measure and record the temperature and pressure of the reference cell 101 over time. The test script also triggers the data acquisition module 135 to cooperate with the pressure sensor 121 and the temperature sensor 123 to measure and record the temperature and pressure of the sample cell 103 over time. Furthermore, the test script triggers the data acquisition module 135 to cooperate with the temperature sensor 125 to measure and record the average temperature of the system over time.

The optimal values of the time period $T_{decay}$ of the pressure decay stage and the time period $T_{degas}$ of the degassing stage depends on a-priori knowledge of the permeability of the tested material, and this is determined by trial and error. Alternatively, a convenient test time $T_{test}$ that is equated to the time period $T_{decay}$ as well as to the time period $T_{degas}$ can be set, and the maximum size of the fragments can be reduced using an iterative procedure. For crushed samples with particle diameter less than 3 mm, the typical time for time period $T_{decay}$ of the pressure decay stage and the time period $T_{degas}$ of the degassing stage are both equated to the same time period between 300 and 1500 seconds.

This procedure can be repeated multiple times (typically 2-3 times, any number of repeats is possible) to evaluate test consistency and repeatability, which can be affected, for example, by temperature fluctuations introduced during the loading of the sample cell 103, and by the presence of the non-test gas (predominantly air, with possible contribution of desorbed gases from the internal surface area of the microporous material, such as water vapor, hydrocarbons, etc.) in the pore space of the sample. Note that quick flushing of the sample cell with the testing gas, as described earlier, usually cannot fill the pore space of the sample with the testing gas, because of the low permeability. For this reason, the first test can be conducted for pore space cleaning. In this case, it may not yield a reliable estimate of sample properties, and thus can be excluded from the analysis.

Figure 3:
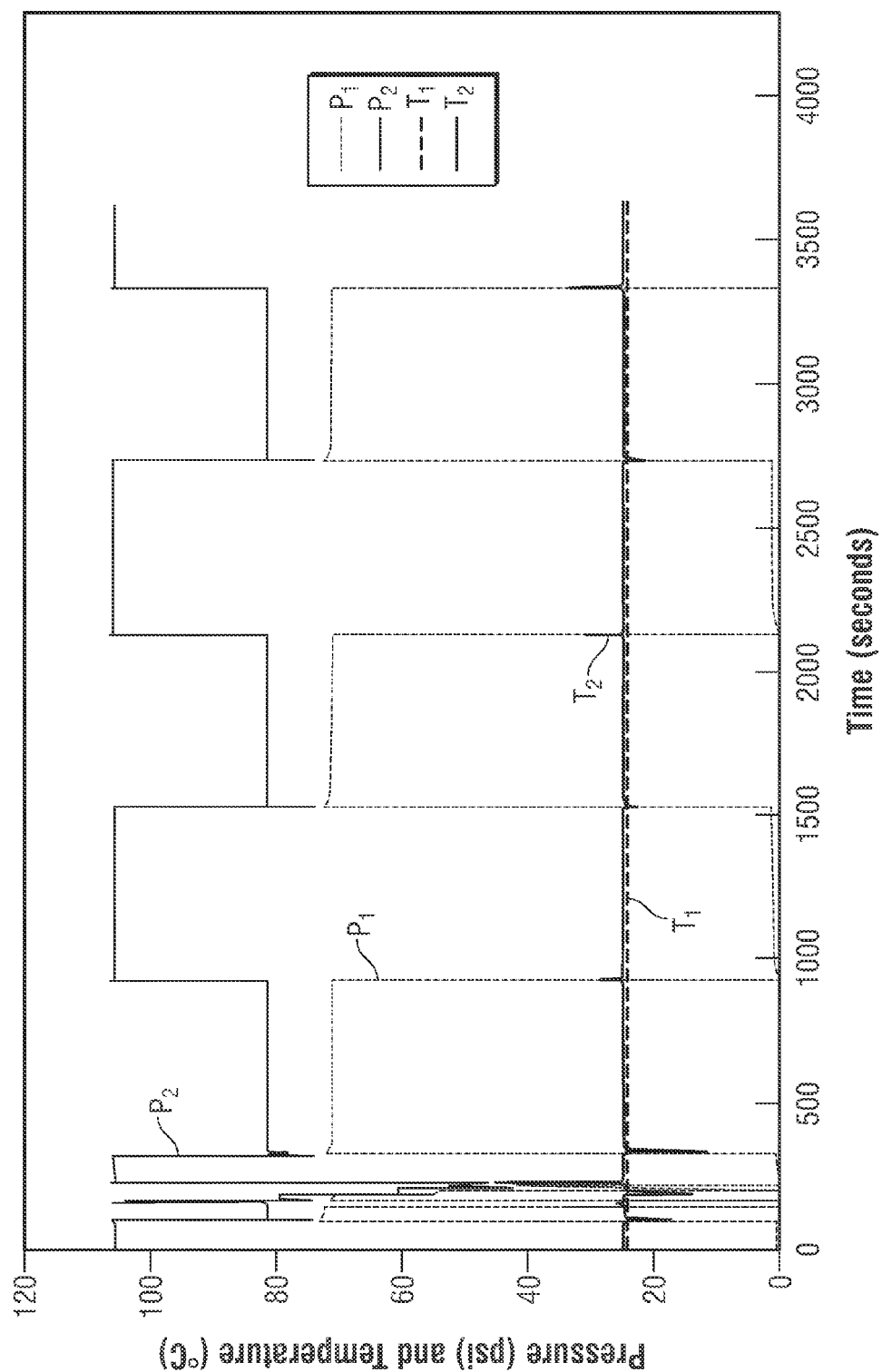
FIG. 3 is a plot of exemplary pressures and temperatures recorded during the operations of a test script carried out by the apparatus of FIG. 2.

FIG. 3 presents an example of pressures and temperatures recorded during the operations of the test script. It includes one flushing stage and three repeats of the pressure decay stage and degassing stage. The minimum amount of material required for the testing can be varied by proper selection of sample and reference cell dimensions, geometries, and materials. Practical and convenient for core testing purposes amounts of material are found to be in the range of 2 to 25 cc bulk volume.

The testing apparatus of FIG. 2 can be calibrated to allow the apparatus to generate physically sensible, consistent, and accurate measurements. Calibration of the apparatus can be accomplished after the apparatus is completely assembled and not on a component by component basis to ensure that the response of the apparatus as a whole meets the requirements for consistent and accurate measurements.

Characterizing Valve Times and Connectivity Between Volumes.

The calibration operations can involve estimating the valve times and connectivity between the volumes separated by the valves. Such information is useful for specifying test scripts that provide desired changes in pressures. In one embodiment, the minimum valve response time is identified as the shortest duration between sequential 'valve open' and 'valve close' commands of the test script, which repeatably produces some change in pressure in the volumes separated by the valves (provided these volumes had some pressure differential before valve cycling). Connectivity is defined based on the assumption that pressure differential between the volumes can be approximated as exponentially decreasing with time, while the valve is open:

$$\Delta P = \Delta P_o e^{-\frac{t-v_i}{\delta_i}}, \qquad (1)$$

where t is the time as defined by the test script between the valve opening and closing, i is the index of the valve (for example, 1 for the intake valve 111, 2 for the intermediate valve 107, and 3 for the exhaust valve 115), $v_i$ is the minimum valve response time for the respective valve of index i, $\delta_i$ is a valve connectivity parameter for the respective valve of index i, and $\Delta P_0$ and $\Delta P$ are the initial and final pressure differentials between the volumes separated by the respective valve.

Before cycling of any given one of the valves 111, 107, 115, the pressure on both sides of the given valve is known for deriving $\Delta P_0$. Specifically, the pressure sensors 117 and 121 provide pressure on the two sides of the intermediate valve 107. The pressure settings of the testing gas source 109 and the pressure sensor 117 provide pressure on the two sides of the intake valve 111. The pressure sensor 121 and the known atmospheric pressure at the exhaust port 113 provide pressure on both sides of the exhaust valve 115. After cycling the given valve, the change of the pressure differential between the volumes separated by the given valve can be measured for deriving $\Delta P$. Specifically, the pressure sensors 117 and 121 provide pressure measurements that characterize the pressure differential between the two volumes separated by the intermediate valve 107. The pressure settings of the testing gas source 109 and the pressure measurement of the pressure sensor 117 characterizes the pressure differential between the two volumes separated by the intake valve 111. The pressure measurement of the pressure sensor 121 and the known atmospheric pressure at the exhaust port 113 characterizes the pressure differential between the two volumes separated by the exhaust valve 115. The minimum valve response times $v_i$ and connectivity parameters $\delta_i$ for each given valve are estimated by running multiple test scripts that create initial pressure differential across each valve, cycling valves for different durations and then comparing drop in pressure differential after each valve cycle. Estimation of connectivity parameters and response times is done with an empty sample cell, not containing any billets or samples. In case of a high quality fast valve, which assumes large driving force on the valve repositioning compared to forces due to internal pressure in the system, the drop in pressure differential is very well approximated by an exponential decrease with time, which is independent of the absolute values of pressure in the system. In this case, $\delta_i$ and $v_i$ are constants. In case of the relatively low driving force on the valves, both valve response times and connectivity parameters may need to be estimated as functions of absolute pressures on both sides of the valve. This is done by running scripts and analyzing pressure records creating various pressure differentials with different combinations of absolute pressures across valves.

Note that connectivity parameters $\delta_i$ for each valve are determined for an empty sample cell 103 that has volume $V_2$ and an empty reference cell 101 that has volume $V_1$. The actual rate of pressure differential decline with an open valve can be different if additional volume, e.g. billets 127, is loaded into the sample cell 103. The pressure decline rate through intake valve 111 is not changed, because nothing is loaded into the reference cell 101. Denoting by A the additional volume placed into the sample cell 103, the decline of the pressure differential through the exhaust valve 115 can be estimated as:

$$\Delta P = \Delta P_o e^{-\frac{t-v_3}{\delta_3} \cdot \frac{V_2}{V_2-A}}. \tag{2}$$

Decline of the pressure differential through the intermediate valve 107 can be estimated as:

$$\Delta P = \Delta P_o e^{-\frac{t-v_2}{\delta_2} \cdot \frac{V_2(V_1+V_2-A)}{(V_1+V_2)(V_2-A)}} \text{ for } t > v_1. \tag{3}$$

With the pressure of the gas source denoted $P_s$, the initial pressures in the reference cell 101 and in the sample cell 103 denoted as $P_{10}$ and $P_{20}$ respectively, and the atmospheric pressure denoted $P_{atm}$, the change of pressure in the reference cell 101 with time after the intake valve 111 is open for $t > v_1$, and other valves are maintained closed, can be estimated by:

$$P_1 = P_s - (P_s - P_{10})e^{-\frac{t-v_1}{\delta_1}}. \tag{4}$$

In the case when the intermediate valve 107 is open for time $t > v_2$, while other valves are maintained closed, the pressures in the reference cell 101 and sample cell 103 can be estimated by:

$$P_1 = \frac{P_{10}V_1 + P_{20}V_2}{V_1+V_2} + \frac{V_2}{V_1+V_2}(P_{10}-P_{20})e^{-\frac{t-v_2}{\delta_2} \cdot \frac{V_2(V_1+V_2-A)}{(V_1+V_2)(V_2-A)}}, \text{ and} \tag{5A}$$

$$P_2 = \frac{P_{10}V_1 + P_{20}V_2}{V_1+V_2} - \frac{V_1}{V_1+V_2}(P_{10}-P_{20})e^{-\frac{t-v_2}{\delta_2} \cdot \frac{V_2(V_1+V_2-A)}{(V_1+V_2)(V_2-A)}}. \tag{5B}$$

In the case when the exhaust valve 115 is open for time $t > v_3$, while other valves are maintained closed, the pressure in the sample cell 103 can be estimated by:

$$P_2 = P_{atm} + (P_{20} - P_{atm})e^{-\frac{t-v_3}{\delta_3} \cdot \frac{V_2}{V_2-A}}. \tag{6}$$

Consider the case, when the initial position of the valves 111-107-115 is closed-open-closed, and the initial pressure in cells 101 and 103 is $P_{10}=P_{20}$. After the exhaust valve 115 is open for time $t > v_3$ while the cells are connected, the pressure in the cells 101 and 103 can be estimated by:

$$P_1 = P_2 = P_{atm} + (P_{20} - P_{atm})e^{-\frac{t-v_3}{\delta_2+\delta_3} \cdot \frac{V_1+V_2}{V_1+V_2-A}}. \tag{7}$$

These relationships allow for prediction of the final resulting pressures in both reference cell 101 and sample cell 103 for all possible initial pressure conditions as a function of valve open-close cycle duration and for all practical scenarios of valve cycling. In turn, based on the initial pressure conditions and desired final pressure state, which should agree with the basic laws of physics such as mass conservation (already embedded in the equations) and directionality of flow (working pressure range is always $P_s \geq P_1 \geq P_2 \geq P_{atm}$), these equations provide the estimation of the valve cycle duration required to reach the desired pressure state. By combining various valve cycle sequences it is always possible to set cell pressures to any arbitrary levels within the working pressure range starting from any initial pressure state. An example of a universal sequence can be described as follows: i) refill cells 101 and 103 to the highest pressure by setting valves to open-open-closed and then closed-open-closed; ii) set pressure in both cells to a desired value $P_2$ by setting valves to closed-open-open and then closed-closed-closed, where the duration of the cycle is determined by $P_2$ and cell volumes; iii) set pressure in reference cell 101 to a desired value $P_1$ by setting valves to open-closed-closed and then closed-closed-closed, where the duration of the cycle is determined by $P_1$. For specific initial pressure conditions and specific pressure cycling operations the testing script can be configured accordingly. The ability to estimate the optimal valve timings to reach desired pressure states from any previous state allows the development of testing scripts that need to cycle through certain pressure combinations in a certain order, such as calibration scripts and scripts for pressure decay testing at different pressures. These scripts are described in the following sections.

Note that the developed relationships for predicting pressure evolution due to valve cycling are not meant to predict exact pressure values after large number of sequential valve sequences of various types. There is intrinsic scatter in the repeatability of valve operation and observed pressure changes resulting from the same cycle durations imposed by valve control and interface module 133. The error in pressure prediction after several sequential pressure changes may grow. These relationships are meant to be used to predict the initial estimate of valve timing to reach all desired pressure combinations in the developed testing script; then the developed draft of the testing script is run to record actual pressure levels realized and valve times are adjusted to reach desired pressure levels more precisely.

Compensation of Differences in Pressure Sensor Measurements.

The calibration operations can compensate for differences in the pressure sensor measurements made by the pressure sensors 117 and 121 at one or more applied pressures. Although commercially available pressure sensors are factory-calibrated, there still may be a measureable difference between pressure readings from the pressure sensors 117 and 121 at one or more applied pressures, which can and should be compensated for. Possible causes for the difference can be individual variations in the hardware and firmware of the pressure sensors within the factory tolerance and any differences in operational conditions and in signal processing between the two pressure sensors 117 and 121, while the applied pressure is converted to an electric signal, digitized, and recorded by the data acquisition module 135. The calibration operations can involve estimating the differences in pressure sensor measurements made by the pressure sensors 117 and 121 at one or more applied pressures by running a specifically developed test script, which records the pressure measurements from both pressure sensors 117 and 121 while the pressure sensors are connected to the same applied pressure (i.e., the intermediate valve 107 is open). The test script can vary the applied pressure at the pressure sensors 117 and 121 over the entire working range of the apparatus. For example, at the beginning of the test script, both the reference cell 101 and the sample cell 103 can be filled with testing gas at the highest value in the working range of the apparatus (which can be defined by the pressure regulator at testing gas source 109). Then, the intermediate valve 107 is kept open and the exhaust valve 115 is periodically opened for short periods of time and then closed, to stepwise decrease the pressure in both the reference cell 101 and the sample cell 103 by a controlled amount. The valve opening times of the exhaust valve 115 can be selected based on the minimum valve response time $v_i$ and the connectivity parameters $\delta_i$ of the exhaust valve as described above in order to create a number of pressure levels (for example, nine to eleven) regularly distributed within the working pressure range of the apparatus. Because of the thermal effects, the wait time between each pressure change should be sufficiently long to ensure perfect thermal equilibration of the apparatus, which can be on the order of 10 to 20 minutes.

The result of this procedure can be presented as two pressures as a function of average pressure:

$$P_1^i(P_{av}^i), P_2^i(P_{av}^i), P_{av}^i = (P_1^i + P_2^i)/2. \quad (8)$$

where $P_1^i$ is the pressure measured by the pressure sensor 117 at the pressure level i of the working pressure range of the apparatus, and $P_2^i$ is the pressure measured by the pressure sensor 121 at the pressure level i of the working pressure range of the apparatus.

The systematic difference between the two transducers, which is consistently repeatable through multiple tests, can be approximated by a polynomial function of the average pressure as follows:

$$\Delta P_{12}(P_{av}) = P_1(P_{av}) - P_2(P_{av}) = A_0 + A_1 P_{av} + A_2 P_{av}^2 + \quad (9)$$

Any other analytical function can be used to approximate systematic pressure difference, if it would be found more suitable than the polynomial function.

The compensation of the pressure difference can be implemented as a subtraction of approximated pressure difference from each recorded pressure:

$$P_1^{corr} = P_1 - \frac{1}{2} \frac{\Delta P_{12}(P_1)}{1 + \frac{1}{2}\Delta P'_{12}(P_1)}, \quad (10)$$

$$P_2^{corr} = P_2 + \frac{1}{2} \frac{\Delta P_{12}(P_2)}{1 - \frac{1}{2}\Delta P'_{12}(P_2)},$$

where $\Delta P'_{12}$ is the first-order derivative of the analytical function selected to approximate the difference between the uncompensated pressure readings, which can be defined by, for example, Eq. (9).

Note, that after the compensation of the systematic difference in the two transducers, there may be some random variability in the readings of the connected pressure sensors, which is attributable to random noise intrinsic to the measurement system. The amplitude of this noise can be estimated.

Zeroing Pressure.

After the difference between the two pressure sensors is compensated, there still may be a difference between the pressure reading recorded from the transducers and actual absolute pressure. This difference is minimized by comparing the measurements of atmospheric pressure by sensors 117 and 121 (valves 111-107-115 are in the closed-open-open position) against the reference pressure measurement (from e.g. dead-weight tester, certified barometer or any other trustworthy source of reference atmospheric pressure) and then subtracting the recorded difference, denoted $\Delta P_a$, from the raw reading from pressure transducers. It is recommended to repeat measurements of the shift from the reference atmospheric pressure several times, at different levels of atmospheric pressure, which is changing. In this case, the absolute shift, $\Delta P_a$, is assigned the mean of multiple measurements. The full correction that includes pressure difference compensation and absolute pressure shift is specified by $$P_1^{corr} = P_1 - \frac{1}{2} \frac{\Delta P_{12}(P_1)}{1 + \frac{1}{2}\Delta P'_{12}(P_1)} + \Delta P_a, \quad (11)$$

$$P_2^{corr} = P_2 + \frac{1}{2} \frac{\Delta P_{12}(P_2)}{1 - \frac{1}{2}\Delta P'_{12}(P_2)} + \Delta P_a.$$

The compensation of pressure difference can be carried out at one or more average system temperatures (the temperature inside the housing 151) in order to compensate for relatively small and/or infrequent thermal effects in the pressure sensor measurements made by the pressure sensors 117 and 121. For example, in the event that the daily variation of the average system temperature inside the housing 151 is less than 1° C., and this temperature is constant from day to day, the compensation of pressure difference done at a single average system temperature may be sufficient. Alternatively, where there is a large but infrequent variation in the average system temperature (e.g., from winter to summer seasons), the compensation of pressure difference can be repeated as necessary.

Compensation of Relatively Large and/or Frequent Thermal Effects in Pressure Sensor Measurements.

The calibration operations can also compensate for relatively large and/or frequent thermal effects in the pressure sensor measurements made by the pressure sensors 117 and 121 at one or more applied pressures. Even though high accuracy pressure sensors include built-in temperature compensation, which is factory calibrated individually on each sensor, this temperature compensation often behaves slightly different on each sensor. As a result, there may be an additional systematic change in the difference of the pressure sensor measurements of the pressure sensors 117 and 121 as a function of average system temperature. If there are relatively large and/or more frequent changes in average system temperature of the apparatus, temperature dependent compensation for the pressure difference is introduced. In this case, the average system temperature of the apparatus as measured by the temperature sensor 125 is set to a list of specific values within the expected working range of temperatures. This can be accomplished by cooling or heating the apparatus or room in which the apparatus is located. Then, estimation of pressure difference for average temperatures and average pressures is done using the same scripts as described above. Typically, a function (polynomial or other) can be used to approximate the pressure difference at each average system temperature, but now the coefficients in this function and, possibly, zero shift, become temperature dependent and have to be tabulated accordingly. In this case, the pressure corrections corresponding to the particular average system temperature measured by the temperature sensor 125 for a particular test are used to derive the pressure measurements of the pressure sensors 117 and 121 as part of the test.

Precise Estimation of System Volumes and Compensation of Non-Linearity of Pressure Sensors.

The calibration operations can also calculate the exact volumes of the reference cell 101 and the sample cell 103 and identify and compensate for various inconsistencies in the pressure sensor measurements made by the pressure sensors 117 and 121 stemming from non-linearity of the pressure sensors 117 and 121. These operations are performed after compensating for pressure difference as described above.

Consider a test script where there is some initial difference between the pressure in the reference cell 101, labeled $P_{1-time0}$, and the pressure in the sample cell 103, labeled $P_{2-time0}$. Then, the intermediate valve 107 is opened for some short period of time to flow some amount of gas and subsequently closed. The final pressure in the reference cell 101 stabilizes at $P_{1-time-end}$, and the final pressure in the sample cell 103 stabilizes at $P_{2-time-end}$. The stabilization time is selected long enough to dissipate adiabatic temperature changes in gas and ensure isothermal process, which can be on the order of 10 to 20 minutes. Mass balance requires that:

$$(P_{1-time0}*V_1)+(P_{2-time0}*V_2)=(P_{1-time-end}*V_1)+(P_{2-time-end}*V_2), \quad (12)$$

where $V_1$ and $V_2$ are volumes of the reference cell 101 and the sample cell 103, respectively.

The pressure sequence as described can be used to calculate the volume ratio $$k_V = \frac{V_2}{V_1}$$

by the following equation:

$$k_V = \frac{V_2}{V_1} = \frac{(P_{1-time0} - P_{1-time-end})}{(P_{2-time-end} - P_{2-time0})}. \quad (13)$$

Note that here it is assumed that the test is normally recorded with the sample cell 103 containing only billets 127 and not containing a porous sample 129. If there is a porous sample in the sample cell 103, calculation of the volume ratio as described is still valid, but stabilization time may need to be increased to ensure complete diffusion of gas into the porous sample.

In the ideal scenario, the volume ratios $k_V$ measured at all possible initial pressure combinations within the working pressure range should be identical. They also should be consistent when various combinations of known volume billets are used. In addition, the repeatedly measured $k_V$ with the same billet sets should be identical after multiple open/close cycles of the sample cell 103 confirming that re-sealing of the sample cell 103 consistently creates the same sample cell volume. Probing of all possible combinations of two initial pressures uniformly and with sufficient density distributed within the working pressure range can be impractical due to the large number of combinations.

Figure 12B:
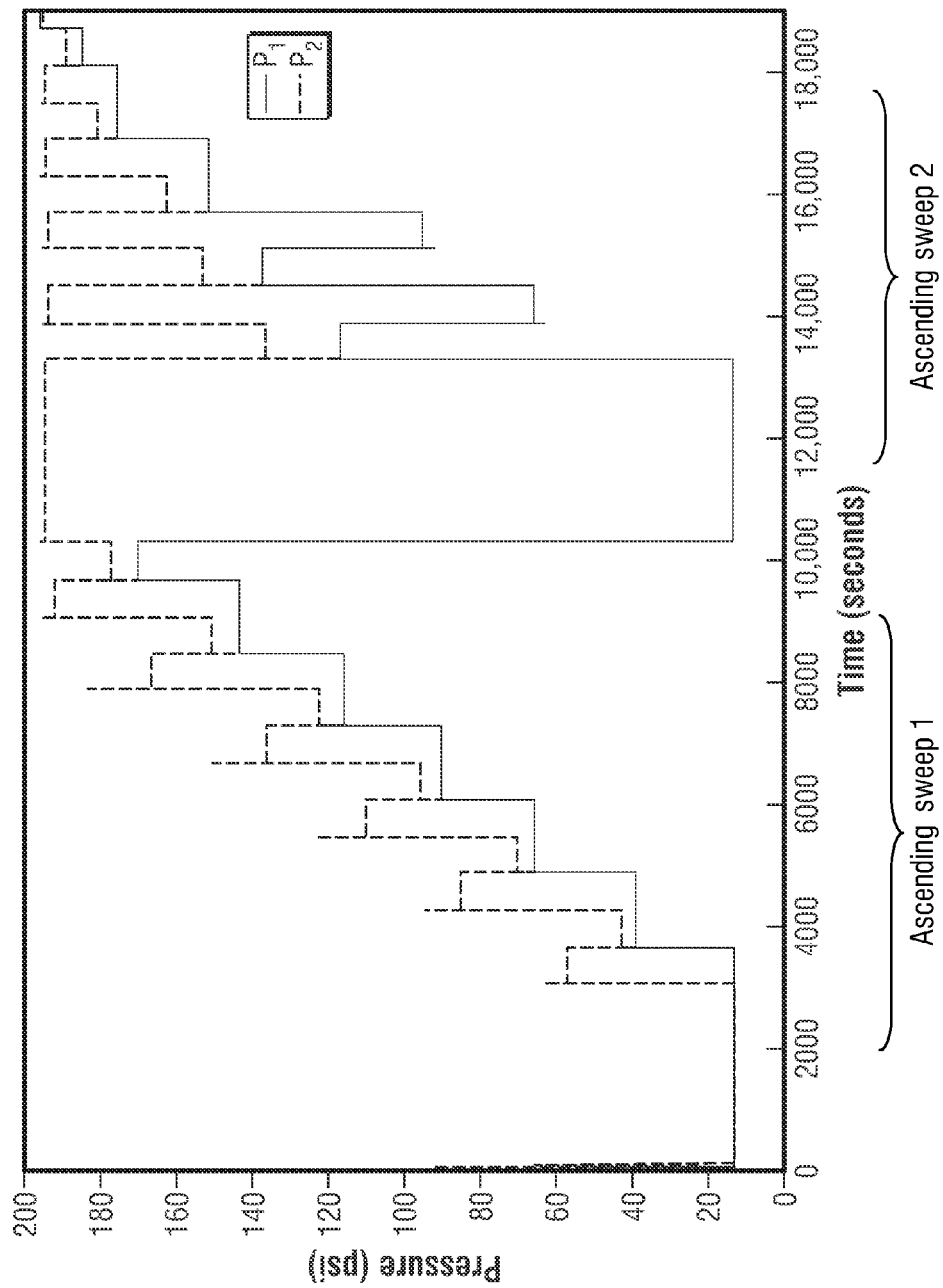

There are several specifically important ways to sweep through various initial pressure combinations, which allow for reduction in the total number of combinations while emphasizing important systematic inconsistencies in volume ratio estimation at different pressures. The first one denoted 'sweep 1', maintains fixed initial pressure differences between $P_{1-time0}$ and $P_{2-time0}$ and cycles through various absolute values of initial pressures (for example, 7 to 11 pressure levels) in the working pressure range of the apparatus. There is a descending 'sweep 1', when both pressures are cycled from high to low values and an ascending 'sweep 1', when both pressures are cycled from low to high values. The second one denoted 'sweep 2', cycles though various initial pressure differences between $P_{1-time0}$ and $P_{2-time0}$ (for example $\delta_i$ to 7 various pressure differences) in the working pressure range of the apparatus. There is a descending 'sweep 2', when initial pressure in the sample cell 103 is low (close to atmospheric pressure, $P_{atm}$) and the initial pressure in the reference cell 101 is changed from high to low values. There is an ascending 'sweep 2', when the initial pressure in the reference cell 101 is high (close to source pressure, $P_s$) and initial pressure in the sample cell is changed from low to high values. In both descending and ascending 'sweep 2' the difference between initial pressures is cycled from high to low values. Examples of the descending and ascending sweeps are shown in FIGS. 12A and 12B. These different sweeps are indicative of pressure sensor non-linearity and possibly other reasons that could make estimation of volume ratio and therefore grain density in the sample cell not perfectly consistent at different initial pressure levels and pressure combinations during testing.

Specifically, the calibration operations can be logically partitioned into two main steps. The first step involves the execution of a testing script that measures and records various initial and final pressure combinations within the working pressure range of the apparatus (obtained with 'sweep 1' cycles and 'sweep 2' cycles) for various sets of billets 127 in the sample cell 103. In one embodiment, the sets of billets 127 vary from empty (where there are no billets 127 in the sample cell 103) to a large number of billets 127 that completely fill the sample cell 103. The second step involves the calculation of the volume ratios between the reference cell 101 and the sample cell 103 and billets 127 and the compensation constants defining corrections for systematic inconsistencies (e.g. non-linearity), that would produce minimum deviation between experimental $k_V$ computed from all recorded pressure combinations and theoretical $k_V$ calculated from volume ratios, billet volumes and compensation constants Minimization of the deviation is done by adjusting trial values of calibration constants via Monte-Carlo, gradient search procedure or the like, until the global minimum is found.

In one embodiment, the minimization procedure employs two calibration constants including: i) the volume ratio ($k_{V12}=V_2/V_1$) between the sample cell and the reference cell, and ii) the volume ratio ($k_{Vb}=V_b/V_1$) between the total volume of the full billet set ($V_b$) and the volume of the reference cell. The initial estimate for the ratio $k_{V12}$ can be obtained as an average of the experimental $k_V$ recorded in the calibration test with an empty cell. The initial estimate of the $k_{Vb}$ can be obtained by subtracting an average of the experimental $k_V$ recorded in the calibration test with a full set of billets (labeled "$k_V(V_b)$") from the initial estimate for the ratio $k_{V12}$ as follows:

$$k_{Vb} = k_{V12} - k_V(V_b). \quad (14)$$

Alternatively, this estimate can also be done with a different set of billets 127 of known volume that, preferably, makes up nearly a full sample cell, because the estimate of $k_{Vb}$ with a nearly empty cell is less robust.

After the volume ratios are known, the absolute volumes of the two cells can be recalculated by:

$$V_1 = V_b/k_{Vb}, V_2 = V_b/k_{Vb} * k_{V12}. \quad (15)$$

Note that in an ideal scenario, when there is no significant pressure non-linearity and other systematic inconsistencies in the measured $k_V$ at different pressures, when the deviation between measured and theoretical $k_V$ is within acceptable tolerance for all tests recorded under different conditions, the initial estimate of volume ratios may be sufficient and no further adjustment of calibration constants may be required.

In the situation when after the initial volume ratio estimation there is still a systematic trend in the $k_V$ error as function of pressure and type of pressure cycling sequence ('sweep 1' versus 'sweep 2'), the biggest source of the error is typically pressure sensor non-linearity. Non-linearity corrected pressure can be defined as follows:

$$P^* = Pf(P), \quad (16)$$

where $f$ is an explicit function of pressure.

In one embodiment, the function $f(P)$ is a first order polynomial such that Eq. (16) can take the form:

$$P^* = P(1 - aP), \quad (17)$$

where a is a non-linearity coefficient.

The volume ratio $k_V$ can be calculated by:

$$k_V = \frac{(P^*_{1-time0} - P^*_{1-time-end})}{(P^*_{2-time-end} - P^*_{2-time0})}. \quad (18)$$

In the event that Eq. (17) is used, the non-linearity coefficient α can be adjusted together with volume ratios until the $k_V$ error reaches minimum for all recorded volume ratio tests.

Compensation for Compressibility of Cell Volume.

The calibration operations can also compensate for compressibility of cell volumes. For example, the volumes can be considered changing with pressure as follows:

$$V_1 = V_1(1 + \beta_1 P_1^*), \text{ and} \quad (19A)$$

$$V_2 = V_2(1 + \beta_2 P_2^*), \quad (19B)$$

where $\beta_1$ and $\beta_2$ are compressibility coefficients.

The volume ratio $k_V$ can be calculated as:

$$k_V = \frac{(P^*_{1-time0} - P^*_{1-time-end})}{(P^*_{2-time-end} - P^*_{2-time0})} + \beta_1 \frac{(P^*_{1-time0})^2 - (P^*_{1-time-end})^2}{(P^*_{2-time-end} - P^*_{2-time0})} - \beta_2(P^*_{2-time-end} + P^*_{2-time0}). \quad (20)$$

After compressibility correction is introduced, all of the calibration constants including volume ratios and non-linearity have to be re-adjusted simultaneously to find the new best minimum of $k_V$ error.

The output of the calibration steps for precise estimation of system volumes, compensation of non-linearity of pressure sensors and compensation of volume compressibility can be described, as a minimum, by 5 parameters: $V_1$ and $V_2$ are precise reference and sample cell volumes, a is pressure non-linearity constant, and $\beta_1$ and $\beta_2$ are compressibility coefficients. Having an estimation of the two volumes is mandatory. Non-linearity constant and compressibility coefficients may be set zero, if corresponding corrections are negligibly small and not required based on the analysis of all $k_V$ measurements at different conditions. Instead of the simple non-linearity correction of Eq. (17) which is defined by a single non-linearity coefficient, the more complicated correction of Eq. (16) may need to be implemented if required by calibration data. Correction for pressure transducer non-linearity of Eqs. (16) or (17) and correction for pressure transducer difference as defined by Eqs. (10) or (11) can be applied to the pressure-time data at the stage when the recorded pressure-time data is uploaded into the data analysis module 137. Analysis and interpretation of data, pressure decay curve fitting, is performed using the corrected pressure values. Precise volumes of reference and sample cell and volume compressibility coefficients are used at the stage of grain volume, porosity, and permeability estimation after finding the model pressure diffusion curves with best match to the experimental data. These operations are discussed in detail in further sections.

Note that the minimum and maximum deviation of the measured $k_V$ after all corrections have been applied and the theoretical $k_V$ calculated from the billets volumes loaded in the sample cell 103 represents the residual precision of grain volume measurements provided by the calibrated pressure decay machine. Typical precision values that can be achieved with 0.1% full scale accuracy pressure sensors are on the order of +/−0.05% of $V_1$. Since the estimation of the absolute value of reference cell volume $V_1$, is done from the known total billet volume, $V_b$, the accuracy of the grain volume measurement is determined by the error in the input billet volume.

Compensation for Thermal Fluctuations in the Testing Gas.

The calibration operations can also include operations that compensate for thermal fluctuations in the testing gas as well as for external thermal fluctuations. Transient pressure techniques with gases are known to be sensitive to thermal fluctuations of the gas. If a certain amount of gas is enclosed in a constant volume, then any temperature changes would result in a pressure change (ΔP) that is proportional to changes in the compressibility factor (ΔZ) and temperature (ΔT). Thus, ΔP~(ΔT+TΔZ). The different sources of thermal fluctuation in a gas in the testing setup can be divided into internal and external thermal fluctuations. Internal temperature fluctuations can be due to adiabatic effects during compression/expansion of gas, friction, the Joule-Thompson effect during gas flow, and chemical reactions with the gas. External temperature fluctuations of the testing gas are due to any temperature changes outside of the test apparatus, and the following equilibration of temperature between the testing gas and the environment. There are several known techniques that can reduce thermal fluctuations during transient gas pressure measurements. These include using a thermally conductive gas, and using helium as a testing gas, which has high thermal diffusivity and low inversion temperature. At the same time, for data interpretation, the testing can be done under isothermal conditions, which is an approximation that often is not met.

In one embodiment, the effects of external temperature fluctuations (due to any sources of heat outside of the reference and sample cells, excluding temperature fluctuations due to adiabatic expansion and compression of the testing gas) on the pressure measurements in the testing gas are compensated for by the introduction of a thermally corrected pressure $P_T$ in place of a direct pressure measurement P over time where $P_T$ is given as:

$$P_T(t) = P(t) \frac{T(t)}{T(t_{end})}, \qquad (21)$$

where P(t) and T(t) are the pressure and the temperature measured and recorded for the sample cell 103 (or the reference cell 101), and $T(t_{end})$ is the temperature measured and recorded for the sample cell 103 (or the reference cell 101) at the end of the pressure decay or pressure degas stage.

This correction compensates for the effects of external temperature fluctuations on the pressure measurements in the testing gas where the characteristic times of the external temperature fluctuations are above the response time of the temperature measurements. Note that the characteristic times of external temperature fluctuations affecting testing gas pressure are much longer than the response time of temperature sensors 119 and 123, as a result of thermal insulation of the testing gas by the walls of the cells 101 and 103 and as additional thermal insulation afforded by the system housing 151. These types of fluctuations can be completely compensated by using thermal measurements.

The time scale of temperature fluctuations from internal sources can vary significantly depending on the testing conditions and properties of the tested material, but this timescale is comparable to or faster than the measurement response time. Therefore, this type of fluctuation is partially compensated by introduction of the thermally compensated pressure. There are two main approaches to mitigate the influence of thermal fluctuations from internal sources on permeability measurements. The first approach is related to characterization of thermal effects and cancellation of their contribution in the recorded transient pressure data at the stage of data processing. The second approach is related to optimization of the hardware design and testing procedures to both accelerate the dissipation and reduce the amplitude of thermal fluctuations.

For the first approach, a series of tests can be run at variable pressures with an empty sample cell and with various combinations of billets in the sample cell, but without any porous samples. Internal thermal fluctuations have a time scale comparable or less than the response time of thermal measurements. At the same time, the response of transient pressure measurements is much faster and allows the system to record the effect of temperature on pressure with good temporal resolution. During the rapid gas flow from the reference cell 101 to the sample cell 103 at the beginning of the test, the gas in the sample cell 103 is adiabatically compressed and heated and then dissipates the heat in the walls of the sample cell 103 and the billets 127. This cooling of the testing gas is reflected as a decreasing transient pressure in the sample cell 103, which is similar in appearance to pressure decay due to gas diffusion into the porous material, but has much shorter relaxation time. The recorded thermal pressure decay for each test in the series of tests (i.e. at variable pressures and combinations of billets) can be processed with curve fitting using an appropriate computation (such as the single exponent model as described herein) to describe the pressure decay due to cooling for the specific testing apparatus. The output of the curve fitting will be the relaxation time $\tau_T(P_0, V_{billets})$ and the amplitude $P_T(P_0, V_{billets})$ of the thermal pressure decay as a function of testing pressure and volume of billets in the sample cell. The relaxation times and amplitudes of the thermal pressure decays due to internal thermal fluctuations on the specific testing apparatus are stored to be used later for compensation of the fast thermal effect during permeability measurements. Specifically, the data analysis module can be configured to ignore the pressure measurements in the sample cell during the relaxation time $\tau_T$ and thus use only pressure signal recorded after the relaxation time $\tau_T$, which is considered clean from thermal effects.

Note that a test that combines both rock sample 129 and billets 127 in the sample cell 103, the actual set of billets (or empty cell) will provide the high-bound estimate of relaxation time, because the additional grain volume of the rock further reduces the dead volume in the cell and therefore the thermal effect, and because total heat capacity of the rock is typically much lower than heat capacity of the cell. In case of testing of the non-rock material with potentially high heat capacity, additional precautions and quality checks must be performed, such as verifying the actual heat capacity of the material, testing permeability on the reduced amount of material obtained by splitting, and testing permeability and porosity at different pressures.

Another way to characterize and compensate for the effect of temperature fluctuations from internal sources on permeability measurements is to introduce a quality index, which is based on the ratio of the surface under the pressure decay curve recorded for the combination of porous sample and billets ($S_P$) and the surface under the thermal pressure decay recorded for the corresponding set of billets ($S_{P_T}$). Pressure decay curves in this case are used for interpretation without removing of the early part contaminated with temperature effects. The ratio above a certain threshold, e.g. $S_{P_T}/S_P > 0.2$, would indicate a pressure decay permeability measurement, which includes too much thermal response in the pressure signal. With proper calibration of the introduced indicator it flags both the permeability pressure decay curves which are too fast and have very short relaxation time and which are too slow and have too small pressure amplitude. Both of these situations indicate that the recorded pressure decay curves are very close or beyond the measurement capabilities of the specific equipment and therefore have reduced measurement quality.

The most accurate way to compensate for early time internal thermal effect is to predict dynamics of gas heating and cooling in the sample cell and subtract the transient pressure changes due to adiabatic effects from the full pressure signal to produce a clean pressure curve caused by gas diffusion alone. However, this method requires a-priori information about the thermal properties of rock, which is often unavailable, and accurate modeling of the cooling taking account of the geometry of the porous sample, which can be computationally expensive.

For the second approach that mitigates the influence of thermal fluctuations from internal sources on permeability measurements, the hardware design of the testing apparatus and testing process can be optimized for this purpose as follows:

use of testing gas with low heat capacity and high thermal conductivity, such as helium;

manufacturing of the cells and piping from materials with high thermal conductivity and high thermal capacity;

minimizing dead volume in the sample cell as much as possible by using a billet set tightly filling the cell; by accurately packing tested porous material in the cell; by using the isolated cell testing;

introducing additional elements of known volume in the sample cell together with the tested porous material and billets, which would have low heat capacity, high thermal conductivity and would accelerate the heat sink from the bulk of the sample cell volume to the cell walls. These additional elements can be implemented in the form of thin elongated fibers or pieces of metal wire uniformly distributed in the cell with sufficient amount of contacts between them. Such elongated elements provide fast heat transfer along their main direction and do not introduce much additional heat capacity because of their small volume. The fibers have to be conveniently removable from the pack of the tested material and billets and reusable; and monitoring of temperature simultaneously with pressure on every measurement is essential to ensure complete dissipation of fast temperature fluctuations from internal sources and validate the quality of isothermal assumptions.

Quality control of permeability measurements using standard permeability Samples.

The calibration operations can also include operations that confirm that permeability measurements made on the same samples produce consistent results on the testing apparatus along with different permeability machines. The most convenient way to do it is to run measurements on manufactured standard permeability samples, which have highly uniform spatial microstructure and therefore single permeability (or very narrow permeability distribution). An important example of geometrical implementation of such samples is cylinders with low stress sensitivity and sealed lateral surfaces, which can be used to compare measurement both on different pressure decay machines and between pressure decay and pulse decay machines. It is critical that prior to testing on different machines the condition of the sample is identical, e.g. saturations in the sample are the same, there are no changes in the sample properties due to mechanical loading during confined pulse decay testing, there is no contamination of the sample's surface. It is highly recommended to minimize the time delay between testing of the same sample on different machines to ensure they are in identical state. Precautions have to be implemented to ensure clean handling and storage of the sample to minimize contamination. It is more preferable to use manufactured samples than samples of natural material, because the latter have more chances to be stress sensitive, especially due to coring induced microcracks, and are more non-uniform and therefore have wide distribution of permeabilities, which makes comparison of pressure decay and pulse decay permeability impossible. Natural samples can only be used if low stress sensitivity and uniformity is assured with high confidence. Comparison between pressure decay machines alone can be done using fragmented material or arbitrary shaped material. Natural rock material is possible, but manufactured material is preferred because nearly all of the porous rocks tend to continue fragmenting by a tiny bit into smaller pieces during normal handling required for permeability testing, e.g. loading and unloading in the cell. Again the critical condition is that sample condition is identical prior to testing on each of the machines.

The difference in grain volume measurement made on different pressure decay machines has to be within the tolerance on these machines that was identified during calibration of their $k_V$ measurements. The normal difference in gas-probed porosity and gas-probed permeability estimated on the same material on different pressure decay machines is within 5-10%. The normal difference in pulse decay and pressure decay permeability of the same single permeability sample estimated at same pore pressure is within 15-20%.

The operations of the valve control and interface module 133 and the data acquisition module 135 in carrying out the testing methodology (e.g., test script) as described herein results in data stored by the data processing system 131. In one embodiment, such data includes a set of five numerical arrays ti, P1$i$, P2$i$, T1$i$, T2$i$, T0$i$ where the data values of the five numerical arrays are linked by the corresponding index i. Specifically, the data values of the array ti represent a set of timestamps over the time period encompassing a given experiment. The data values of the array P1$i$ represent a set of pressures measured by the pressure sensor 117 of the reference cell 101 at the times corresponding to the associated timestamps of the array ti. The data values of the array T1$i$ represent a set of temperatures measured by the temperature sensor 119 of the reference cell 101 at the times corresponding to the associated timestamps of the array ti. The data values of the array P2$i$ represent a set of pressures measured by the pressure sensor 121 of the sample cell 103 at the times corresponding to the associated timestamps of the array ti. The data values of the array T2$i$ represent a set of temperatures measured by the temperature sensor 123 of the sample cell 103 at the times corresponding to the associated timestamps of the array ti. The data values of the array T0$i$ represent a set of temperatures measured by the temperature sensor 125 at the times corresponding to the associated timestamps of array ti. These numerical arrays can be stored in an ASCII text file or other suitable format.

Before analyzing pressure decays, the data analysis module 137 extracts the data segments corresponding to a respective pressure decay stage and subsequent degas stage of the experiment from the numerical arrays and shifts the data segments to the same starting time t0. Time t0 is identified by the timestamp value for the time when the pressure of the sample cell 103 as recorded in the numerical array P2$i$ starts rapidly increasing after the intermediate valve 107 has been opened. The data analysis module 137 also provides for entry and recording of additional data associated with the experiment and required for later data processing, such as current volumes of reference cell 101 and the sample cell 103, billets 127 and mass of the tested material loaded in the sample cell 103 and to save the bundled data in binary format for later processing.

Before interpretation, the raw pressure data corresponding to the individual pressure decay stages and degas stages is transformed to correct for the pressure transducer difference using Eq. (11) and to correct for pressure transducer non-linearity using Eq. (16) or (17). All subsequent steps are utilizing corrected pressure values, which are functions of uncorrected pressures and, possibly, temperature, if the pressure difference correction had to incorporate temperature influence.

Next, the data analysis module 137 processes the corrected values of the data segments corresponding to the respective pressure decay stage and subsequent degas stage of the experiment to characterize permeability and porosity of the test sample. Note that the processing of the data segment of the degas stage is analogous to the processing of the data segment of the pressure degas, except that the direction of pressure change is reversed and the pressure level at which these measurements are made is lower than for the pressure decay stage. Such data processing involves matching the corrected values of the data segments corresponding to the respective pressure decay stage and subsequent degas stage of the experiment to pressure curves (i.e., pressure data) generated by a computational model where the pressure curves are related to materials of known porosity and permeability characteristics. The permeability and porosity of the test sample can be derived from the porosity and permeability characteristics of the material related to the best-matching pressure curve, if any. The computation model can be selected by the operator, dictated by the design of the system, or selected by other methods. The matching can employ best-fit curve fitting or other suitable statistical processing that matches the corrected values of the data segments corresponding to the respective pressure decay stage and subsequent degas stage of the experiment to pressure curves (i.e., pressure data) generated by a computational model. Such matching preferably analyzes the data segments corresponding to the entire pressure decay stage and the entire degas stage of the experiment, and thus does not analyze only the early-part or late-part of pressure decay stage or the entire degas stage of the experiment, respectively.

In one embodiment, the computational model of the pressure decay stage can be based on exponential pressure decay and take the form:

$$P_2(t) = b(\alpha \cdot e^{-(t-t_0)/\tau} + 1). \quad (22)$$

In another embodiment, the computational model of the pressure decay stage can be based on a full analytic solution for constant compressibility gas diffusion into spherical particles and take the form:

$$P_2(t) = b\left(6\alpha(\alpha+1)\sum_{m=1}^{\infty} \frac{1}{\theta_m^2 + 9(\alpha^2 + \alpha)} \times e^{-\theta_m^2(t-t_0)/\tau} + 1\right), \quad (23)$$

where $\theta_m$ are the roots of $$\tan\theta_m = \frac{3\theta_m}{3 + \theta_m^2/\alpha}.$$

These two models are very fast to compute and therefore suitable for automatic fitting. Each of these models defines a set of pressure curves that are controlled by three parameters: $\alpha$, b and $\tau$. The parameter $\alpha$ is a storage coefficient that defines the ratio of pore volume to dead volume. The parameter b relates to the final pressure in the sample cell 103 after pressure decay is complete and pressure inside and outside of the pore volume of the sample 129 is completely stabilized. The parameter $\tau$ is a relaxation time. The parameter b by can be replaced by an equivalent dimensionless parameter $\beta$ according to the following:

$$\beta = b\frac{\alpha+1}{P_{20}}, \quad (24)$$

where $P_{20}$ is the initial pressure in the sample cell 103 equal to pressure inside the pore volume of the sample 129, before any gas flow from the reference cell 101 into the sample cell 103 is started.

The parameter $\beta$ is a factor that relates the initial pressure outside the porous sample to initial pressure inside the pore space. The computational model of Eq. (22) is the late time asymptote of the computation model of Eq. (23), and it can be used as a proxy model to calculate the best fit for computation model of Eq. (23), meaning that the best fit of the computational model of Eq. (22) can be used as the initial guess to find the best fit of computational model of Eq. (23). Similar computational models can be used for the degas stage of the experiment.

The computational models of the pressure decay stage and pressure degas stage can be extended to account for a variety of thermodynamic interactions of the testing gas and the test sample and other testing conditions.

For example, the computational models of the pressure decay stage and pressure degas stage can be extended to account for variable gas compressibility and Klinkenberg gas slippage. In this case, the set of pressure curves defined by the computational models can be based on additional parameters corresponding to a gas factor Z and a slip parameter b.

In another example, the computational models of the pressure decay stage and pressure degas stage can be extended to account for diffusion of the testing gas into cylindrical particles. In this case, the set of pressure curves defined by the computational models can be based on an additional parameter corresponding to the length to radius ratio $D/R_s$ of the cylindrical particles.

In yet another example, the computational models of the pressure decay stage and pressure degas stage can be extended to account for diffusion of the testing gas into rectangular particles. In this case, the set of pressure curves defined by the computational models can be based on additional parameters corresponding to the ratio of the first and second largest dimensions of the particles to the smallest dimension of the particles (i.e., $r_1/r_3$, $r_2/r_3$).

In still another example, the computational models of the pressure decay stage and pressure degas stage can be extended to account for diffusion of the testing gas into particles of defined shape with sealed and open surfaces. In this case, the set of pressure curves defined by the computational models can be based on additional parameters corresponding to the geometry of the particles and the sealed versus open surfaces.

In yet another example, the computational models of the pressure decay stage and pressure degas stage can be extended to account for diffusion of the testing gas into particles (which can have spherical, cylindrical, or rectangular geometry) together with variable gas compressibility and pressure dependent permeability. In this case, the set of pressure curves defined by the computational models can be based on additional parameters corresponding to the geometry of the particles along with parameters corresponding to the gas factor z(P) and the user defined permeability law $$\frac{k}{k_0} = f(P).$$

In still another example, the computational models of the pressure decay stage and pressure degas stage can be extended to account for anisotropic permeability parallel and perpendicular to bedding. In this case, the set of pressure curves defined by the computational models can be based on an additional parameter corresponding to the ratio $k_x/k_z$.

In another example, the computational models of the pressure decay stage and pressure degas stage can be extended to account for gas adsorption. In this case, the set of pressure curves defined by the computational models can be based on parts or all of the Langmuir adsorption model or the Brunauer-Emmett-Teller adsorption model or other adsorption model.

In another example, the computational models of the pressure decay stage and pressure degas stage can be extended to account for sequentially connected porosity systems (dual permeability model, n-permeability model). In this case, the set of pressure curves defined by the computational models can be based on parts or all of a multiple-system porosity model with additional parameters corresponding to the breakdown of the total porosity $\phi_i/\phi_{total}$ between porosity systems and relative permeabilities of the systems $k_i/k_1$.

In still another example, the computational models of the pressure decay stage and pressure degas stage can be extended to account for a multimodal distribution of fragment sizes and shapes as part of the test sample. This is useful when the test sample comprises several shapes and sizes of fragments mixed together with a known frequency for each component. In this case, the set of pressure curves defined by the computational models can be based on parameters for the size and frequency of the fragment components. Note that for the particular case of spherical particles, it is practical to estimate a single effective size of the particles ($R_s$)) as:

$$R_s = \frac{1}{N}\sqrt{\sum_{i=1}^{N} n_i R_i^2}, \quad \sum_{i=1}^{N} n_i = 1, \tag{25}$$

where $R_i$ is the radius of each size component, and
$n_i$ is the frequency of each size component.

This approximation works with sufficient accuracy, for example, when the ratio of minimum to maximum size in the distribution is up to four.

In yet another example, the computational models of the pressure decay stage and pressure degas stage can be extended to account for thermal effects of the testing gas, such as the thermal effect due to slow (limited by inertia of thermal measurements) changes of gas temperature. In this case, the set of pressure curves defined by the computation model can be corrected for temperature variations using Eq. (21).

In yet another example, the computational models of the pressure decay stage and pressure degas stage can be extended to account for a slow component of pressure decay due to leaks. In this case, the set of pressure curves defined by the computational models can be based on a parameter corresponding to a leak rate L as follows:

$$P_{model\_LC}(t) = P_{model}(t) - L\int_{t_0}^{t}(P_{model}(t) - P_{atm})dt. \tag{26}$$

where $P_{model\_LC}$ is the pressure corrected for leakage,
$P_{model}(t)$ is the pressure calculated by the computational model without accounting for leakage,
L is the leak rate, and
$P_{atm}$ is the average value of the atmospheric pressure at a location on the test apparatus.

In yet another example, one or more computational models can be combined with one another.

The computational model can be computed, tabulated and then approximated using a proprietary empirical function, which allows fast, fully automatic fitting. Depending on the specific computational model, the model curves may or may not be efficiently approximated and sometimes require computationally expensive modeling.

The data processing that automatically fits the computational model(s) to the experimental data (i.e., the corrected values of the data segments corresponding to the respective pressure decay stage and subsequent degas stage of the experiment) can be based on adjusting one or more parameters of the computational model(s) (such as the parameters ($\alpha$, $\beta$, $\tau$, and the leak rate L) using standard multivariable optimization algorithms (such as the Nelder-Mead simplex algorithm, gradient search, or particle swarm optimization). In one embodiment, the best fit is determined by minimizing the differences between the experimental pressures $P_{exp}(t_i)$ and the model pressure curves $P_{model}(t_i)$ according to the function:

$$\Delta P_{L_2} = \frac{1}{N}\sqrt{\sum_{i=1}^{N}(P_{exp}(t_i) - P_{model}(t_i))^2}. \tag{27}$$

A minimum set of fixed parameters may be required to calculate the best fit. These fixed parameters can include i) the free volumes of the reference cell 101 and the sample cell 103 (i.e., the cell volume subtracting the volume of the billet(s) 127 in the sample cell 103; ii) the initial guess for the bulk sample volume; iii) parameters corresponding to the geometry of the test sample, such as the radius of spherical particles, $R_s$; and iv) other necessary parameters for the computational model as needed.

With all of the volumes (i.e., the volume $V_1$ of the reference cell 101, the volume $V_2$ of the sample cell 103, and the volume $V_b$ of the billet(s) 127) known, the values of curve-related variables (e.g., $\beta$, $\alpha$, $\tau$) for the best-fit pressure curve derived from the computational models can be transformed into an estimation of sample-related properties, including bulk volume $V_{sample}$ of the test sample, porosity $\phi$ of the test sample, and permeability k of the test sample.

For example, the bulk volume $V_{sample}$ of the test sample, in the case of no compressibility of cell volumes, can be derived as:

$$V_{sample} = V_2 - V_b + V_1\frac{P_1(t_{end}) - P_1(t_0)}{(\beta - 1)\cdot P_2(t_0)}, \tag{28}$$

where $P_1(t_{end})$ is the pressure of reference cell 101 at time $t_{end}$, which occurs at the expiration of the pressure decay stage or the degas stage;
$P_1(t_0)$ is the pressure of the reference cell 101 at time $t_0$, which occurs at the beginning of the pressure decay stage or the degas stage, just before any flow between the cells is started;
$P_2(t_0)$ is the pressure of the sample cell 103 at time $t_0$, which occurs at the beginning of the pressure decay stage or the degas stage, just before any flow between the cells is started; and
$\beta$ is the value of $\beta$ for the best-fit pressure curve derived from the computation models.

In the case of the non-zero volume compressibilities $\beta_1$ and $\beta_2$ estimated during the calibration stage, the bulk volume of the sample is given by $$V_{sample} = V_2 - V_b - \qquad (29)$$
$$V_1\left[\frac{P_1(t_0) - P_1(t_{end})}{(\beta - 1) \cdot P_2(t_0)} + \beta_1 \frac{P_1(t_0)^2 - P_1(t_{end})^2}{(\beta - 1) \cdot P_2(t_0)} - \beta_2(\beta + 1) \cdot P_2(t_0)\right].$$

The porosity φ of the test sample, in the case of no compressibility of cell volumes, can be derived as:

$$\phi = \alpha \cdot (V_2 - V_{billets} - V_{sample})/V_{sample}, \qquad (30)$$

where α is the value of a for the best-fit pressure curve derived from the computation models.

In the case of the non-zero volume compressibility $\beta_2$ estimated during the calibration stage, the porosity of the sample is given by:

$$\phi = \alpha_{corr} \cdot (V_2 - V_{billets} - V_{sample})/V_{sample}, \qquad (31A)$$

$$\alpha_{corr} = \alpha\left[1 + \beta_2 \frac{(V_2)}{(V_2 - V_{billets} - V_{sample})} \cdot \frac{\beta(\alpha + 2) + \alpha}{\alpha + 1} \cdot P_2(t_0)\right], \qquad (31B)$$

where α and β are the values of α and β for the best-fit pressure curve derived from the computation models.

The permeability k of test sample can be derived as:

$$k = \mu_{gas} C_{gas} R_s^2 \frac{\varphi}{\tau}, \qquad (32)$$

where $\mu_{gas}$ is viscosity of the testing gas,
$C_{gas}$ is compressibility of the testing gas, and
where τ is the value of τ for the best-fit pressure curve derived from the computation models.

Note that grain volume $V_{grain}$ of the test sample can be calculated from the bulk volume and the porosity as follows:

$$V_{grain} = V_{sample}(1 - \phi). \qquad (33)$$

Figure 4:
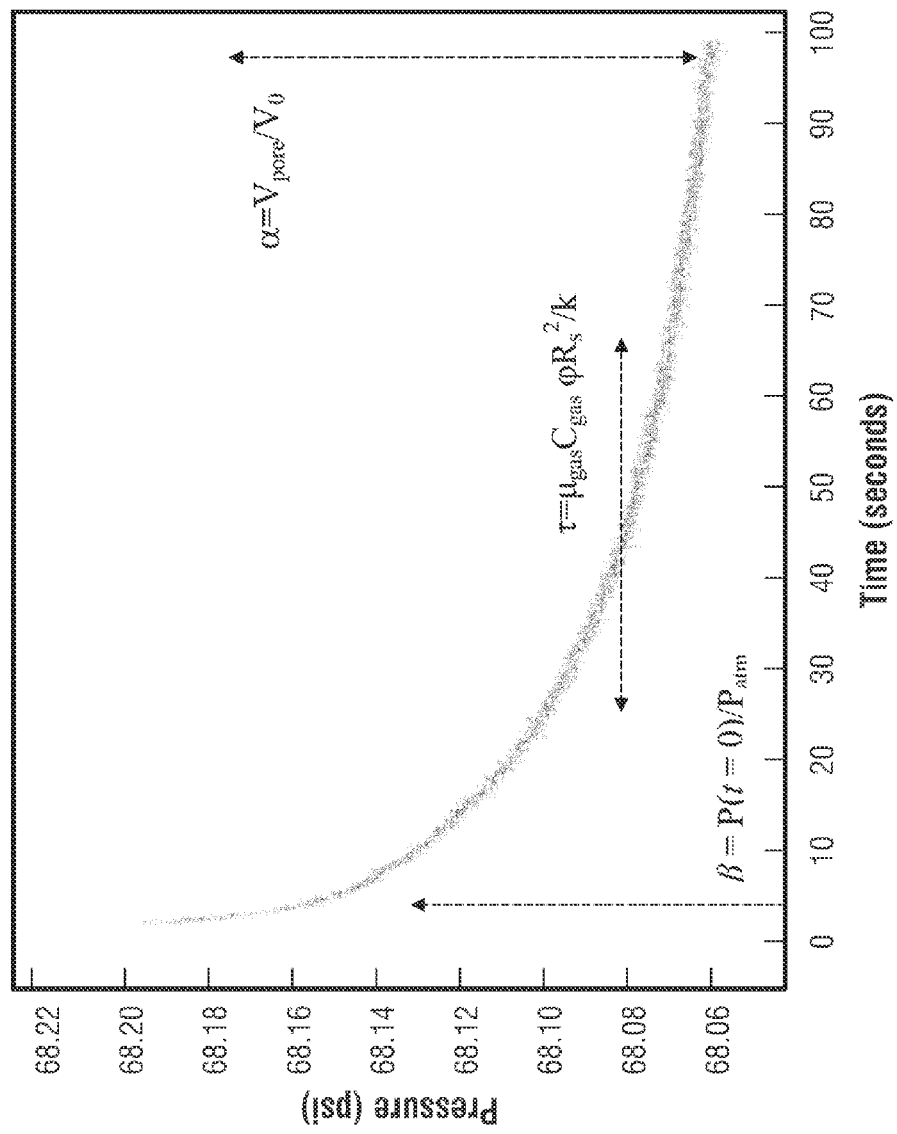
FIG. 4 is an exemplary pressure curve recorded by the apparatus of FIG. 2 with notations that depict how three variables ($\beta$, $\alpha$, $\tau$) are related with the observed pressure curve.

FIG. 4 illustrates how three variables (β, α, τ) are related with the observed pressure curve. The early-time pressure (related to the sample's bulk volume) and β determine the peak pressure before gas diffusion into the porous material of the sample occurs. The storage parameter α related to porosity determines the difference between the initial and final pressure. The relaxation time τ is linked with permeability. Parameters (β, α, τ) are the main controls of the pressure curve shape: β controls position of the top-left corner, α—height of the curve, τ—duration and slope of the curve.

Figure 5A:
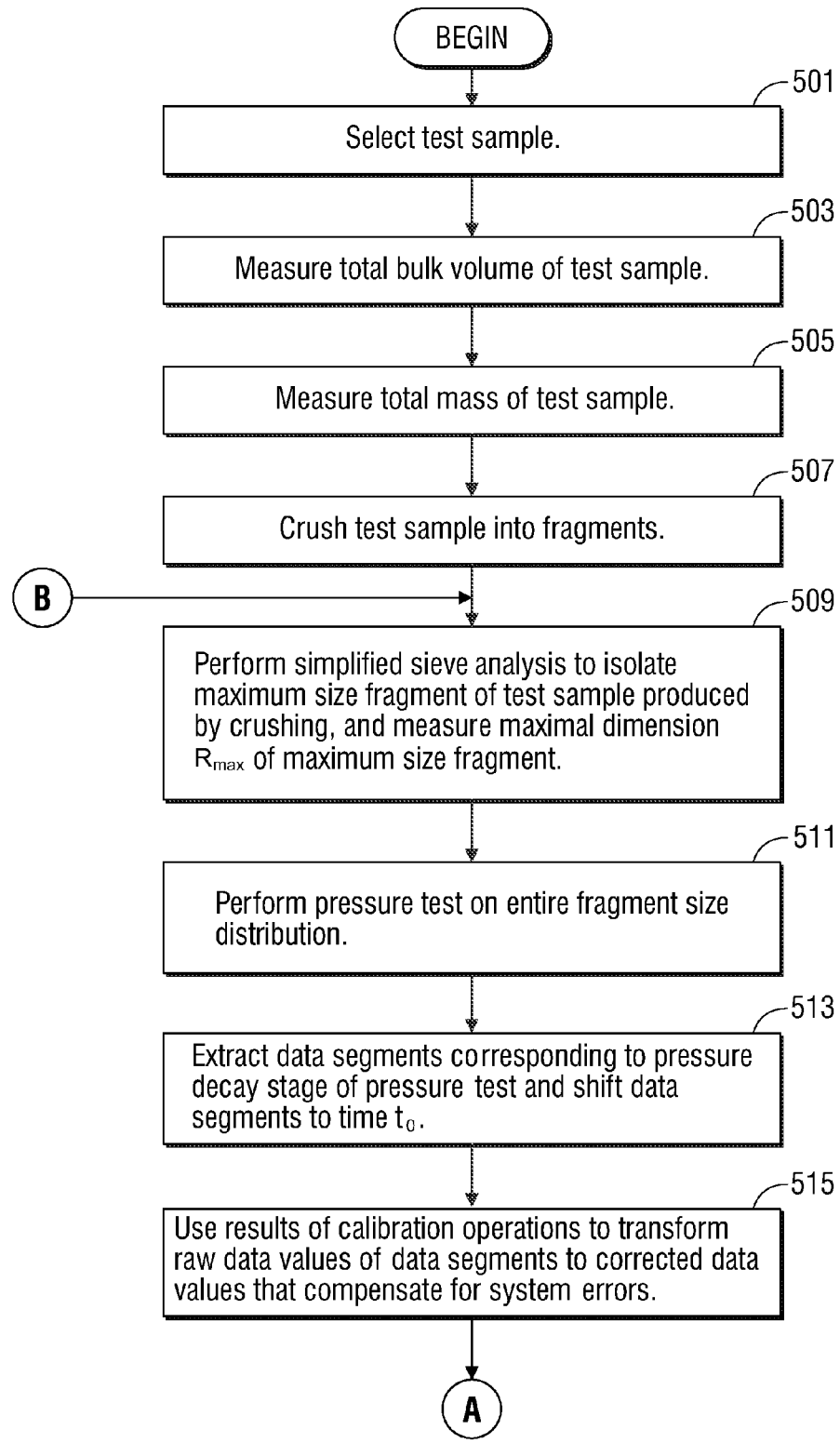
FIGS. 5A-5C, collectively, are a flow chart of operations carried out by the apparatus of FIG. 2 that measures bulk properties (e.g., permeability) of a heterogeneous microporous material.
Figure 5B:
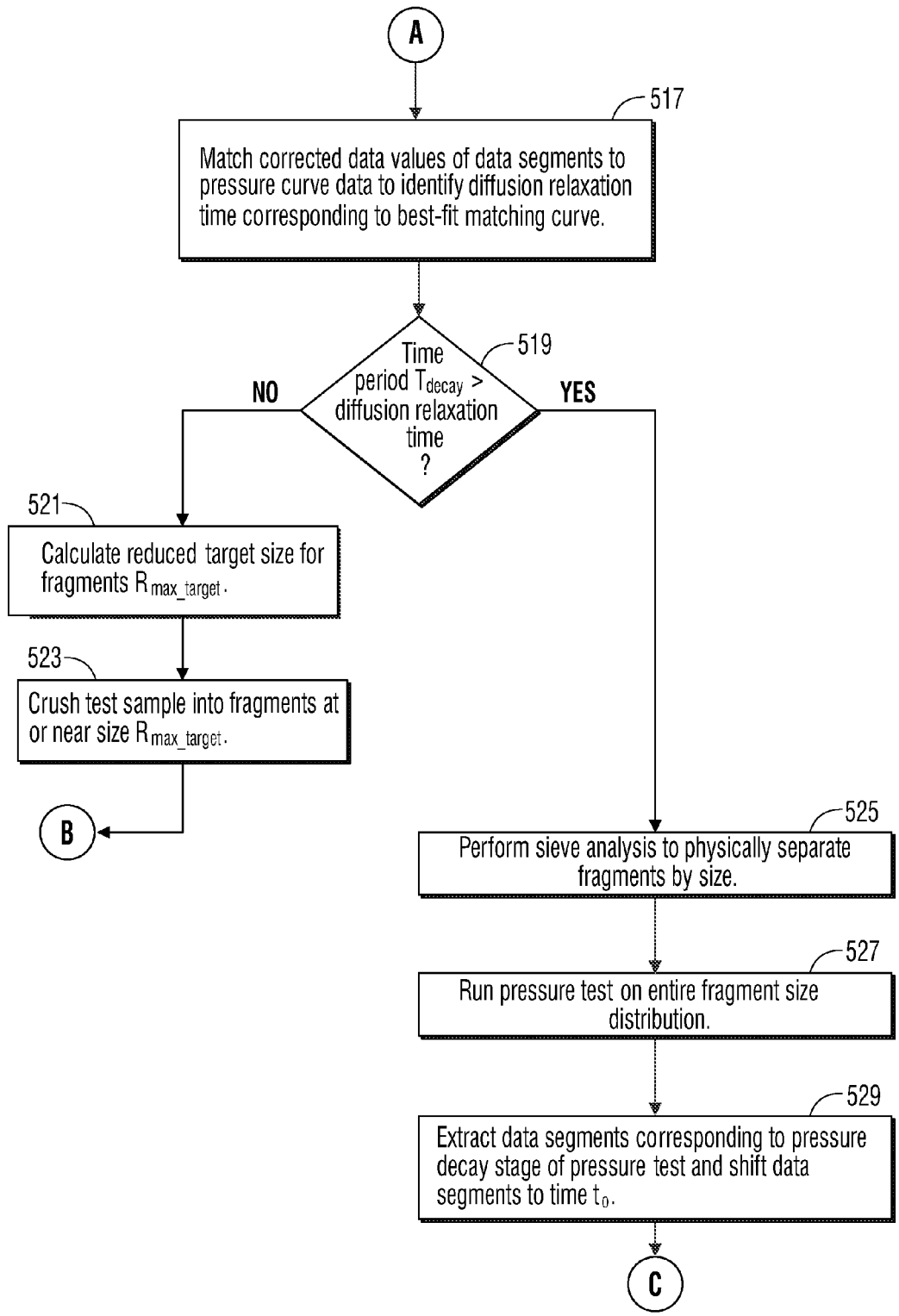
Figure 5C:
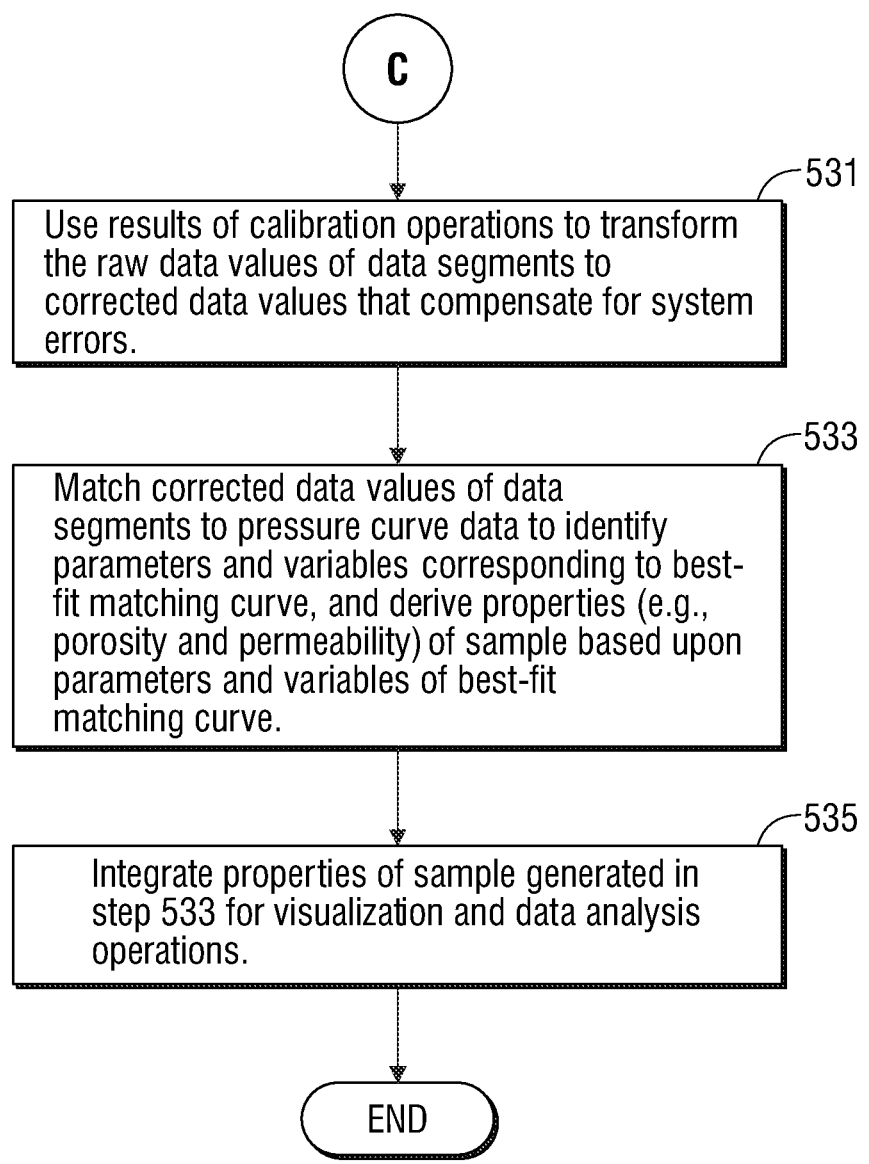

The testing apparatus and method as described above can be adapted to perform one single experiment that measures the bulk properties (e.g., permeability, porosity, and others) of heterogeneous microporous material as shown in the flow chart of FIGS. 5A to 5C. The bulk properties result from a distribution of the respective properties that are inherently present in the heterogeneous microporous material.

In step 501, the sample of heterogeneous microporous material to be tested (i.e., "test sample") is selected.

In step 503, the total bulk volume ($V_{total}$) of test sample is measured using a standard water immersion or mercury immersion method. If the test sample has a well-defined shape (e.g., such as a cylindrical plug), direct measurements of dimensions of the test sample can be performed using a vernier caliper, micrometer, or equivalent and the geometric volume of the test sample can be calculated from the measured dimensions. The geometric volume can be used for quality control of the immersion measurement for measuring the total bulk volume of the test sample.

In step 505, the total mass of the test sample before crushing ($M_{total}$) is measured.

In step 507, the test sample is crushed by crushing equipment that breaks the test sample, which can initially consist of one or more fragments of arbitrary shape, into smaller fragments. The crushing equipment is configured such that the size of the fragments of the test sample produced by the crushing equipment is i) as large as possible and ii) smaller than the largest fragment before crushing so that at least some crushing occurs and sufficiently large fresh surface area is created by crushing. Crushing equipment is typically controlled by some kind of aperture parameter, measured in units of length, which is related to the maximum size of produced fragments. This aperture parameter must be set below the minimum of the three dimensions of the largest of the initial fragments. The largest fragment and its dimension can be roughly estimated from a visual inspection of the fragments, using rough measurements with a ruler or vernier caliper.

In step 509, the dimension of the maximum size fragment of the test sample produced by the crushing of step 507, $R_{max}$, is measured. This can be done by a simplified sieve analysis which isolates the maximum size fragments and relates them to a sieve. Note that the simplified sieve analysis does not measure the masses of the fractions of the fragments that are isolated by the sieve analysis. The $R_{max}$ measurement can also be made using digital image analysis of the fragment set or any other suitable method.

In step 511, a pressure test is run on the entire fragment size distribution resulting from the crushing of step 507. This pressure test can be executed without flushing. Initially, the valve control and interface module 133 controls the intermediate valve 107 to assume a closed position in order to isolate the reference cell 101 from the sample cell 103, and the sample cell 103 is loaded with the entire fragment size distribution resulting from the crushing of step 507 and closed at atmospheric pressure. Zero or more billets 127 can also be loaded into the sample cell 103. The set of billets 127 loaded into the cell is selected in such a way that maximizes the total volume of billets in the cell. The intake valve 111 is controlled to assume an open position to fluidly couple the source of testing gas 109 (preferably helium) to the reference cell 101 in order to fill the reference cell 101 with testing gas at the predetermined elevated pressure of the test. The initial test gas pressure (source pressure $P_s$) is usually set at the highest possible pressure within the working range of the equipment because this setting provides the maximum amplitude of the pressure signal attributed to pressure diffusion. However, the initial pressure can be set at any pressure within the working pressure range (above 2 atmospheres absolute pressure is recommended), if testing at different gas pressure is required. After filling the reference cell 101 with the testing gas, the valve control and interface module 133 controls the intake valve 111 to assume a closed position to isolate the reference cell 101. Next, the valve control and interface module 133 controls the intermediate valve 107 to assume an open position for a very short period of time (typically on the order of tens or hundreds of milliseconds), which is sufficient to flow substantial amounts of the testing gas from the reference cell 101 into the sample cell 103. During this flow period, the pressure in the reference cell 101 falls rapidly, due to gas expansion from the reference cell 101 into the free volume of the sample cell 103. Then, the valve control and interface module 133 controls the intermediate valve 107 to assume a closed position that isolates both the reference cell 101 and the sample cell 103. After the intermediate valve 107 is closed, the gas pressure in the sample cell 103 begins to decrease at a slower rate due to diffusion of gas into the porous sample 129. These operations are referred to as the pressure decay stage and continue for a time period $T_{decay}$. The time period $T_{decay}$ is fixed (e.g., $T_{decay}$=10 minutes). It is understood that in some cases this will not be sufficient to reach full pressure equilibrium. During the test process of step 511 (particularly during the time period $T_{decay}$ of the pressure decay stage), the data acquisition module 135 is configured to cooperate with the pressure sensor 117 and the temperature sensor 119 to measure and record the temperature and pressure of the reference cell 101 over time. The data acquisition module 135 is also configured to cooperate with the pressure sensor 121 and the temperature sensor 123 to measure and record the temperature and pressure of the sample cell 103 over time. Furthermore, the data acquisition module 135 is configured to cooperate with the temperature sensor 125 to measure and record the average temperature of the system over time.

In step 513, the data analysis module 137 is configured to extract the data segments corresponding to the pressure decay stage of the test of step 511 and shift the data segments to the same starting time $t_0$. Time $t_0$ is dictated by the timestamp value for the time when the pressure of the sample cell 101 starts increasing after the intermediate valve 107 has been opened.

In step 515, the data analysis module 137 is configured to utilize the results of one or more calibration operations to transform the raw pressure and temperature values of the data segments of the pressure decay stage as generated in step 513 to corrected values that compensate for systematic errors of the apparatus as described herein.

In step 517, the data analysis module 137 matches the corrected values of the data segments of the pressure decay stage as generated in step 515 to pressure curves (i.e., pressure data) generated by a computational model of the pressure decay stage with curve-related parameters $\alpha$, $\beta$ and $\tau$. The computational model of step 517 assumes that all particles have equal size $R_{max}$ as measured in step 509 and that there is a single permeability for all particles. The matching identifies the pressure curve that is best-fit to the corrected values of the data segments of the pressure decay stage as generated in step 515. The curve-related parameter $\tau$ (diffusion relaxation time) for the best-fit pressure curve is then identified for subsequent processing.

In step 519, the data analysis module 137 compares the curve-related parameter $\tau$ (diffusion relaxation time) identified in step 517 to the time period time period $T_{decay}$ of the pressure decay stage of the test of step 511 in order to determine whether the maximum particle size is appropriate for the pressure testing of step 527 and subsequent data analysis. For the case where the time period $T_{decay}$ is greater than the curve-related parameter $\tau$ (diffusion relaxation time) the operations continue to step 525. For the case where the time period $T_{decay}$ is less than or equal to the curve-related parameter $\tau$ (diffusion relaxation time), the operations continue to step 521.

In step 521, the data analysis module calculates a target maximum particle size $R_{max\_target}$ which is less than the particle size $R_{max}$ measured in step 509. In one embodiment, the target maximum particle size $R_{max\_target}$ is based on the particle size $R_{max}$ measured in step 509, the curve-related parameter $\tau$ (diffusion relaxation time) identified in step 517, and the time period time period $T_{decay}$ of the pressure decay stage of the test of step 511. For example, $R_{max\_target}$ can be calculated as:

$$R_{max\_target} = R_{max} * (T_{test}/\tau)^{1/2} \qquad (34)$$

In step 523, the crushing equipment is configured such that the size of the fragments produced by the crushing equipment is at or near the target maximum particle size $R_{max\_target}$ calculated in step 521, and the fragments of the test sample are crushed further by crushing equipment into smaller fragments at or near the target maximum particle size $R_{max\_target}$. After completing step 523, the operations return to repeat steps 509 to 519 to compare the curve-related parameter $\tau$ to the time period time period $T_{decay}$ in order to determine whether the maximum particle size is appropriate for the pressure testing of step 527 and subsequent data analysis. Multiple iterations of the crushing and testing and analysis of steps 511 to 519 can be performed if necessary.

In step 525, sieve analysis is performed to physically separate the fragments of different sizes from one another and to measure the frequency of each respective fragment size within the particle size distribution of the fragments of the test sample produced by the crushing of step 507 and possibly step 523 as needed.

In step 527, a pressure test is run on the entire fragment size distribution resulting from the crushing of step 507 and possibly step 523 as needed. Before loading the crushed sample into the sample cell 103 the total mass of the loaded fragments ($M_{sample}$) is measured. Initially, the valve control and interface module 133 controls the intermediate valve 107 to assume a closed position in order to isolate the reference cell 101 from the sample cell 103, and the sample cell 103 is loaded with the fragment size distribution at atmospheric pressure. Zero or more billets 127 can also be located within the sample cell 103. The set of billets 127 loaded into the sample cell 103 is selected in such a way that the total volume of billets 127 in the sample cell 103 is maximized. Next, the valve control and interface module 133 controls the intake valve 111 to assume an open position to fluidly couple the source of testing gas 109 (preferably helium) to the reference cell 101 in order to fill the reference cell 101 with testing gas at an initial elevated (for example, at approximately 1 atmosphere above atmospheric or higher). Next, there are a number (for example, three to four) quick flushing cycles to replace air in the dead volume by the testing gas. Each flushing cycle consists of flowing the testing gas from the reference cell 101 to the sample cell 103, closing the intermediate valve 107, and releasing the gas mixture through the exhaust port 113 to atmosphere by opening and then closing the exhaust valve 115. After several flushing cycles, the relative concentration of air and the testing gas in the dead volume becomes negligible (apart from the gas in the pore space with limited permeability), and the pressure in the isolated sample cell 103 is near atmospheric. Next, the valve control and interface module 133 controls the intermediate valve 107 to assume a closed position in order to isolate the reference cell 101 from the sample cell 103, and the intake valve 111 is controlled to assume an open position to fluidly couple the source of testing gas 109 to the reference cell 101 in order to fill the reference cell 101 with testing gas at the predetermined elevated pressure of the test. After filling the reference cell 101 with testing gas, the intake valve 111 is controlled to assume a closed position to isolate the reference cell 101. Next, the valve control and interface module 133 performs a wait operation for a waiting time of approximately 200-

400 seconds in order to allow the temperature in the reference cell 101 to equilibrate with the ambient temperature and the sample cell temperature. Equilibration is necessary to make accurate measurements of the initial pressures in the cells. After expiration of the waiting time, the valve control and interface module 133 controls the intermediate valve 107 to assume an open position for a very short period of time (i.e., 0.1 seconds, which is sufficient to flow substantial amounts of the testing gas from the reference cell 101 into the sample cell 103. During this flow period, the pressure in the reference cell 101 falls rapidly, due to gas expansion from the reference cell 101 into the free volume of the sample cell 103. Next, the valve control and interface module 133 controls the intermediate valve 107 to assume a closed position that isolates both the reference cell 101 and the sample cell 103. After the intermediate valve 107 is closed, the gas pressure in the sample cell 103 begins to decrease at a slower rate due to diffusion of gas into the porous sample 129. These operations are referred to as the pressure decay stage and continue for the time period $T_{decay}$. Next, the valve control and interface module 133 controls the exhaust valve 115 to assume an open position that fluidly couples the sample cell 103 to the exhaust port 113 at atmosphere for a short period of time (e.g., 1-3 seconds) in order to drop the pressure of the sample cell 103 to atmospheric. Next, the valve control and interface module 133 controls the exhaust valve 115 to assume a closed position that isolates the sample cell 103. After the exhaust valve 115 is closed, the gas pressure in the sample cell 103 increases as gas diffuses out of the porous sample 129 into the interior space of sample cell 103. These operations are referred to as the degassing stage and continue for the time period $T_{degas}$. The pressure decay stage and the degassing stage (without the initial flushing) can be repeated multiple times (such as an additional two to three times).

During the pressure test of step 527 (particularly during the time period $T_{decay}$ of the pressure decay stage and during the time period $T_{degas}$ of the degassing stage), the data acquisition module 135 is configured to cooperate with the pressure sensor 117 and the temperature sensor 119 to measure and record the temperature and pressure of the reference cell 101 over time. The data acquisition module 135 is also configured to cooperate with the pressure sensor 121 and the temperature sensor 123 to measure and record the temperature and pressure of the sample cell 103 over time. Furthermore, the data acquisition module 135 is configured to cooperate with the temperature sensor 125 to measure and record the average temperature of the system over time.

In step 529, the data analysis module 137 is configured to extract the data segments corresponding to a respective pressure decay stage and subsequent degas stage of the pressure test of step 527 and shifts the data segments to the same starting time $t_0$. Time $t_0$ is dictated by the timestamp value for the time when the pressure of the sample cell 101 starts increasing after the intermediate valve 107 has been opened.

In step 531, the data analysis module 137 is configured to utilize the results of one or more calibration operations to transform the raw pressure and temperature values of the data segments of the pressure decay stage(s) and the pressure degas stage(s) as generated in step 529 to corrected values that compensate for systematic errors of the apparatus as described herein.

In step 533, the data analysis module 137 matches the corrected values of the data segments of the pressure decay stage(s) and the pressure degas stage(s) for the pressure test of step 527 to pressure curves (i.e., pressure data) generated by a computational model of the pressure decay stage(s) and pressure degas stage(s) with curve-related parameters α, β and τ. The computational model of step 533 assumes the particle size distribution as measured in step 527. The matching identifies the pressure curve that is best-fit to the corrected values of the data segments of the pressure decay stage(s) and the pressure degas stage(s) as generated in step 531. A minimum set of fixed parameters may be required to calculate the best fit. These fixed parameters can include i) the free volumes of the reference cell 101 and the sample cell 103 (i.e., the cell volume subtracting the volume of the billet(s) 127 in the sample cell 103; ii) the initial guess for the bulk sample volume; iii) parameters corresponding to the particle size distribution as measured in step 527; and iv) other necessary parameters for the computational model as needed. With all of the volumes (i.e., the volume $V_1$ of the reference cell 101, the volume $V_2$ of the sample cell 103, and the volume $V_b$ of the billet(s) 127) known, the values of the curve-related variables (e.g., β, α, τ) of the best-fit curve can be transformed into an estimation of bulk properties of the test sample 129, including bulk volume $V_{sample}$ of the test sample 129, porosity φ of the test sample 129, and permeability k of test sample 129. For example, the bulk volume $V_{sample}$ of the test sample 129 can be derived from Eqs. (28) and/or (29). The porosity φ of the test sample 129 can be derived from Eqs. (30) and/or (31A) and (31B). This porosity, derived from curve matching, can be further referred to as gas-probed porosity or pressure decay matrix porosity $\phi_m$. The permeability k of test sample 129 can be derived from Eq. (32). This permeability, derived from curve matching, can be further referred to as gas-probed permeability or matrix pressure decay permeability $k_m$. And the grain volume $V_{grain}$ of the test sample can be calculated from the bulk volume and the porosity from Eq. (32). Additional properties of the test sample can also be computed as follows.

The bulk density $\rho_b$ can be calculated using the total mass and bulk volume of the sample before crushing as:

$$\rho_{bulk} = M_{total}/V_{total}. \qquad (35)$$

The grain density $\rho_g$ can be calculated as:

$$\rho g = M_{sample}/V_{grain}. \qquad (36)$$

The effective gas-filled porosity $\phi_a$, which is based on the bulk density and grain density, can be calculated as:

$$\phi_a = 1 - \rho_{bulk}/\rho_s. \qquad (37)$$

Note that because the curve-related parameter τ (i.e., the diffusion relaxation time) is less than the time period $T_{decay}$ of the pressure decay stage, the final pressure equilibrium will be reached and the application of Boyle's law will allow accurate characterization of the total grain volume $V_{grain}$ of the test sample.

In step 535, the properties of the sample generated by the analysis of step 533 can be integrated together for visualization and data analysis operations as needed.

Note that for the case where curve-related parameter τ (i.e., the diffusion relaxation time) is slightly greater than the time period $T_{decay}$ of the pressure decay stage, it is possible to use the pressure extrapolated by the best fit model pressure curve at t=τ.

Also note that since all particle sizes are tested in combination, the permeability resulting from the interpretation of each pressure decay test is averaged through all permeability distributions inside all particle size ranges. Properties estimated from multiple repeats of pressure decay tests can be averaged, and the scatter of the properties estimated from multiple repeats can be utilized to characterize the precision of the measurement.

In some cases, when the tight operational schedule requires characterization of multiple samples with minimum testing time per sample, it is possible to apply the same procedure without iterative reduction of fragment size (i.e., without the iterative crushing of step 523 and the testing of steps 509 to 519). This requires good a-priori understanding of the range of rock properties in the tested batch, which allows testing of all samples in the batch after crushing them to the same known fragment size, estimated beforehand.

Note that generally the effective gas-filled porosity $\phi_a$ is greater than the matrix pressure decay porosity $\phi_m$, which indicates that only a portion of the initial pore volume in the test sample is visible by gas probing. There are two mechanisms that render part of the initial volume not visible to gas probing: 1) smaller particles may have very small diffusion time, and the portion of pore volume attributed to them is filled with gas too quickly to be recorded on the pressure curve; 2) typically the weakest surfaces in microporous materials removed during crushing correspond to local maxima of pore volume (for example, organic rich layers containing the bulk of the organic porosity and existing as interfaces between the mineral constituents); this portion of pores removed by crushing (which is related to total surface area generated by crushing) is lost for gas probing as well. In order to maximize the portion of pore volume visible to gas probing and compensate for these mechanisms, the mass fraction of small particles compared to large particles can be reduced. It is acknowledged that fragmentation by crushing is largely controlled by the natural strength fabric in the rock, which is out of control the of the operator. At the same time, a strict following of the crushing procedures and proceeding with an iterative reduction of particle size in small steps allows one to maximize the information extracted from a given sample. The best quality results are produced with the most narrow particle size distributions close to $R_{max}$. An important extension of this approach, which is especially important for high permeability material, is to test samples at their initial size, without any crushing. Any shape of the sample can be used (e.g. cylinder, cube, drill cuttings) if the effective size of the fragments can be estimated. Any size of the fragment that can fit into the sample cell of testing equipment (small dimension less than 1 inch (25.4 mm) most typical) can be used. In case of drill cuttings, which typically have their surface layer contaminated and altered by the invasion of drilling mud, it is important to remove this contaminated layer by either cleaning it chemically or by any other method that allows characterization of the intact material.

Another method that maximizes the portion of pore volume visible to gas probing and compensates for these mechanisms is to use different testing gas or liquid. Increasing the pore fluid viscosity by a factor of n will increase the testing time by the same factor, and make a portion of the fastest pore volume visible to the pressure decay probe. This method helps to mitigate the problem of too fast diffusion time or, equivalently, the visible pore volume reduction, but will not help in mitigating the loss of organic porosity due to crushing and removing the organic rich interfaces. The downside of this approach is that overall testing time increases by a factor of n. In addition, during the interpretation of results obtained on microporous materials using different gases or liquids it is necessary to take into account the difference in non-Darcy flow mechanisms and, potentially, effects of different rock-fluid interactions and molecular sieving effect.

It can be noted also that the extrapolated permeability, attributed to the portion of the pore volume not visible to the gas probe, should be higher than the permeability estimated on the visible portion of pore volume.

Figure 6:
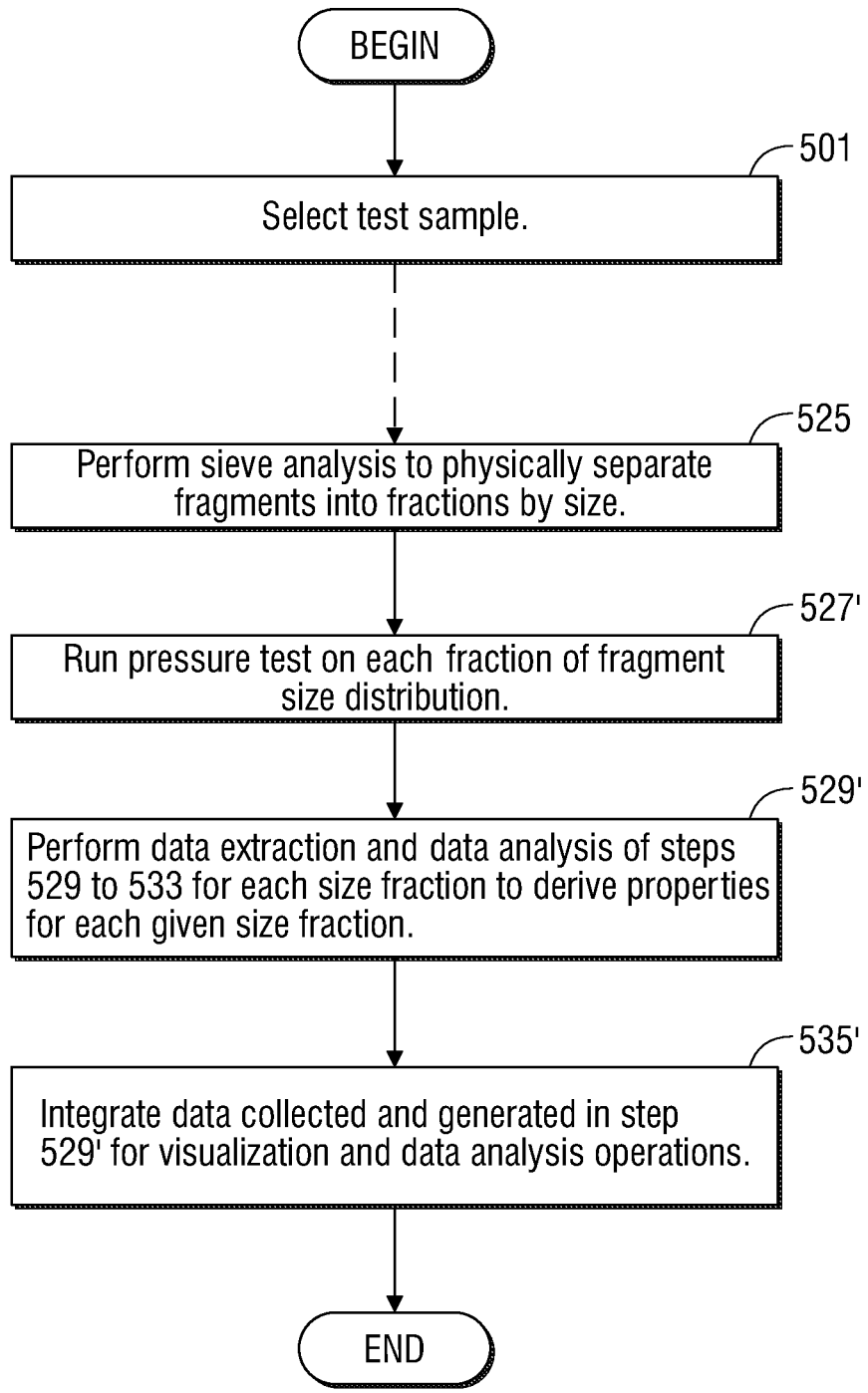
FIG. 6 is a flow chart of operations carried out by the apparatus of FIG. 2 that measures the distribution of different properties (e.g., permeability, porosity, and grain and bulk density) in a fragmented material.

The testing apparatus and methodology as described above can be adapted to perform an experiment that measures the distribution of permeability, porosity, and grain and bulk density in a fragmented material as shown in the flow chart of FIG. 6.

In this method, the operations of steps 501 to 523 are performed to ensure the fragmented material has a maximum particle size small enough to perform the pressure decay stage within the defined test time $T_{decay}$. If one or more of the steps have already been completed, they can be omitted as desired and the processing continues to step 525.

In step 525, sieve analysis is performed to physically separate the fragments of different sizes from one another and to measure the frequency of each respective fragment size within the particle size distribution of the fragments of the test sample produced by the crushing of step 507 and possibly step 523 as needed.

Then, in step 527' the pressure test of step 527 is run for each fraction of the fragment size distribution resulting from the crushing of step 507 and possibly step 523 as needed. The details of the pressure test of step 527 are described above.

Then, in step 529', the data extraction and analysis of steps 529 to 533 are performed on the data segments resulting from the pressure decay stage(s) and the pressure degas stage(s) of the pressure test for each fraction of the fragment size distribution.

For each fraction of the fragment size distribution, the data analysis of step 529' identifies the pressure curve that is best-fit to the corrected values of the data segments of the pressure decay stage(s) and the pressure degas stage(s) of the fraction. A minimum set of fixed parameters may be required to calculate the best fit. These fixed parameters can include i) the free volumes of the reference cell 101 and the sample cell 103 (i.e., the cell volume subtracting the volume of the billet(s) 127 in the sample cell 103; ii) the initial guess for the bulk sample volume; iii) parameters corresponding to the particle size of the fraction; and iv) other necessary parameters for the computational model as needed. With all of the volumes (i.e., the volume $V_1$ of the reference cell 101, the volume $V_2$ of the sample cell 103, and the volume $V_b$ of the billet(s) 127) known, the curve-related variables (e.g., $\beta$, $\alpha$, $\tau$) can be transformed into an estimation of sample-related properties, including porosity $\phi$ and permeability k of the test sample as a function of particle size. Additional properties of the test sample as a function of particle size can also be computed. Such additional properties can include the effective gas-filled porosity $\phi_a$ as a function of particle size, the matrix pressure decay porosity $\phi_m$ as a function of particle size, the matrix pressure decay permeability $k_m$ as a function of particle size, the bulk density $\rho_b$ as a function of particle size, and the grain density $\rho_g$ as a function of particle size.

In step 535', the properties of the test sample as a function of particle size as generated by step 529' can be integrated together for visualization and data analysis operations as needed.

Figure 7A:
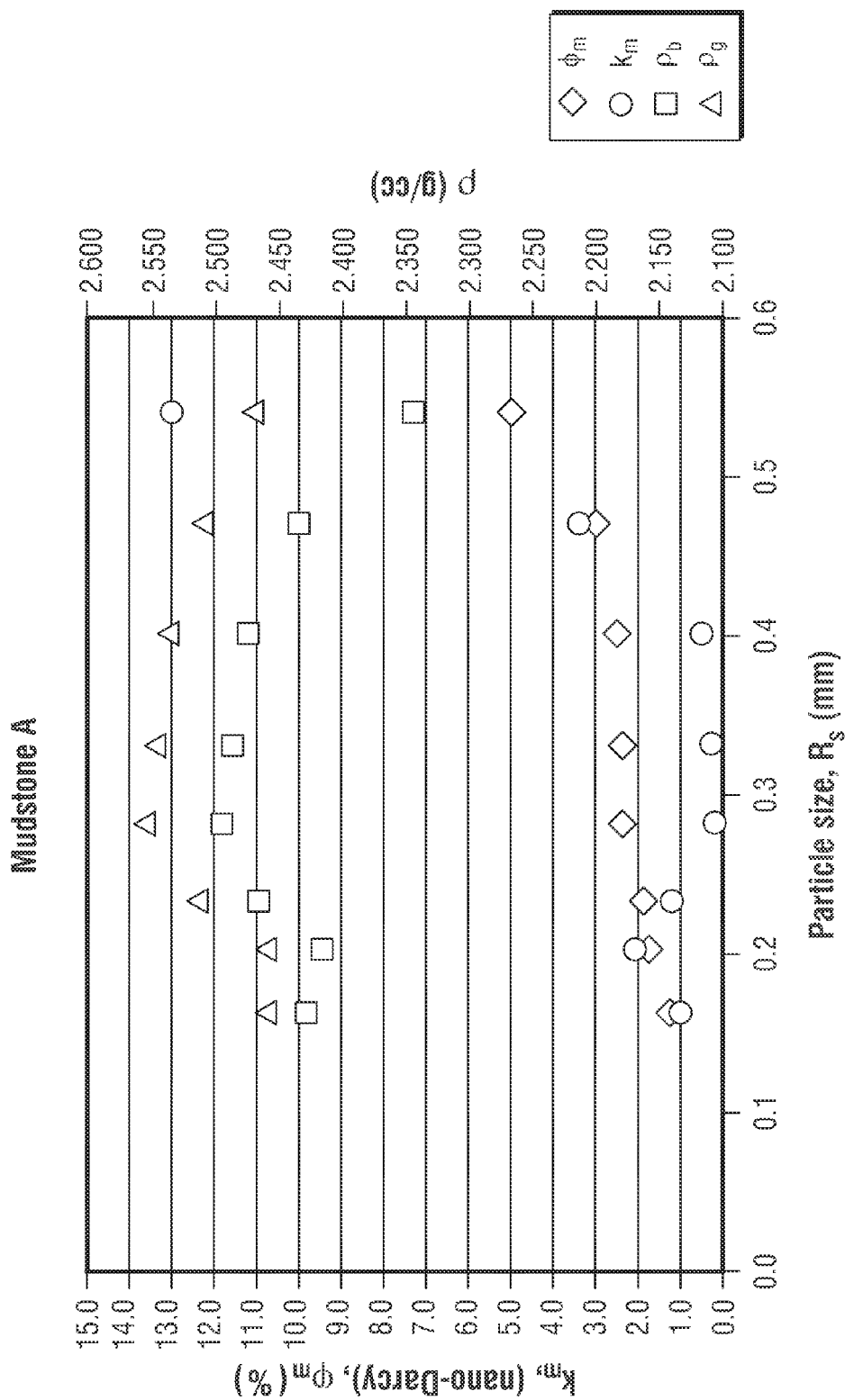

FIGS. 7A and 7B show an exemplary visualization produced in step 535' for two different heterogeneous rocks, where porosity, permeability, and bulk and grain density are plotted as functions of particle size. In this plot, in addition to the distribution of porosity and permeability in the test sample, the visualization also shows information about properties of the rock fabric. Bends on the $k_m(R_s)$ and $\phi_m(R_s)$ curves indicate that there are some intrinsic length-scales in the natural rock fabric. There are two length scales in the microstructure of 'Mudstone A' at $R_s=0.25$ mm and $R_s=0.45$ mm, suggesting that there are stronger inclusions with characteristic size between 0.5 and 0.9 mm ($2 \times R_s$), which have average porosity about 2.5% (total porosity of the sample based on bulk volume and grain volume comparison is about 7.1%), much lower permeability, and higher density than the rest of the crushed material. There is one length scale in 'Mudstone B' at $R_s=0.5$ mm. The increasing trend of $k_m(R_s)$ and nearly constant bulk density at $R_s>0.5$ mm suggest that there are scattered slit-shaped inclusions, with very high permeability, compared to the permeability of the rock matrix. As the number of these inclusions per particle grows, they contribute little to the increase in pore volume, but cause a large increase in the average permeability per particle. The average spacing of the inclusions is about $2 \times R_s = 1$ mm. The abundance of the large particles suggests that there is no large strength contrast between the inclusions and the surrounding material. One possible explanation of the described situation is the presence of scattered, thin, partially mineralized fractures with high conductivity and high strength.

Note that the distribution of bulk and grain densities as a function of fragment size, $\rho_b(R_s)$ and $\rho_g(R_s)$, carry more information on mechanical rock fabric than on transport rock fabric. For example, in Mudstone B, the increasing trend towards smaller sizes grain density and nearly flat bulk density indicate that the more surface area is created the more of light components in the rock composition is lost. This can be explained by more intensive disconnection and disappearing of organic matter from the mineral matrix during crushing. In Mudstone A, there is a clear peak of grain and bulk density which overlaps with 0.5 to 0.9 mm ($2 \times R_s$ length-scale in the permeability distribution. The peaks confirm the existence of two types of material in the initial rock, which could possibly be realized by different depositional laminae.

For analysis of the overall permeability distribution in the test sample, it is useful to generate a visualization, which will indicate the breakdown of all pore volume present in the rock, in terms of the permeability of each fraction of pore volume. This assessment is valid regardless of the strength fabric of the rock, which often reveals itself in the distribution of fragment properties as a function of particle size. The generation of the permeability distribution per pore volume fraction is done as follows.

First, the incremental pore volume per particle size fraction ($\Delta \phi_m(R_s)$) is calculated as:

$$\Delta \phi_m(R_s) = \phi_m(R_s) \cdot \Delta m(R_s), \quad (38)$$

where $\Delta m(R_s)$ is the normalized mass fraction of the given particle size, $$1 = \sum_{R_s=R_{min}}^{R_s=R_{max}} \Delta m(R_s). \quad (39)$$

In this case $\Delta \phi_m(R_s)$ is normalized by the sample bulk volume.

Second, the pairs of $k_m(R_s)$, $\Delta \phi_m(R_s)$ are reordered towards ascending permeability.

Third, the cumulative normalized pore volume $$\sum_{k_i < k_m} \Delta \phi_m(k_i)$$

is plotted as a function of $k_m$.

Figure 8A:
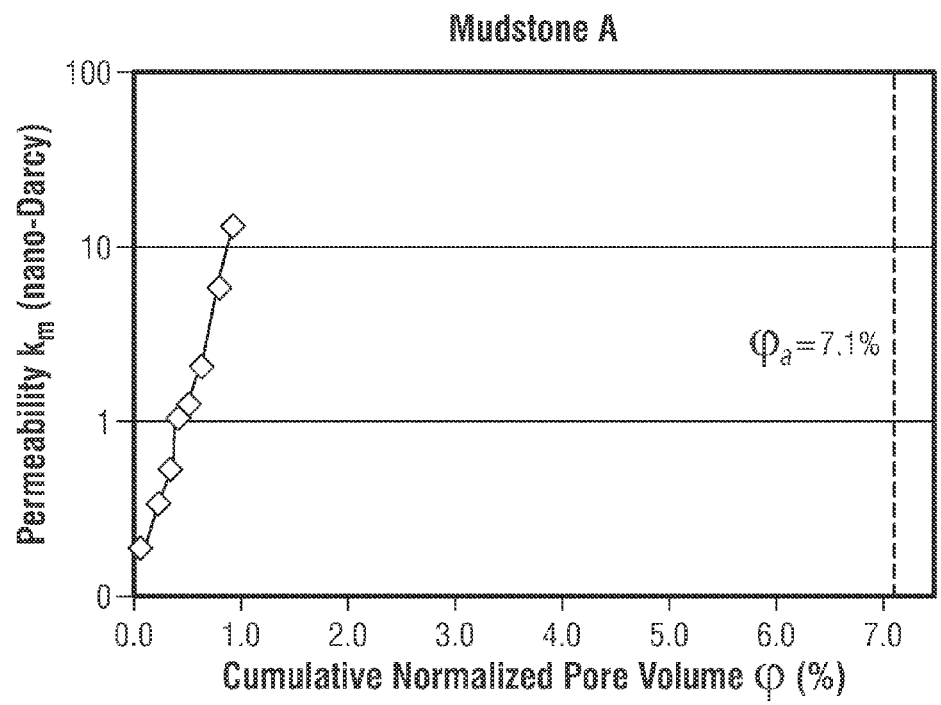
FIGS. 8A and 8B show another exemplary visualization for two different heterogeneous rocks (Mudstone A and Mudstone B), respectively, where the permeability of the rock is plotted as a function of normalized pore volume. It also shows the effective gas-filled porosity $\phi_a$ of the rock calculated as the normalized difference of bulk volume and grain volume.
Figure 8B:
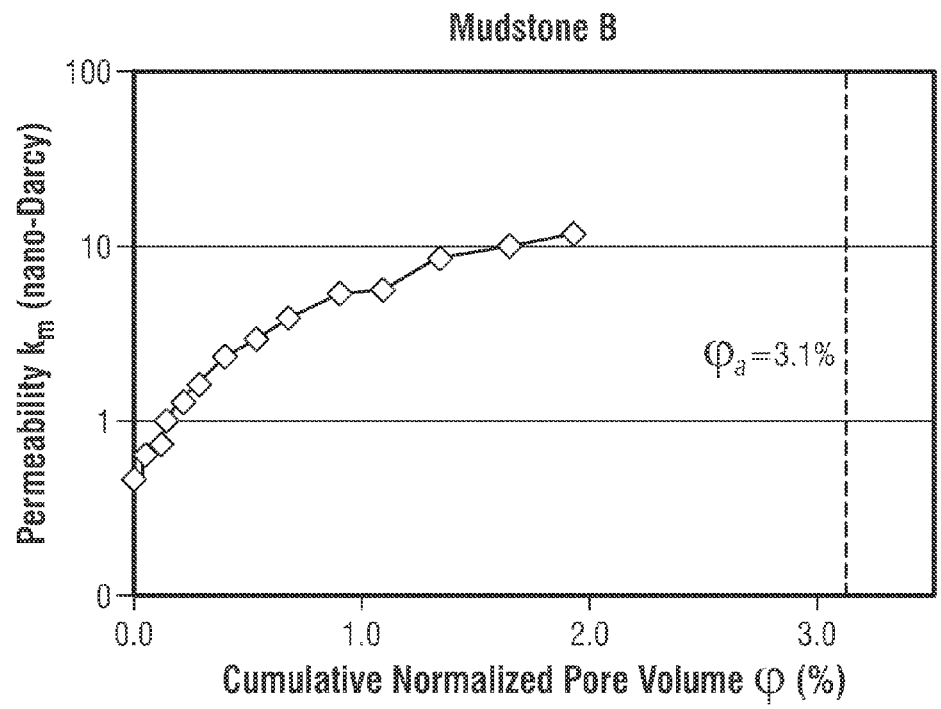

An example of the results of the third step is shown in FIGS. 8A and 8B for two different mudstones A and B. These plots also show the effective gas-filled porosity $\phi_a$ calculated as the normalized difference of bulk volume and grain volume. The comparison of the maximum cumulative gas-probed porosity and the density-based porosity is indicative of the overall coverage of gas probing. The achieved coverage for 'Mudstone A' is about 15% of the pore volume. This is the worst case scenario, which happened because of the weak rock fabric and too low initial crushed particle target size. The achieved coverage for 'Mudstone B' is about 65% of the pore volume and is in the normal range.

Figure 9A:
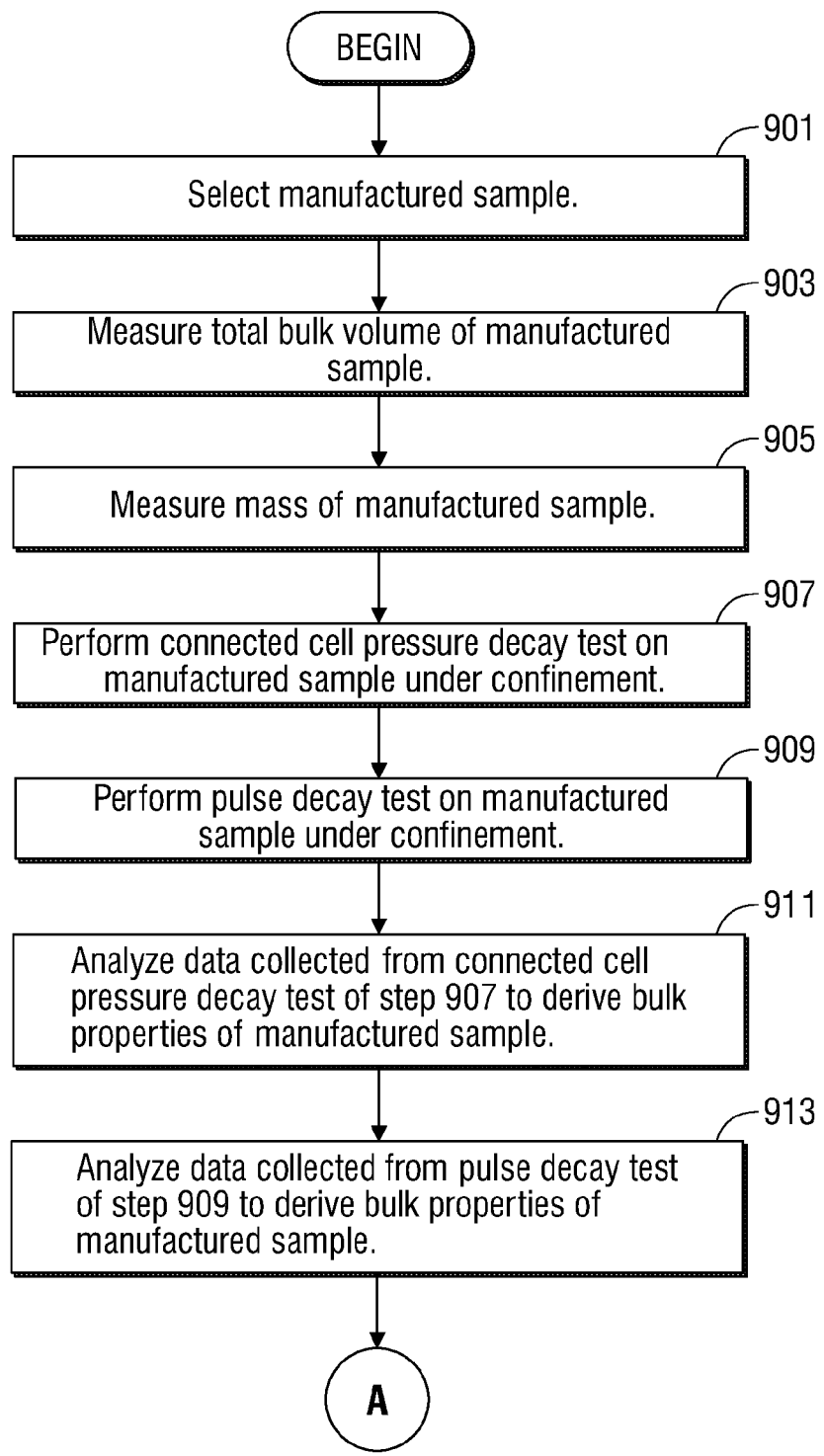
FIGS. 9A-9C are a flow chart of operations carried out by the apparatus of FIG. 10 and the apparatus of FIG. 2 to measure a bulk property as well as a property distribution for a number of properties (e.g., permeability, porosity, and grain and bulk density) in a manufactured sample of microporous material.
Figure 9B:
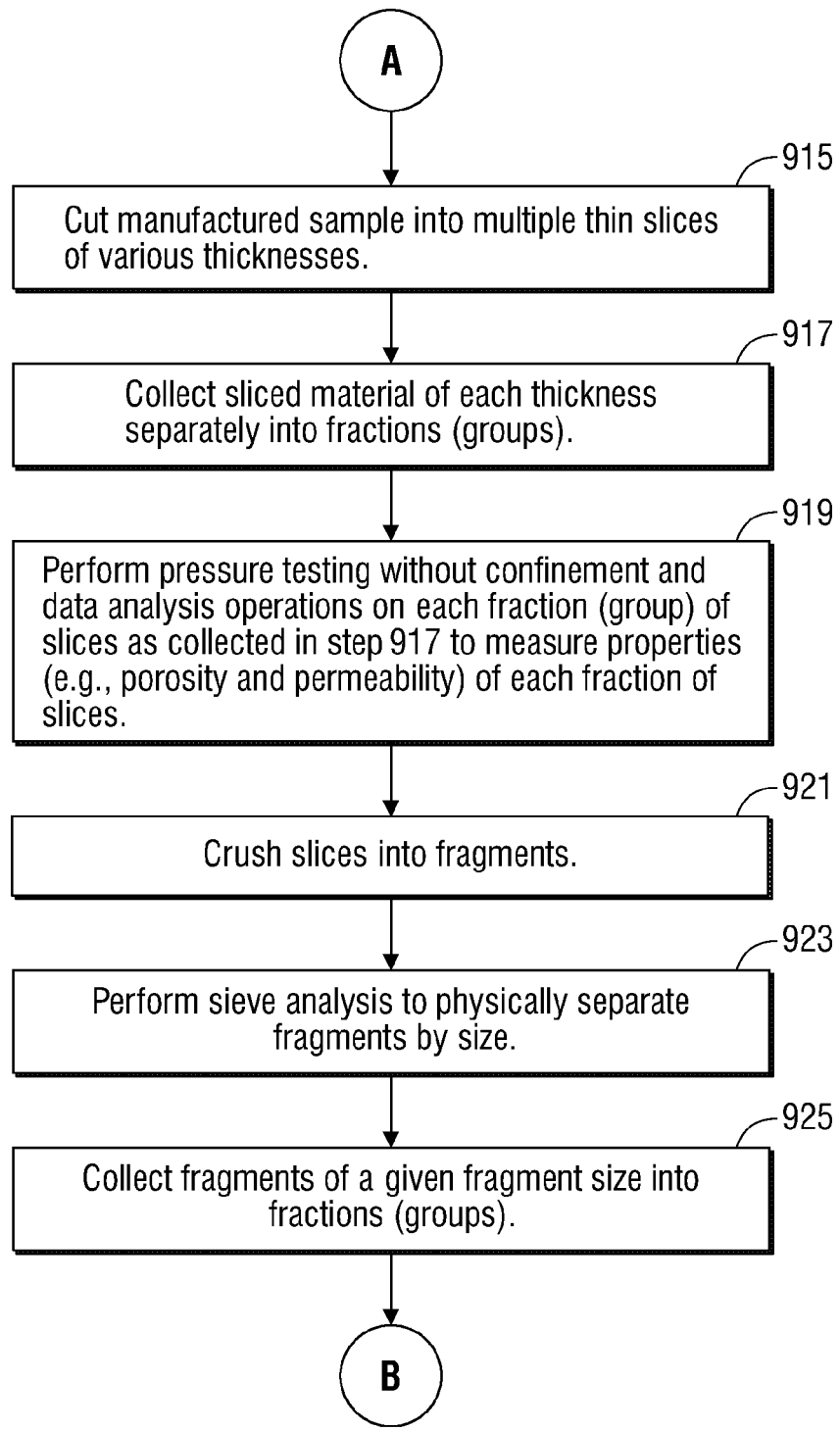
Figure 9C:
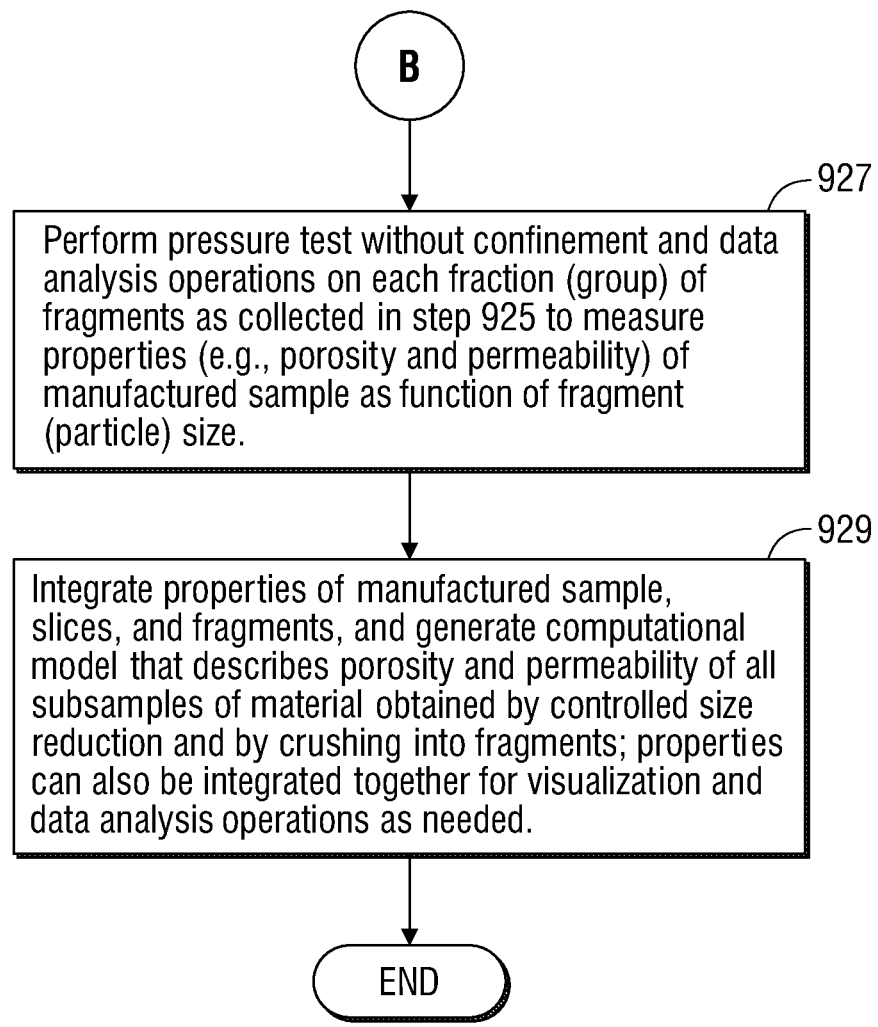

The testing apparatus and methodology as described above can be adapted to perform an experiment that measures the distribution of permeability, porosity, and other properties in a manufactured sample as shown in the flow chart of FIGS. 9A to 9C. The manufactured sample has a controlled shape. For example, it can be a cylindrical plug, wafer, or a rectangular slab. The manufactured sample is cut or otherwise divided into pieces (e.g., slices of variable thickness) for testing. The pieces may be subsequently crushed into fragmented material for testing of the crushed material.

In one embodiment where the manufactured sample is a plug, the minimum amount of material that can be tested is about 1 inch (25.4 mm) diameter×2 inch (50.8 mm) long cylindrical plug, which is typically enough to produce from four to seven data points on the length scales varying from 1 to 0.05 inches (25.4 to 1.3 mm). In other embodiments, the minimum of material should be enough to prepare at least three different sizes of fragments, at least 30 grams of material each. In order to do both type of tests with the controlled size reduction and size reduction by fragmentation on the same rock, the amount of material must be doubled or tripled. Other, non-cylindrical shapes can be used as well if used for unconfined pressure decay testing only; however cylindrical shape provides multiple advantages such as convenient size reduction by slicing and the possibility of testing samples under confinement.

If there is a-priori information about the direction of lowest variability in properties, the axes of plugs can be oriented in a predetermined manner during the cutting to provide the minimum variability along their axes. For example, in case of finely laminated microporous rocks, samples will be aligned parallel to the horizontal bedding planes. In this orientation, by cutting slices perpendicular to the bedding planes, the probing of different sizes is predominantly characterizing the intrinsic distribution of permeabilities in the sample, which are about proportionally represented in each slice. Alternatively, the slicing can be performed parallel to the bedding planes. In this case, the probing of differently sized subsamples is predominantly characterizing the spatial distribution of permeabilities in the bedding planes (i.e., the set of rock laminae).

In this method, in step 901, the manufactured sample is selected for testing.

In step 903, the total bulk volume of the manufactured sample is measured using a standard water immersion or mercury immersion method. Direct measurements of dimensions of the test sample can be performed using a vernier caliper, micrometer, or equivalent and the geometric volume of the test sample can be calculated from the measured dimensions. The geometric volume can be used for quality control of the immersion measurement for measuring the total bulk volume of the manufactured sample.

In step 905, the mass of the manufactured sample is measured.

Figure 10:
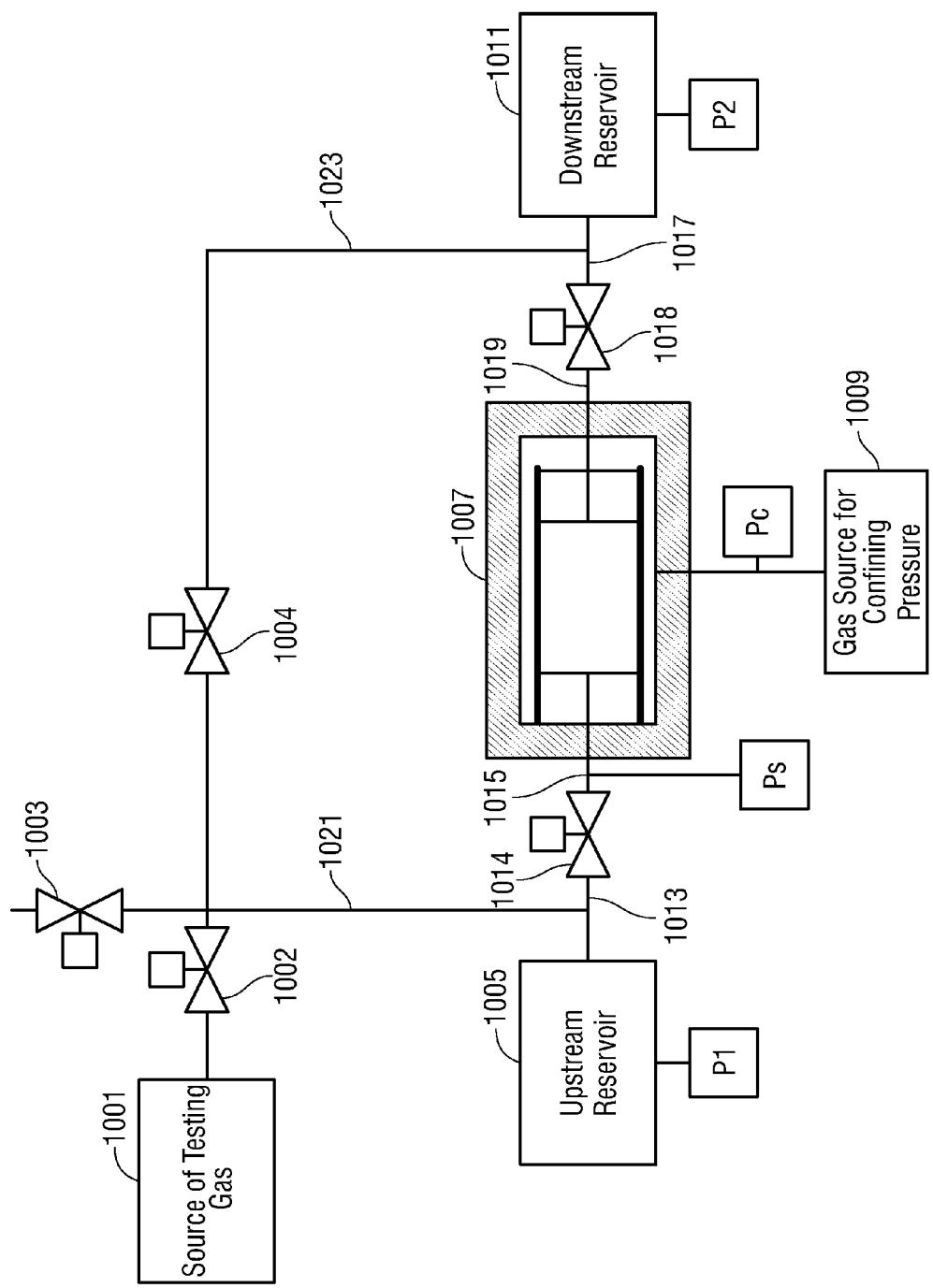
FIG. 10 is a schematic diagram of a pulse decay testing apparatus in accordance with the present application.

In steps 907 and 909, a pressure decay test followed by a pulse decay test are performed on the manufactured sample under confinement using a modified pulse decay test apparatus as shown in FIG. 10. This apparatus includes a source of testing gas 1001 (which is a low viscosity chemically inactive gas such as helium or nitrogen) that is fluidly coupled to an upstream reservoir 1005 of volume $V_1$, a sample holder 1007 that defines a closed volume that holds the manufactured sample and is capable of applying confining stresses (typically isostatic) to the manufactured sample as dictated by a gas or liquid source 1009 and measured by a pressure sensor $P_c$, and a downstream reservoir 1011 of volume $V_2$. A pressure transducer P1 measures the absolute pressure of the upstream reservoir 1005. A pressure transducer P2 measures the absolute pressure in the downstream reservoir 1011. An upstream flow line 1013 with inline valve 1014 is fluidly coupled between the upstream reservoir 1005 and the inlet 1015 of the sample holder 1007. A downstream flow line 1017 with an inline valve 1018 is fluidly coupled between the outlet 1019 of the sample holder 1007 and the downstream reservoir 1011. A pressure transducer Ps measures the absolute pressure inside the closed volume of the sample holder 1007 that contains the manufactured sample. A fill valve 1002 is fluidly coupled to the outlet of the gas source 1001. An upstream fill supply line 1021 is fluidly coupled between the fill valve 1002 (and a vent valve 1003 to atmosphere) and the upstream flow line 1013 (upstream of the valve 1014). A downstream fill supply line 1023 with inline valve 1004 is fluidly coupled between the fill valve 1002 (and the vent valve 1003) and the downstream flow line 1017 (downstream of the valve 1018). The fill valve 1002, vent valve 1003 and valves 1014, 1004, and 1018 are electronically controlled by a test controller similar to the testing apparatus of FIG. 2. $V_1$ is the total upstream volume, which includes the internal volumes of the upstream reservoir 1005, the chamber of the pressure transducer P1, the connecting lines to the pressure transducer P1 and valves 1014, 1004, the fill valve 1002, the vent valve 1003, and the upstream dead volume $V_{du}$ (which is the volume inside valve 1014, the upstream end plug of the sample holder 1007, and the pressure sensor $P_s$). $V_2$ is the total downstream volume, which includes the internal volumes of the downstream reservoir 1011, the chamber of the pressure transducer P2, the connecting line to valve 1004, and the downstream dead volume $V_{dd}$ (which is the volume inside valve 1018 and the downstream end plug of the sample holder 1007). The volumes $V_1$, $V_2$, $V_{du}$ and $V_{dd}$ can be found from calibration using Boyle's Law techniques.

In the pressure decay test of step 907, the pore volume of the manufactured sample is filled with testing gas to a pore pressure typically between 100 and 2,000 psig (7.03 and 140.6 kg/square cm gauge), which is required as an initial condition for the subsequent pulse decay testing. Pressure-time data during this filling stage, which is conceptually similar to a pressure decay test performed under confinement, is recorded and then interpreted to estimate bulk properties of the manufactured sample. Initially, valves 1014, 1004, and 1018 are open, all other valves are closed, pressures recorded by transducers P1 and P2, which are equal through this stage as long as valve 1004 is open, are stabilized and therefore indicate the initial (low) pressure throughout the system and inside the pore volume of the sample. Then, valves 1014 and 1018 are closed and valve 1004 remains open. The fill valve 1002 is opened to fill both the upstream reservoir 1005 and the downstream reservoir 1011 to a pressure typically equal to or slightly above the target pore pressure for pulse decay testing. After equilibrium is reached and initial (high) pressure in the reservoirs 1005 and 1011 is recorded, valves 1014 and 1018 are simultaneously opened and testing gas is allowed to flow from the reservoirs to fill the pore volume of the manufactured sample held within the sample holder 1007. The fill period should allow adequate time for the testing gas to diffuse into the (typically) low-permeability manufactured sample. The absolute pressure of the upstream and downstream reservoirs 1005 and 1011 is monitored until no further change is observed, indicating thermal and pressure equilibrium. The flow regime in this stage is equivalent to the flow regime in the isolated cell pressure decay testing (gas flows from outside of the sample into the pore volume of the sample), except that the volume with elevated initial pressure and low initial pressure are not isolated, but connected throughout the test. This test can be referred to as the connected cell pressure decay test.

After the connected cell pressure decay test of step 907 is complete, the final pore pressure in the manufactured sample is increased as necessary such that the pore pressure in the manufactured sample is stabilized at the target pulse decay pore pressure $P_2[0]$. Then, the pulse decay test of step 909 is started. At least valves 1014 and 1004 are closed, and the fill valve 1002 is opened to increase pressure in the upstream reservoir 1005 by Op, which is typically 2 to 20 percent of $P_2[0]$, and then closed. After the pressure in the upstream reservoir 1005 becomes stable, valve 1014 and valve 1018 are opened to initiate the pressure-transient portion of the test. The output of the pressure transducers P1, P2 for the upstream and downstream reservoirs can be monitored as a function of time. Temperature sensors can also be used for measuring temperatures of the upstream reservoir 1005, the downstream reservoir 1011, the closed volume of the sample holder 1007 and ambient temperature as needed similar to the configuration of the testing apparatus of FIG. 2.

In step 911, the data collected from the connected cell pressure decay test of step 907 can be analyzed to measure bulk properties of the manufactured sample under confinement. Such properties can include pressure decay porosity, pressure decay permeability, and grain volume of the manufactured sample under confinement. The data analysis of step 911 can involve operations similar to the data analysis methodology described above for interpretation of isolated cell pressure decay test results. Specifically, the data analysis can identify the best matching curve-related variables (e.g., $\beta$, $\alpha$, $\tau$) as described above. The bulk volume of the manufactured sample, $V_{sample}$, is known from the pre-test measurements and is not identified from the pressure-time data. The pressure decay porosity, permeability, and grain volume of the manufactured sample under confinement can be estimated using the same Eqs. (30), (31A), (31B), (32) and (33), where the sample cell volume in the isolated cell pressure decay testing is replaced by a sum of upstream and downstream volume of the modified pulse decay system ($V_1$ and $V_2$), plus the volume inside valve 1004.

It is also contemplated that the connected cell pressure decay test of step 907 can fill the pore volume to a target pulse decay pore pressure by flowing the testing gas from the upstream side (valves 1014 and 1004 open, valve 1018 closed) or from the downstream side (valves 1018 and 1004 open, valve 1014 closed). In this case, the upstream (or downstream) pressure decay porosity, upstream (or downstream) pressure decay permeability, and grain volume of the manufactured sample can be estimated using the same Eqs. (30), (31A), (31B), (32) and (33), where the sample cell volume in the isolated cell pressure decay testing is replaced by a sum of upstream volume and downstream dead volume $V_1+V_{dd}$ minus the volume of valve 1018 for the upstream case (or minus volume of valve 1014 for the downstream case).

In step 913, the data collected from the pulse decay test of step 909 can be analyzed to derive the fabric permeability of the manufactured sample under confinement. Fabric permeability, which is a result of pulse decay testing that implements flow of gas through the sample from upstream to downstream reservoir, can be different from pressure decay permeability, which is a result of pressure decay testing that implements a different regime of gas flow, which happens from outside of the sample into the pore volume, in the case of heterogeneous samples. In the case of homogeneous samples fabric permeability and pressure decay permeabilities are the same. In the case of heterogeneous samples fabric permeability tends to reflect the properties of highest permeability channels in the sample's pore network system with higher weight, while pressure decay permeability reflects properties of all conductivity channels connecting the pore network to the outside equally. Such data analysis operations can be based on the solution of the diffusivity equation derived by combining the differential form of Darcy's Law with the continuity equation. The manufactured sample is presumed to be initially at a uniform pore pressure throughout. Then at time t=0, a pulse of slightly higher pressure, $\Delta p$, is applied to its upstream end from the upstream reservoir 1005. As the gas flows from upstream reservoir 1005 into the manufactured sample, the pressure in the total upstream volume $V_1$ ($P_1[t]$) declines. The pressure in the total downstream volume $V_2$ ($P_2[t]$) remains constant for a short period of time until the pressure pulse has traversed the length of the manufactured sample. Then the pressure $P_2[t]$ rises. Because $P_1[t]$ declines and $P_2[t]$ rises, the differential pressure between the upstream and downstream reservoir over time ($\Delta p[t]$) continues to diminish and gradually approaches zero as the upstream and downstream pressures become equal. The rate of pressure decay depends on the fabric permeability of the sample, i.e. the lower the permeability the slower the decay.

The fabric permeability $k_f$ of the manufactured sample at certain pore pressure of pulse decay testing can be derived from the data of the pulse decay test, with assumption that compressibility of upstream and downstream volumes with pressure is negligible, as follows:

$$k_f = -\text{slope} \cdot \frac{\mu_{gas} C_{gas} L}{f_1 A \left(\frac{1}{V_1} + \frac{1}{V_2}\right)}, \tag{40}$$

where $\mu_{gas}$ is viscosity of the testing gas,
$C_{gas}$ is compressibility of the testing gas,
L is length of the sample along the direction of gas flow,
A is the cross-sectional area of the sample perpendicular to the direction of gas flow,
$V_1$ and $V_2$ are upstream and downstream volumes, $$f_1 = \frac{\theta_1^2}{a+b}, \tag{41}$$

$\theta_1$ is the first root of the equation $\tan \theta = \frac{(a+b)\theta}{\theta^2 - ab}$, (42)

$$a = \frac{V_p}{V_1} \text{ and } b = \frac{V_p}{V_2}$$

are upstream and downstream storage coefficients, (43)

$V_p$ is pore volume of the sample, $V_p = \phi \cdot A \cdot L$, (44)

$\phi$ is porosity of the sample (which can be derived by data analysis in step 911 from the pressure decay test of step 907, or it can be derived from the intercept of the linear slope of pulse pressure logarithm defined by $A_0$ in Eq. (45), or defined using any other possible method to define bulk porosity of the manufactured sample), and slope is defined as the slope of the linear regression to the linear portion of the experimental curve controlled by the logarithm of differential pulse decay pressure as $$\ln\left(\frac{\Delta p[t] \cdot P_2[t]}{\Delta p[0] \cdot P_2[0]}\right) = A_0 + \text{slope} \cdot t. \tag{45}$$

In step 915, the manufactured sample can be cut into multiple thin slices of various thicknesses, using a diamond wire saw, or any other alternative method capable of creating thin parallel slices of the manufactured sample with minimum alteration of the cut surfaces. To ensure that the surfaces of the sample in each slice are parallel, a sample holder can be used and the first slice can be discarded in the event that it is not perfectly parallel.

In step 917, after the amount of sliced material of a given thickness satisfies the minimum material requirements for pressure testing, the sliced material of each given thickness is collected separately for further pressure testing (step 919).

Steps 915 and 917 can be repeated to collect groups of slices where the slices of each group have a common thickness. The thickness of the slice groups can be increased in steps according to a desired length-scale sampling.

In step 919, the slices of a given group (which share a common thickness) are loaded into the sample cell of the testing apparatus of FIG. 2, which is operated to carry out pressure tests without confinement and data analysis operations in the manner described above in order to measure properties of the slices of the group, including porosity and permeability of such slices. The common thickness of the slices of the group is used as the characteristic size of the sample in the analysis of the test. The pressure testing and data analysis operations of step 919 can be repeated for each group of slices as collected in the operations of steps 915 and 917.

In step 921, crushing equipment is configured such that the target size of the fragments produced by the crushing equipment is slightly below the initial thickness of the one or slices, and the slices are crushed by crushing equipment into fragments at the target size.

In step 923, sieve analysis is performed to physically separate the fragments of different sizes from one another and to measure the frequency of each respective fragment size within the particle size distribution of the fragments produced by the crushing of step 921.

In step 925, after the amount of fragmented material of a given size satisfies the minimum material requirements for pressure testing, the fragmented material for the given size is collected separately for further pressure testing (step 927).

Steps 921 to 925 can be repeated to collect fragmented material of different sizes. The sizes of the fragmented material can be increased in steps according to a desired size-scale sampling.

In step 927, the fragments of a given size are loaded into the sample cell of the testing apparatus of FIG. 2, which is operated to carry out pressure testing without confinement and data analysis operations in the manner described above in order to measure properties of the fragments, including sample volume, porosity, and permeability of such fragments. For example, the sample bulk volume, porosity, permeability, and sample grain volume of such fragments can be estimated using Eqs. (28), (29), (30), (31A), (31B), (32) and (33) as described above. The characteristic size of the fragments is used as the characteristic size of sample in the analysis of the test. The pressure testing and data analysis operations of step 927 can be repeated for each given size (fraction) of fractures collected in the repeated operations of steps 921 and 925.

The pressure testing and data analysis operations of step 927 allows for computation of properties of the manufactured sample as a function of fragment (particle) size, including porosity $\phi$ and permeability k of the manufactured sample as a function of fragment (particle) size. Additional properties of the test sample as a function of particle size can also be computed. Such additional properties can include the effective gas-filled porosity $\phi_a$ as a function of particle size, the matrix pressure decay storage $\phi_m$ as a function of particle size, the matrix pressure decay permeability $k_m$ as a function of particle size, the bulk density $\rho_b$ as a function of particle size, and the grain density $\rho_g$ as a function of particle size.

In step 929, the properties of the confined manufactured sample and slices resulting from the pressure decay test and the pulse decay test of steps 907 and 909, respectively, as well as the properties of the unconfined slices and crushed fragments resulting from the pressure tests of steps 919 and 927 can be integrated together and analyzed to identify a multiple-porosity and multiple-permeability computational material model that describes porosity and permeability of all subsamples of the material obtained by controlled size reduction and by crushing into fragments. Multiple-porosity multiple-permeability model assumes that total porosity of the material is subdivided into two to n pore subsystems. Each of the pore subsystems is characterized by its own porosity; sum of the porosities of all subsystems is equal to the total porosity. Each of the pore systems is characterized by its own permeability; value of permeability is decreasing with the index of the pore system. Pore systems can be connected with each other in various ways; interaction between pore systems is defined by connectivity parameters. In one embodiment, the computational model is identified as the computational material model with a minimum number of parameters that successfully fits the measurements for all sizes of slices and samples and assumes that all parameters such as porosities, permeabilities, and connectivities of pore subsystems, are uniformly distributed throughout the manufactured sample, i.e. does not depend on space coordinates. After the computational material model that best describes all observed responses of the tested material in the lab is established and parameters of this model are estimated, the model can be used in the commercial fluid flow simulators such as ECLIPSE, available from Schlumberger Technology Corporation of Sugar Land, Tex., USA, or others to predict fluid flow at different scales, using simulated domains of different size and geometry, using different flow regimes and boundary conditions.

In step 929, the properties of the manufactured sample as a function of particle size as generated in step 919 (properties of slices derived by controlled size reduction) and in step 929 (properties of fragments derived by crushing) can be integrated together for visualization and data analysis operations as needed. Controlled size reduction is not sensitive to the presence of strength fabric in the sample, and only reveals length scales of permeability fabric. Permeability distribution on the crushed fragments is sensitive to both permeability and to the rock strength fabric. Comparison of the two distributions indicates if the permeability and strength fabric are overlapping or are independent from each other in the initial sample. The permeability distribution of the crushed fragments also gives more details on the fine scale variability of the low-end matrix permeability of the sample and on the breakdown of this low-end permeability distribution in relation to the pore volume and the bulk volume of the initial sample.

Figure 11:
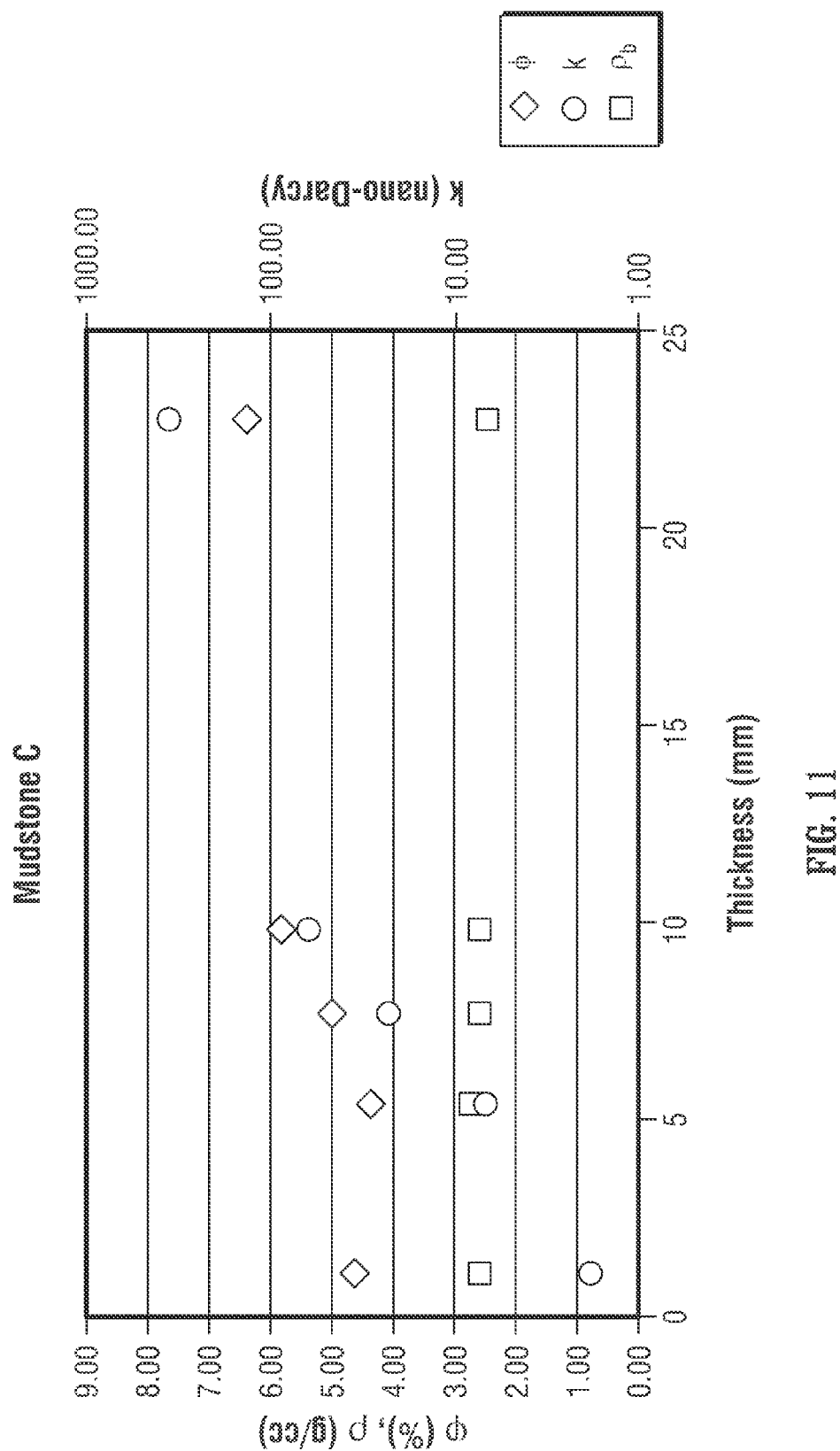
FIG. 11 is a plot of a number of different material properties measured by the pressure testing and data analysis operations of FIGS. 9A-9C for groups of slices with different thickness as cut from an exemplary manufactured sample of microporous material (in this case, a cylindrical plug of Mudstone C).

FIG. 11 shows an example of properties of unconfined material measured by the pressure testing and data analysis operations of step 919 on groups of slices with different thickness as cut from an exemplary manufactured sample (in this case, a cylindrical plug of Mudstone C). Note that due to the presence of highly conductive network connecting low permeability matrix elements (which are much smaller than characteristic size of the slices), the measured permeability of the slice groups grows with slice thickness.

In alternate embodiments, the operations of steps 915 to 919 can be adapted to test other controlled shapes of material in the manner similar to the slices as described above.

In other alternate embodiments, the measurements and analyses of the connected cell pressure decay test of step 907 and the pulse decay test of step 909 can be carried out at different levels of confinement stress (by varying the pressure of the gas source 1009) in order to evaluate the sensitivity of the measured properties to varying confinement stress.

In yet another alternative embodiments, the measurements and analyses of the connected cell pressure decay test of step 907, the pulse decay test of step 909, and the unconfined pressure tests of steps 919 and 927 can be carried out at different pore pressures in order to evaluate the sensitivity of the measured properties to varying pore pressure (particularly for the dependence of apparent permeability related to Knudsen flow regimes).

In yet other alternative embodiment, the measurements and analyses of the connected cell pressure decay test of step 907, the pulse decay test of step 909, and the unconfined pressure test of steps 919 and 927 can be carried out using different testing gases or liquid in order to characterize pore throat sizes, molecular sieving, adsorption, and wettability effects.

Note that the manufactured sample as described above can be prepared by covering one or more selected surfaces (or selected parts of the surfaces) of the samples by an impermeable material (such as epoxy or other suitable material) in order to selectively seal some of the flow directions to measure permeabilities in different directions, such as azimuthal permeability measurements along the bedding planes or transverse measurements perpendicular to the bedding planes. Another usage of the selective coating of the surfaces of the sample is to minimize the dead volume in the sample cell to increase signal-to-noise ratio. In this case the coating has to be sufficiently thick, have accurately measured volume, and closely repeat the internal surface of the testing cell, providing both minimum gap between the coated sample and the internal surface of the cell and allowing for easy loading and unloading of the sample.

When testing of the manufactured samples in the modified pulse decay system under confinement is impractical (for example, the shape of the manufactured sample is not cylindrical, or the shape is cylindrical but length is too short to apply confinement, or confinement cannot be applied due to low strength of the sample, or for any other reason), the operations of step 909 can be omitted.

It is well established both experimentally and theoretically that apparent gas permeability increases as the mean gas pressure decreases. The critical parameter that controls this change of permeability is the ratio of the free mean path of gas molecules 2 at current conditions to the width of flow channels w, known as Knudsen number, $K_n$. When $K_n$ is substantially above zero, the gas flow regime is also known as Knudsen flow; the increase of apparent permeability with the decreasing pressure (which in turn increases KO is known as slippage effect. In case of high pressures and wide channels $K_n \ll 1$, the slippage effect can be neglected and the apparent gas and fluid permeabilities are the same.

In the range of small but non-negligible $K_n$, the first-order correction to permeability was proposed by Klinkenberg:

$$\frac{k}{k_0} = \left(1 + \frac{b}{P}\right), \qquad (46)$$

where k is apparent gas permeability,
$k_0$ is zero slip (infinite pressure) permeability,
P is mean gas pressure, and
b is the Klinkenberg factor.

Originally, this relationship was developed to describe steady-state flow in cylindrical sandstone plugs, which typically have pore sizes and channel widths above tens of micrometers. In case of microporous materials smaller pore sizes (for example, shales often have nanometer scale porosity), $K_n$ cannot be considered small and higher-order corrections may need to be introduced to accurately describe k(P). For example, a double slip model can be used of the form:

$$\frac{k}{k_0} = \left(1 + \left(\frac{b}{P}\right)^2 \frac{L_{KE}}{\lambda}\right), \qquad (47)$$

where b is the double-slip constant,
$\lambda$ is the free mean molecule path, and
$L_{KE}$ is the second length-scale of the flow associated with the kinetic energy of bouncing back gas molecules after collisions with capillary walls.

Other models that characterize k(P) can also be used.

Natural microporous materials can be extremely heterogeneous and may have a quite complex spectrum of pore sizes and shapes, which can result in apparent permeability behavior that can be unique for different types of materials and different from both Eqs. (46) and (47). Therefore it requires direct measurement of apparent permeability as function of gas pressure.

Figure 13A:
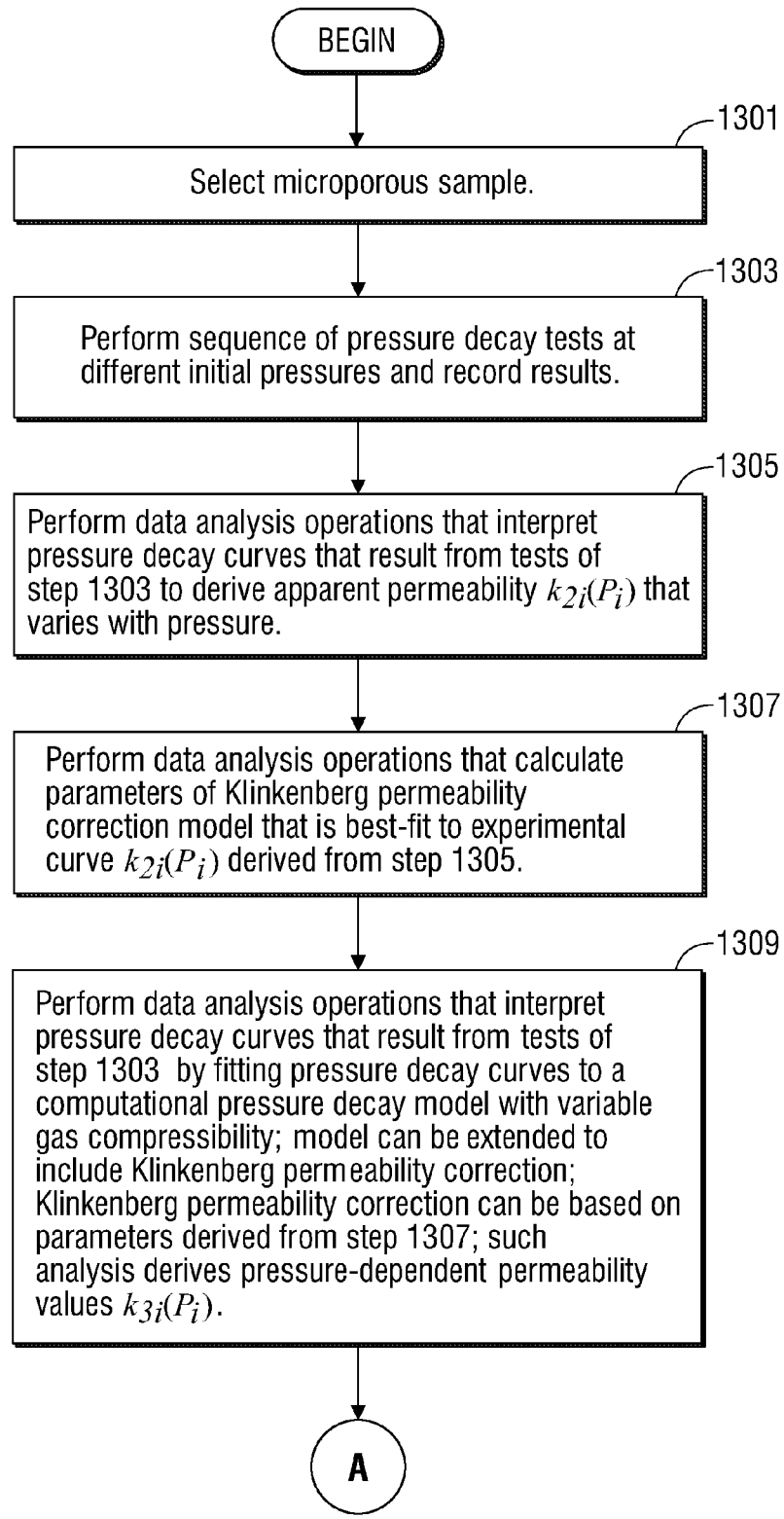
FIGS. 13A and 13B are a flow chart of operations carried out by the apparatus of FIG. 2 to measure the apparent permeability of a microporous sample.
Figure 13B:
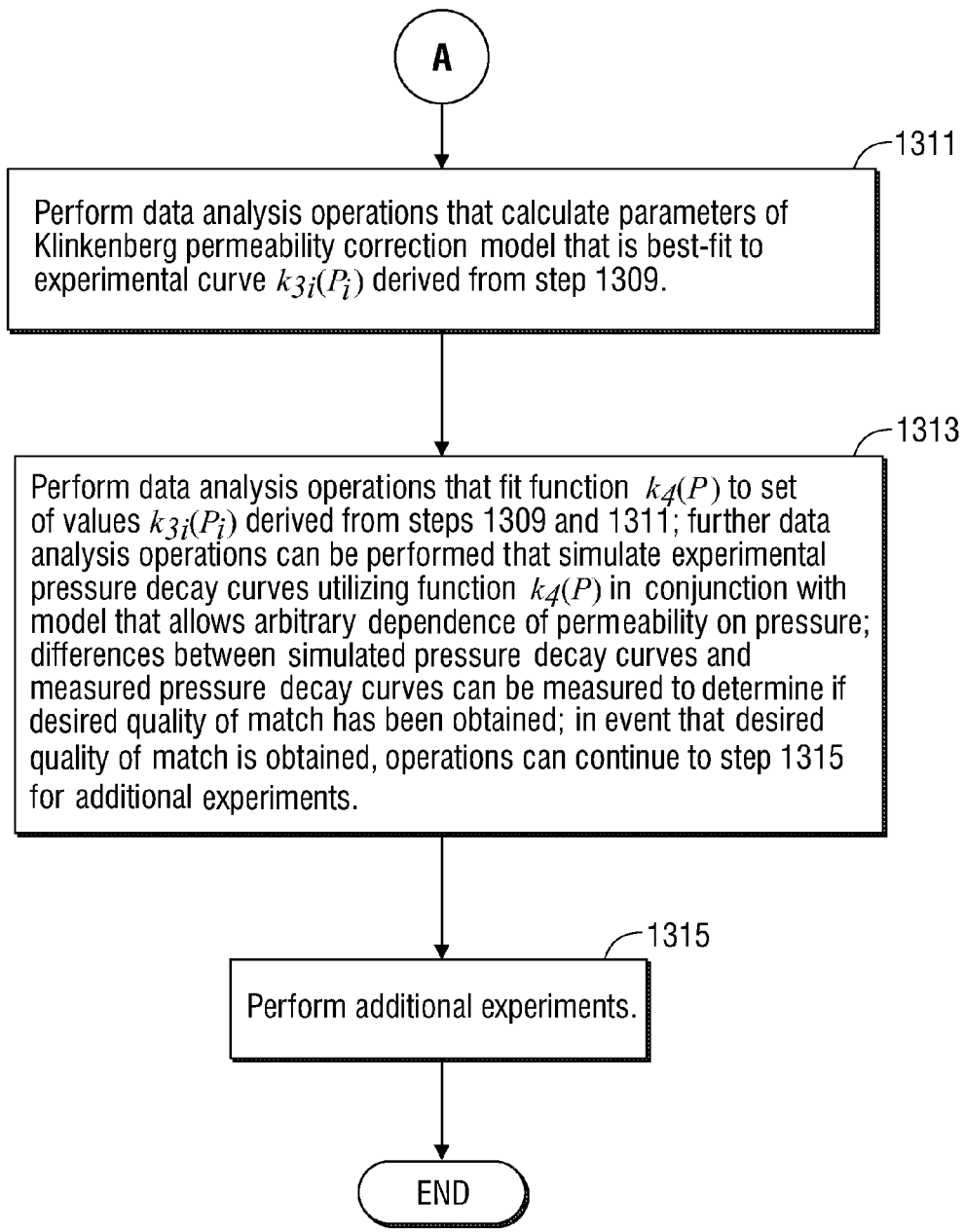

Measuring the apparent permeability of a microporous sample can be carried out with the isolated cell pressure decay apparatus of FIG. 2 in conjunction with the operations illustrated in flowchart of FIGS. 13A and 13B. In step 1301, the microporous sample is loaded into the sample cell of the apparatus of FIG. 2. One or more billets 127 may be added into the sample cell in order to minimize dead volume.

In step 1303, a sequence of pressure decay tests at different initial pressures is performed and the results recorded by the apparatus. This can be done using scripts similar to ascending and descending 'sweep 1' and 'sweep 2' used for calibration of system volumes, pressure transducer non-linearity, and volume compressibilities at different pressures. The number of tests in each of the sweeps may need to be decreased in order to increase the initial pressure difference between the reference and sample cells before each of the pressure decay tests to as few as three tests at different pressures in the working pressure range of the system.

In step 1305, data analysis operations are performed that interpret the pressure decay curves that result from the pressure decay tests of step 1303 independently, by fitting each pressure decay curve individually to a proxy model (which, for example, can be based on Eq. (22) as described above) with constant gas compressibility and pressure-independent compressibility. This proxy model is fast to compute and allows fully automatic fitting. Since every pressure decay test is run at a different pressure and the curves are interpreted independently, extracted values of apparent permeability $k_{2i}(P_i)$ will change with pressure. Note, that flow conditions in the pressure decay test are quite different from steady state flow through cylindrical plugs. In the case of flow through the plug, the pressure difference across the sample is small compared to mean pressure levels, and the pressure-dependent permeability is almost constant throughout the sample. In the pressure decay test, the initial pressure difference is almost the same as the final pressure, and the pressure and the inferred permeability inside the sample changes both in space and time. However, 80% of the test time the pressure throughout most of the sample is close to final pressure. Therefore, the apparent permeability $k_{2i}(P_i)$ is parameterized by the sample cell pressure $P_i=P(t_{end})$ at the end of the experiment, $t_{end}=\tau$.

In step 1307, data analysis is performed to calculate the parameters of the Klinkenberg permeability correction model defined by Eq. (46) that is best-fit to the experimental curve $k_{2i}(P_i)$ derived from step 1305. Such analysis can derive the parameters $k_0$ and b of the best fit curve.

In step 1309, data analysis operations are performed that interpret the pressure decay curves that result from the pressure decay tests of step 1303 by fitting the pressure decay curves to a computational pressure decay model with variable gas compressibility and Klinkenberg permeability correction defined by Eq. (46). This model is computationally inexpensive. The Klinkenberg permeability correction can be based on the parameters $k_0$ and b derived from step 1307 or from step 1311. Such analysis derives the improved pressure-dependent permeability values $k_{3i}(P_i)$.

In step 1311, data analysis is performed to calculate the parameters of the Klinkenberg permeability correction model defined by Eq. (46) that is best-fit to the experimental curve $k_{3i}(P_i)$ derived from step 1309. Such analysis can derive new improved parameters $k_0$ and b for the best-fit curve.

The operations of steps 1309 and 1311 can be repeated over multiple iterations until the results converge. The criteria for convergeance can be based on the change in the experimental curve $k_{3i}(P_i)$ derived in step 1309 (or the parameters $k_0$ and b derived in step 1311) satisfying a predetermined threshold for consistency. Upon convergeance, the parameters $k_0$ and b as derived in step 1309 are defined by a self-consistent set of values $k_{3i}(P_i)$. Furthermore, the parameters $k_0$ and b as derived in step 1309 are used as part of the analytical function, denoted $k_4(P)$, that describes pressure dependent permeability and the operations can continue to step 1315. Otherwise, the operations can continue to step 1313 for further improvement of pressure-dependent permeability approximation.

In step 1313, data analysis operations can be performed that fit the function $k_4(P)$ to approximate all values $k_{3i}(P_i)$ derived from previous steps. Function $k_4(P)$ can be defined by Eq. (47), or any other analytical model of permeability dependence on pressure, or, $k_4(P)$ can be a smooth piecewise spline interpolation of $k_{3i}(P_i)$. Further data analysis operations can be performed that simulate the experimental pressure decay curves utilizing the function $k_4(P)$ in conjunction with the models of Eqs. (22)-(24) that allow for arbitrary dependence of permeability on pressure. This model is computationally expensive. The differences between the simulated pressure decay curves and the measured pressure decay curves are measured to determine if the results converge. The criteria for convergeance can be based on whether a desired quality of match between the simulated pressure decay curves and the measured pressure decay curves has been obtained. If not, the function $k_4(P)$ can be updated and the operations of step 1313 repeated until the desired quality of match is obtained. In the event that the desired quality of match is obtained, the operations can continue to step 1315 for additional analysis.

In step 1315, one or more additional experiments can be performed to characterize properties of the microporous sample. Examples of such additional experiments are described below with respect to FIGS. 14-17.

The operations end after completing step 1315.

In general, the operations of steps 1305 to 1313 perform two loops of fit improvement. The first loop iteratively improves the parameters $k_0$ and b and uses the Klinkenberg pressure dependence of Eq. (46) only, because the computational model to generate pressure-time curves in this case is fast. The second loop uses the best fit from the first loop to start iterative improvement of arbitrary user defined function $k_4(P)$, which has to use computationally expensive calculation of pressure curves. The second loop is terminated if the match is already good.

The pressure decay measurements can be influenced by the slip effect of testing gas. In liquid laminar flow, the layer of molecules adjacent to and contacting the solid walls of the pores of the sample is stationary. The velocity profile of the liquid is maximum at the center of the passageway and zero at the walls. However, when using gas in the same flow system, the gas velocity profile is not zero at the walls, but has a finite velocity in the direction of flow. Gas molecules are in constant motion, colliding with one another after traveling an average distance equal to the "mean free path." At lower pressures, the mean free path is greater, and the distance between molecular collisions is increased. Internal resistance to flow is provided by gas molecular collisions with the walls. At any location on a wall, there will be some periods when no gas molecule is in contact with the wall, yet the congregation of gas molecules is continuing its movement through the pore due to molecular diffusion (slip) and not pressure differential. During these periods of no wall contact, flow is being achieved without the normally expected friction loss at the wall. The result is that the gas molecules pass through the porous medium more easily than expected (i.e., the calculated permeability of the rock sample is artificially high). As might be expected, gas flow at higher pressures reduces the mean free path between molecular collisions, and the calculated permeability more closely approximates the true absolute permeability of the rock sample.

As was discussed earlier, the most suitable gas to estimate ultra-low permeability is helium, which has the lowest specific heat capacity and the highest thermal diffusivity. This results in the smallest amplitude and shortest time thermal effects that contaminate pressure diffusion measurements. Also helium has a very small molecule size that allows the testing gas to reach the smallest pores, and it is inert gas, which is not chemically interacting with any other species and therefore is not adsorbing inside of any samples. At the same time, there are additional pieces of information about the microporous sample that can be extracted by pressure decay testing of the same material with different gases.

The free mean path of gas molecules 2 is defined by:

$$\lambda = 1.881 \frac{\mu}{P} \sqrt{\frac{RT}{M}}, \quad (48)$$

where P is pressure,
μ is gas viscosity,
R is the universal gas constant,
T is temperature, and
M is the molar mass of the gas.

For the pair of two gases, e.g., helium and argon, considered at the same pressure and temperature their free mean paths will be related by:

$$\lambda_{Ar} = \lambda_{He} \left( \frac{\mu}{\sqrt{M}} \right)_{Ar} \bigg/ \left( \frac{\mu}{\sqrt{M}} \right)_{He}. \quad (49)$$

A similar equation can be used for other pairs of gases.

Typically molecular weight tends to change more from gas to gas than viscosity and heavier gases have smaller free mean path under same conditions. As discussed herein, the pressure dependence of gas permeability is defined by the ratio of free mean path to characteristic size of flow channels, λ/w. Therefore, testing of the same microporous sample with the same w with a heavier (smaller λ) gas is equivalent to testing with the lighter (larger λ) gas at higher testing pressure. Both gases must be inert, i.e. not chemically interacting with the sample. With this in mind, by combining pressure dependent measurements of permeability made within the working pressure range of the equipment using different gases, it is possible to effectively expand the pressure range of slip effect characterization. From Eqs. (48) and (49) it follows that permeability of a heavier gas (e.g., argon) at lower pressure, P, is equivalent to permeability of a lighter gas (e.g., helium) at higher pressure:

$$k_{He}\left(\frac{\lambda_{He}}{\lambda_{Ar}} \cdot P\right) = k_{He}\left(\left(\frac{\mu}{\sqrt{M}}\right)_{He} \bigg/ \left(\frac{\mu}{\sqrt{M}}\right)_{Ar} \cdot P\right) = k_{Ar}(P), \quad (50)$$

where $k_{He}$ is the permeability measured with the lighter (helium) test gas,
$k_{Ar}$ is the permeability measured with the heavier (argon) test gas, $\lambda_{He}$ is the free mean molecule path of the lighter (helium) test gas, $\lambda_{Ar}$ is the free mean molecule path of the heavier (argon) test gas, $$\left(\frac{\mu}{\sqrt{M}}\right)_{He}$$

is the ratio of the gas viscosity μ to the square root of the molar mass M for the lighter (helium) test gas, $$\left(\frac{\mu}{\sqrt{M}}\right)_{Ar}$$

is the ratio of the gas viscosity μ to the square root of the molar mass M for the heavier (argon) test gas, and P is pressure.

Note that the higher pressure, $$\frac{\lambda_{He}}{\lambda_{Ar}} \cdot P,$$

can go beyond the working range of the testing equipment.

For the extended pressure dependent permeability characterization it is optimal to use a series of homologous noble monoatomic gases, because they are inert and because thermal capacity of monoatomic gases is the smallest, since it is growing with the number of interatomic bonds and degrees of freedom in a molecule. Early-time thermal effect on the pressure measurements while using heavier monoatomic gases will be higher than with helium, because thermal diffusivity will be lower due to smaller molecule velocity. The second best option would be diatomic gases that have a step higher thermal capacity. For example, nitrogen as a testing gas has quite high value due to its low chemical activity, cost efficiency, and actually relatively high thermal diffusivity due to its low molecular weight.

Figure 14:
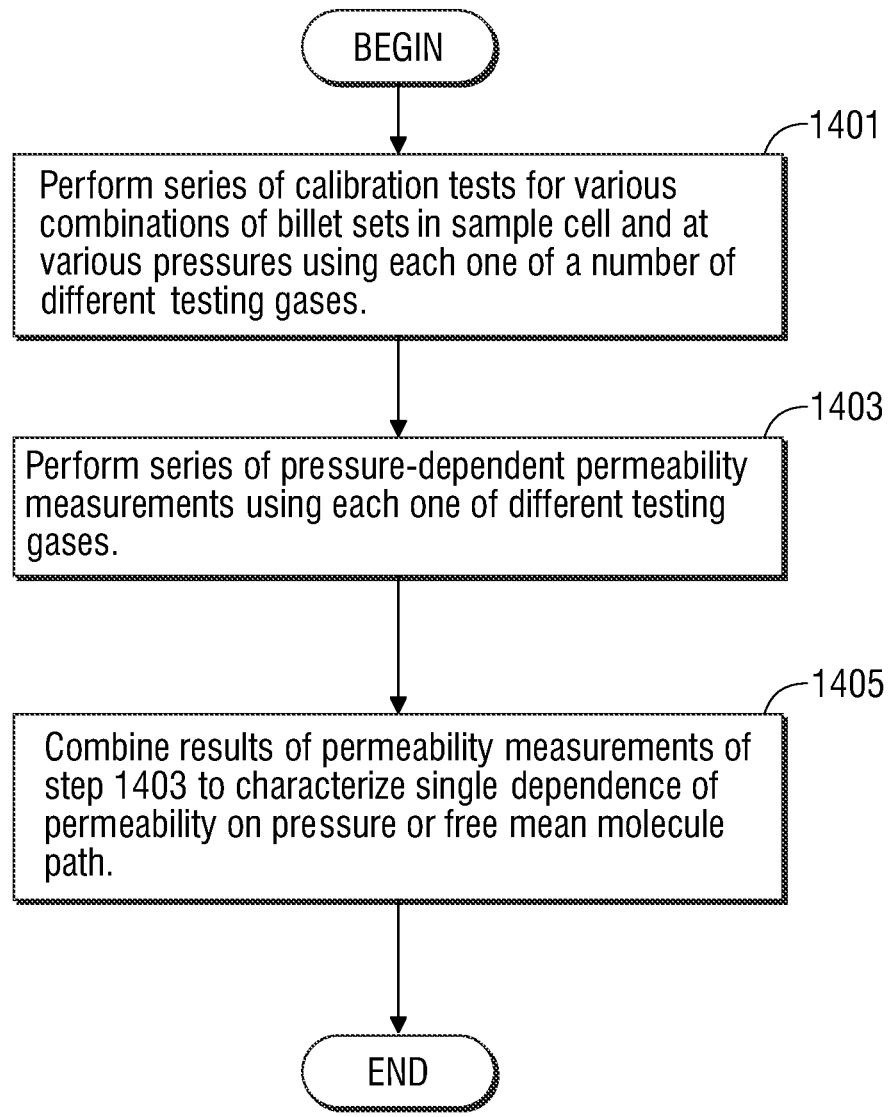
FIG. 14 is a flow chart of operations carried out by the apparatus of FIG. 2 to characterize the dependence of permeability of a microporous sample on gas slippage.

FIG. 14 is a flow chart that illustrates additional experiments that can be carried out using the apparatus of FIG. 2 to characterize permeability of the microporous sample in a manner that accounts for such slip effect. The additional experiments employ a number of different testing gases. The number of different testing gases is preferably realized from monoatomic gases (first preference), diatomic gases (second preference) or combinations thereof.

In step 1401, a series of calibration tests is performed using the apparatus of FIG. 2 for various combinations of billet sets 127 in the sample cell 103 and at various pressures using each one of the different testing gases in order to quantify early-time thermal effects as a function of volume ratio, pressure and kind of gas.

In step 1403, a series of pressure dependent permeability measurements is performed using each one of the different testing gases. The permeability measurements of the series employ the testing apparatus of FIG. 2, which is operated to carry out pressure tests without confinement and data analysis operations in the manner described above in order to measure properties of the sample, including permeability of the sample.

In step 1405, the results of the permeability measurements of step 1403 are combined by translating all permeabilities for all gases to the equivalent permeability of the gas with the largest free mean path (typically helium), using Eq. (50). The combined results can be used to characterize a single dependence of permeability on pressure or free mean molecule path.

In another embodiment, additional experiments can be performed to characterize adsorption of the microporous sample. The additional experiments employ a testing gas that is non-adsorptive with respect to the microporous sample along with a testing gas that is adsorptive with respect to the microporous sample (such as methane for organic rich reservoir rock). The adsorptive characteristics of microporous samples can be estimated by doing isolated-cell pressure decay testing on the same sample using the adsorptive and non-adsorptive testing gases and then comparing the results.

Figure 15:
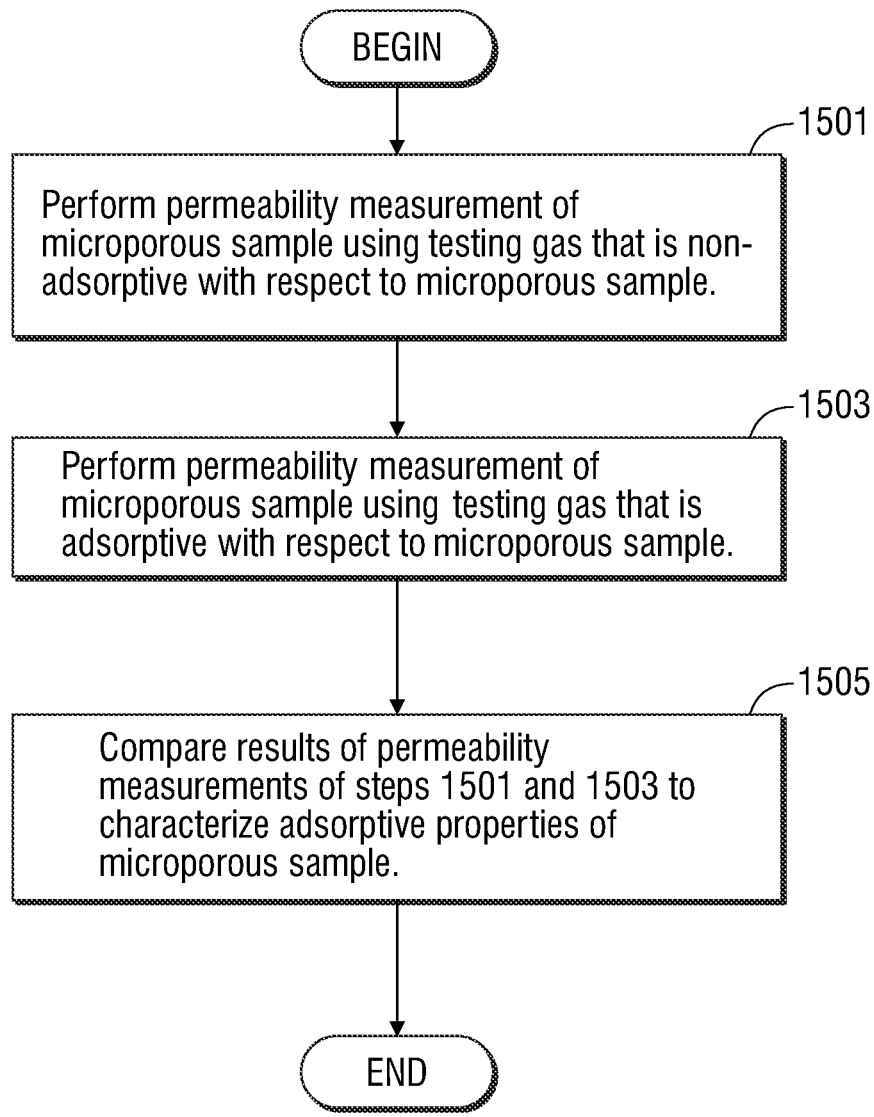
FIG. 15 is a flow chart of operations carried out by the apparatus of FIG. 2 to characterize the adsorptive properties of a microporous sample.

FIG. 15 is a flow chart illustrating operations that characterize adsorption of a microporous sample employing pressure decay testing. In step 1501, a permeability measurement of a microporous sample is performed using the testing gas that is non-adsorptive with respect to the microporous sample. The permeability measurement employs the testing apparatus of FIG. 2, which is operated to carry out a pressure test without confinement and data analysis operations in the manner described above in order to measure properties of the microporous sample, including permeability of the sample. It is assumed that early-time thermal effect for the non-adsorptive testing gas is known.

In step 1503, a permeability measurement of a microporous sample is performed using the testing gas that is adsorptive with respect to the microporous sample. The permeability measurement employs the testing apparatus of FIG. 2, which is operated to carry out a pressure test without confinement and data analysis operations in the manner described above in order to measure properties of the microporous sample, including permeability of the sample. It is assumed that early-time thermal effect for the adsorptive testing gas is known.

In step 1505, the results of the permeability measurements of steps 1501 and 1503 can be compared and analyzed in order to characterize adsorption of the microporous sample. Specifically, if some amount of the adsorptive testing gas is actually adsorbed, that gas is not contributing to gas pressure in the pore volume and the sample cell and therefore estimated gas-probed porosity is increased. The amount of adsorbed gas is estimated from the difference in measured gas-probed porosity. If gas slip in the sample or pressure dependence of permeability is well established, it is possible to extrapolate what would be the permeability of the sample for the gas which has the same viscosity and molar mass as the adsorptive gas. By comparing the extrapolated permeability for equivalent non-adsorptive gas and the permeability measured with corresponding adsorptive gas it is possible to estimate the adsorption rate of the microporous sample.

In yet another embodiment, additional experiments can be performed to characterize thermal properties of microporous rock samples. More specifically, early-time thermal effects due to adiabatic expansion and compression of the testing gas can be highly variable depending on the type of testing gas used. For helium, the thermal effect can be as short as 2-5 seconds depending on testing conditions. For heavier gases with higher thermal capacity and lower thermal diffusivity, thermal effects can be tens of seconds long, which may be comparable to total gas diffusion time in many samples. Such thermal effects can make permeability measurement with the heavier gas alone impossible. However, the prolonged period of thermal dissipation recorded on the pressure signal carries more information about the thermal properties of the sample in the cell. The thermal properties of a microporous sample can be estimated by doing isolated-cell pressure decay testing on the same sample using helium and a heavier testing gas.

Figure 16:
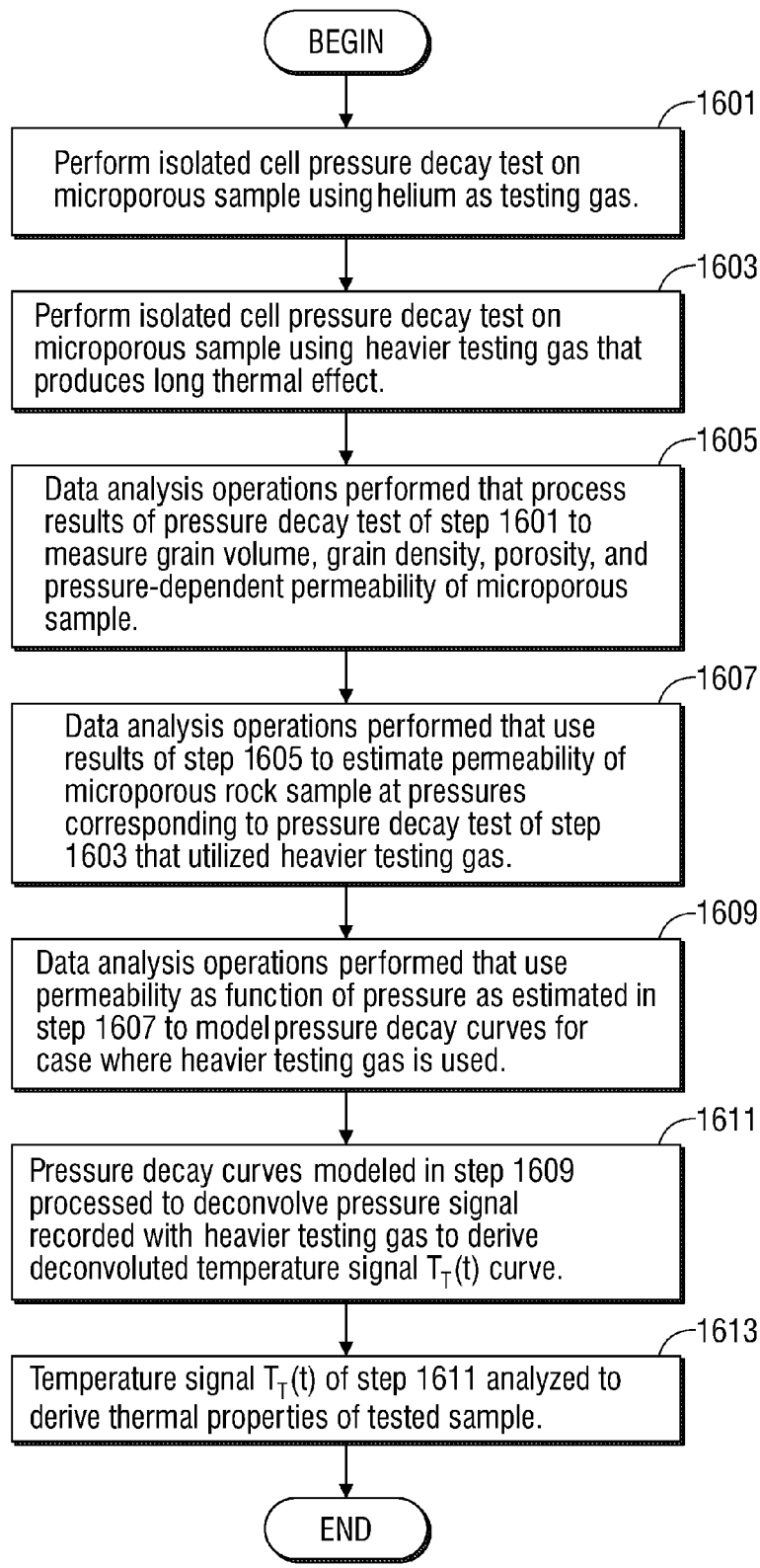
FIG. 16 is a flow chart of operations carried out by the apparatus of FIG. 2 to characterize the thermal properties of a microporous sample.

FIG. 16 is a flow chart illustrating operations that characterize thermal properties of a microporous rock sample employing pressure decay testing. In step 1601, an isolated pressure decay testing at multiple pressures is performed on a microporous rock sample using helium as the testing gas. The pressure decay test employs the testing apparatus of FIG. 2, which is operated to carry out a pressure test without confinement using helium as the testing gas. It is assumed that early-time thermal effect for the helium testing gas is known.

In step 1603, an isolated cell pressure decay test is performed on the microporous rock sample using a heavier testing gas that produces a long thermal effect. Again, the pressure decay test employs the testing apparatus of FIG. 2, which is operated to carry out a pressure test without confinement using the heavier testing gas. It is assumed that early-time thermal effect for the heavier testing gas is known. Note that the pressure decay measurements of step 1603 combine both thermal effect and gas diffusion.

In step 1605, data analysis operations are performed that process the results of the pressure decay testing at multiple pressures of step 1601 to measure grain volume, grain density, porosity, and pressure dependent permeability of the microporous rock sample for the case where helium is the testing gas. For example, the sample volume, porosity, permeability, and grain volume of such fragments can be estimated using Eqs. (28), (29), (30), (31A), (31B), (32), and (33) as described above. The function, approximating experimental pressure dependent permeability of the sample, $k_{He}(P)$, can be obtained using operations similar to those described above with respect to FIGS. 13A and 13B.

In step 1607, data analysis is performed that uses the results of step 1605 to estimate equivalent permeability of the heavier gas for the microporous rock sample at the pressures corresponding to the pressure decay test of step 1603 that utilized the heavier testing gas. Equivalent permeability of the heavier testing gas is estimated using pressure dependent permeability for the lighter gas and using Eq. (50) to estimate equivalent pressure:

$$k_T(P_T) = k_{He}\left(\left(\frac{\mu}{\sqrt{M}}\right)_{He} \bigg/ \left(\frac{\mu}{\sqrt{M}}\right)_T \cdot P_T\right), \quad (51)$$

where index (T) denotes permeability, testing pressure, and other properties of the heavier testing gas, that creates substantial thermal signal during pressure decay.

In step 1609, data analysis is performed that uses the equivalent permeability of the microporous rock sample for the heavier gas estimated in step 1607 to generate the equivalent pressure decay curve without thermal effects for the case where the heavier testing gas is used. The equivalent pressure decay curve for the heavier gas, denoted $P_{T\_from\_He}(t)$ at pressure equal to $P_T(P_{T\_from\_He}(t_{end})=P_T)$ and without thermal effects, is generated using the computational model with constant permeability defined by $k_T$ estimated using Eq. (51).

In step 1611, the pressure decay curves modeled in step 1609 are processed to deconvolute the pressure signal recorded with the heavier testing gas, which is a mixed result of pressure diffusion and temperature dissipation, to derive a temperature signal (curve) $T_T(t)$ representing temperature in the sample cell as a function of time for the pressure decay test of step 1603 that utilizes the heavier testing gas as follows:

$$T_T(t) = \frac{P_T(t)}{P_{T\_from\_He}(t)} T_T(t_{end}), \quad (52)$$

where $T_T(t)$ is the deconvoluted temperature curve in the sample cell as a function of time, t, for the pressure decay test of step 1603, $P_{T\_from\_He}(t)$ is the equivalent pressure decay curve of heavier gas isolated from thermal effect obtained during step 1609, $P_T(t)$ is the pressure decay curve of the heavier gas recorded at step 1603.

This deconvolution procedure allows for isolation of the component of the pressure signal that is caused by thermal dissipation alone In step 1613 the deconvoluted temperature signal $T_T(t)$ from step 1611 is further processed to estimate thermal properties of the microporous sample. The thermal properties can be derived from a forward numerical model of temperature dissipation in the sample cell enclosing the sample and billets that is used to solve the inverse problem. The model takes as an input all essential thermal properties of the sample cell (geometry, thermal conductivity and thermal capacity of cell walls), of the testing gas (mole amount, thermal conductivity and capacity) and billets (billet set, geometry, thermal conductivity and capacity of all billets). The initial condition for the model is defined by the initial amount of heat stored in the gas, which is estimated from initial temperature $T_T(t)$, and the amount and heat capacity of the testing gas. Then, multiple simulation of the model are performed with varied thermal conductivity and thermal capacity of the microporous sample until the best match between the modeled $T_T(t)$ and deconvoluted $T_T(t)$ from step 1611 is found.

In another embodiment, the thermal properties of the sample can be derived from a full calibrated forward numerical model of the isolated pressure decay equipment interacting with the microporous sample that is used to solve the inverse problem. The model takes as an input all essential properties of the testing equipment (volumes, thermal properties and geometry of cells), all essential testing conditions (initial pressures, billet set, thermal properties of billets, gas properties) and properties of the tested material (grain volume, porosity, pressure dependent permeability, which are known from the testing with helium, size and geometry of fragments and thermal properties of the material). All listed inputs except thermal properties of the material are fixed. Then, multiple simulations of the model are performed with varied thermal properties of the material until the best match with experimental curves which carry considerable thermal effect is found.

In yet another embodiment, the isolated pressure decay testing as described herein can be extended to measure saturation dependent permeability of a microporous sample. Relative permeability curves that specify how permeability of specific phases changes as a function of phase saturation is a key input for the simulation and understanding of the multiphase flow in porous rock. For example, in heterogeneous rocks with very fine porosity such as reservoir shales, direct measurement of relative permeability is not practical because of the extremely low mobility of the liquid phase. An important piece of information that helps to understand relative permeability is to identify permeability to gas, which is more mobile, as a function of the saturation by the less permeable liquid phase. Isolated cell pressure decay testing on fragmented or controlled shape samples of small size is a suitable method to characterize this dependence, because of its high sensitivity to permeability variations in the low permeability range and because it takes a reasonably short amount of time to diffuse desired liquids into samples to create necessary saturation levels.

Figure 17:
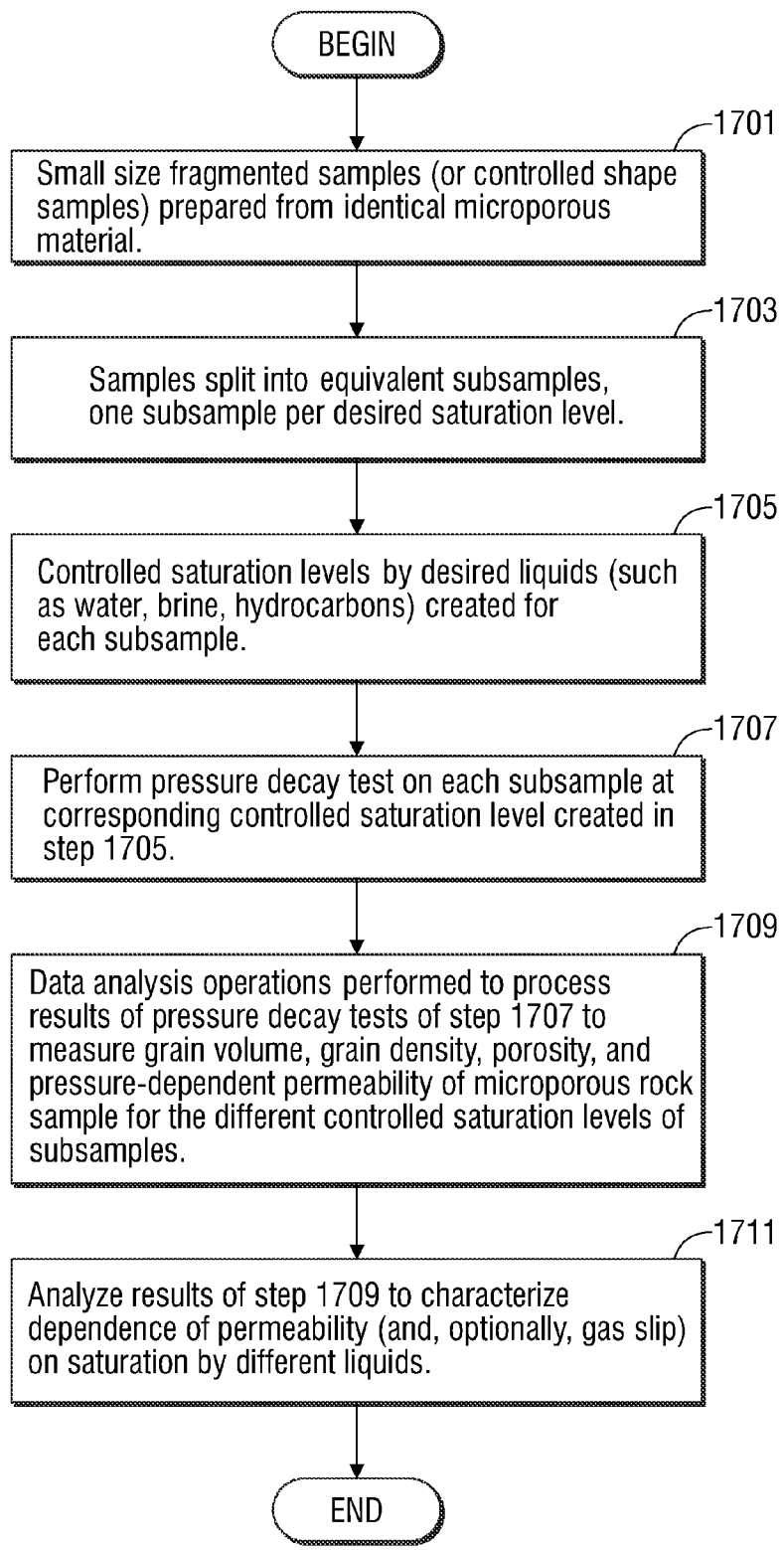
FIG. 17 is a flow chart of operations carried out by the apparatus of FIG. 2 to characterize the dependence of permeability of a microporous sample on saturation of different liquids.

FIG. 17 is a flow chart illustrating operations that characterize saturation dependent permeability of a microporous sample. In step 1701, small size fragmented samples (or controlled shape samples) are prepared from identical microporous material. The amount of such samples is selected to provide samples to estimate permeability at all desired saturation levels. The size of the samples is dictated by the expected or estimated highest (unsaturated) permeability of the sample, which must be within the measurable permeability range at the selected size.

In step 1703, the samples are split into equivalent subsamples, one subsample per desired saturation level.

In step 1705, controlled saturation levels by one or more desired liquids (such as water, brine, hydrocarbons) are created for each subsample. The controlled saturation levels of the desired liquid(s) can be attained by controlled evaporation or solvent extraction of the fully saturated subsample.

In step 1707, a pressure decay test is performed on each subsample at the corresponding controlled saturation level created in step 1705. The pressure decay test employs the testing apparatus of FIG. 2, which is operated to carry out a pressure decay test without confinement on each subsample at the controlled saturation levels created in step 1705. Optionally, the operations can be performed at different pore pressures as described above.

In step 1709, the results of the pressure tests of step 1707 are processed to measure grain volume, grain density, porosity, and pressure dependent permeability of the microporous rock sample for the different controlled saturation levels of the subsamples. For example, the sample volume, porosity, permeability, and grain volume of such fragments can be estimated using Eqs. (28), (29), (30), (31A), (31B), (32), and (33) as described above.

In step 1711, the results of step 1709 can be analyzed to characterize the dependence of permeability (and, optionally, gas slip) on the saturation by different liquids. This is done via comparing and understanding how the permeability and gas slip described by Klinkenberg parameters or by pressure dependent permeability $k_4(P)$ change with different saturation levels.

In yet another embodiment the pressure decay testing at different pressures described in FIGS. 13A and 13B; the pressure decay testing with different gases and pressure described in FIG. 14; the pressure decay testing to characterize adsorptive properties of the rock described in FIG. 15; pressure decay testing with different saturation levels described in FIG. 17 can also be done using the experimental apparatus of FIG. 10 under various confinement, if required by a testing program. This testing requires cylindrical rock samples, (samples of other shapes can be embedded into machinable impermeable matrix around them, which is then machined to create cylindrical shape of the composite sample). For the same type of microporous material, this testing also takes a longer time than unconfined pressure decay testing, which can use samples of smaller size.

There have been described and illustrated herein several embodiments of an apparatus and methodology for measuring properties of a microporous material. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A method for characterizing properties of a porous sample, comprising:
   a) providing a test apparatus including a sample cell and associated first pressure sensor, wherein the sample cell has a configuration where the sample cell is filled with test fluid under pressure and isolated from other parts of the test apparatus, and wherein the first pressure sensor has a configuration that measures pressure of the sample cell when the sample cell is isolated from other parts of the test apparatus;
   b) dividing the porous sample into a number of pieces having controlled shapes with sizes corresponding to thickness of the controlled shapes and selected surfaces of the pieces are sealed with an impermeable material for characterization of directional permeability and increasing signal-to-noise ratio by decreasing dead volume;
   c) loading pieces of the porous sample resulting from b) into the sample cell of the test apparatus;
   d) subsequent to c), configuring the test apparatus to perform a sequence of test operations whereby the loaded sample cell is filled with test fluid under pressure and isolated from other parts of the test apparatus and the first pressure sensor is used to measure and store pressure data that represents pressures measured by the pressure sensor over time;
   e) using a data processing system to process the pressure data generated and stored in d) in conjunction with a computational model that includes a set of pressure curves with a number of curve-related variables and associated values in order to identify a matching pressure curve; and
   f) using the data processing system to process the values of the curve-related variables for the matching pressure curve identified in e) in order to derive bulk properties of the porous sample.

2. A method according to claim 1, wherein the porous sample comprises a porous rock sample.

3. A method according to claim 1, wherein the test apparatus further includes:
   an intake valve fluidly coupled to a source of test fluid;
   a reference cell fluidly coupled to the source of test fluid via the intake valve;
   an isolation valve fluidly coupled between the reference cell and the sample cell;
   an exhaust port;
   an exhaust valve fluidly coupled between the sample cell and the exhaust port; and
   a second pressure sensor associated with the reference cell for measuring pressure within the reference cell.

4. A method according to claim 3, wherein:
   the intake valve, the isolation valve, and the exhaust valve are electronically-controlled;
   the data processing system interfaces to the intake valve, the isolation valve, and the exhaust valve via electronic signals communicated therebetween in order to control operation of the intake valve, the isolation valve, and the exhaust valve; and
   the data processing system interfaces to the first and second pressure sensors via electronic signals communicated therebetween in order to generate and store first and second pressure data representing the pressures measured by the first and second pressure sensors, respectively, over time.

5. A method according to claim 1, wherein the bulk properties of the porous sample derived in f) are selected from the group consisting of bulk volume, bulk density, porosity, permeability, grain volume, grain density, and effective density-based porosity.

6. A method according to claim 1, wherein the computational model is based on an analytical decay function that includes three parameters $\alpha$, $\beta$ and $\tau$, where the parameter $\alpha$ is a storage coefficient that defines the ratio of pore volume to dead volume in the sample under test, the parameter $\beta$ relates to the final pressure in the sample cell when pressure inside and outside of the pore volume of the sample under test has stabilized, and parameter $\tau$ is a relaxation time.

7. A method according to claim 6, wherein the bulk properties of the porous sample derived in f) are selected from the group consisting of bulk volume based on value of the parameter $\beta$ for the matching pressure curve, porosity based on value of the parameter $\alpha$ for the matching pressure curve, permeability based on the parameter $\tau$ for the matching pressure curve, grain volume based on the bulk volume and the porosity, bulk density based on bulk volume, grain density based on grain volume, and effective density-based porosity based on bulk and grain density.

8. A method according to claim 1, wherein the processing of e) derives corrected pressure values based on the pressure data generated and stored in d) and matches the corrected pressure values to the set of pressure curves derived from the computational model in order to identify a matching pressure curve.

9. A method according to claim 1, wherein the pieces resulting from b) and loaded into the sample cell in c) are fragments of uncontrolled shape with sizes corresponding to the radius of such fragments.

10. A method according to claim 1, wherein the pieces of controlled shape are slices of a core sample with varying thickness.

11. A method according to claim 6, wherein using the data processing system to process the pressure data generated and stored in d) in conjunction with the computational model in order to identify value of the parameter $\tau$ for the matching pressure curve and to determine if the pieces resulting from b) require reduction in size based on the value of the parameter $\tau$ for the matching pressure curve.

12. A method according to claim 11, wherein the data processing system compares the time period of the pressure data as measured by the pressure sensor with the parameter $\tau$ for the matching pressure curve to determine if the pieces resulting from b) require reduction in size.

13. A method according to claim 12, wherein the data processing system determines that the pieces resulting from b) require reduction in size in the event that the time period of the pressure data as measured by the pressure sensor is smaller than the parameter $\tau$ for the matching pressure curve.

14. A method according to claim 13, further comprising:
in the event that the data processing system determines that the pieces resulting from b) require reduction in size, repeating b) in order to reduce maximum size of the pieces that result from b).

15. A method according to claim 1, further comprising:
g) partitioning the pieces of the porous sample resulting from b) into size-groups of different sizes;
h) performing a sequence of operations for each given size-group of sample pieces resulting from g), wherein the sequence of operations of h) includes
h1) loading one or more pieces of the given size-group into the sample cell of the test apparatus,
h2) subsequent to h1), configuring the test apparatus to perform a sequence of test operations whereby the loaded sample cell is filled with test fluid under pressure and isolated from other parts of the test apparatus and the first pressure sensor is used to measure and store pressure data that represents pressures measured by the first pressure sensor over time,
h3) using the data processing system to process the pressure data generated and stored in h2) in conjunction with the computational model in order to identify a matching pressure curve, and
h4) using the data processing system to process the values of the curve-related variables for the matching pressure curve identified in h3) in order to derive properties of a given size-group of pieces.

16. A method according to claim 15, wherein the processing of h3) derives corrected pressure values based on the pressure data generated and stored in h2) and matches the corrected pressure values to the set of pressure curves derived from the computational model in order to identify the matching pressure curve.

17. A method according to claim 15, wherein the processing of h4) derives distribution of permeability per pore volume fraction in the sample.

18. A method according to claim 15, wherein the processing of h4) characterizes a microstructure of the sample with regard to the presence and characteristic length scale of structural elements.

* * * * *